US010966620B2

(12) United States Patent
Boers et al.

(10) Patent No.: US 10,966,620 B2
(45) Date of Patent: Apr. 6, 2021

(54) DEVICE FOR INTERACTING WITH NEUROLOGICAL TISSUE AND METHODS OF MAKING AND USING THE SAME

(71) Applicant: Aleva Neurotherapeutics SA, Lausanne (CH)

(72) Inventors: Marc Boers, Cully (CH); Andre Mercanzini, St-Sulpice (CH); Jean-Michel Dougoud, Villarsel-le-Gibloux (CH); Alexandre Michalis, Le Grand-Saconnex (CH)

(73) Assignee: Aleva Neurotherapeutics SA, Lausanne (CH)

( * ) Notice: Subject to any disclaimer, the term of this patent is extended or adjusted under 35 U.S.C. 154(b) by 982 days.

(21) Appl. No.: 15/311,082

(22) PCT Filed: May 15, 2015

(86) PCT No.: PCT/IB2015/053610
§ 371 (c)(1),
(2) Date: Nov. 14, 2016

(87) PCT Pub. No.: WO2015/173787
PCT Pub. Date: Nov. 19, 2015

(65) Prior Publication Data
US 2017/0105641 A1  Apr. 20, 2017

Related U.S. Application Data

(60) Provisional application No. 61/994,359, filed on May 16, 2014.

(51) Int. Cl.
*A61B 5/04* (2006.01)
*A61N 1/05* (2006.01)
*A61B 5/00* (2006.01)

(52) U.S. Cl.
CPC .......... *A61B 5/04001* (2013.01); *A61B 5/685* (2013.01); *A61B 5/686* (2013.01);
(Continued)

(58) Field of Classification Search
CPC ............ A61B 5/004001; A61B 5/0422; A61B 5/6852; A61B 5/6848; A61B 5/685;
(Continued)

(56) References Cited

U.S. PATENT DOCUMENTS 4,245,645 A   1/1981  Arseneault et al.
4,550,733 A   11/1985 Liss et al.
(Continued)

FOREIGN PATENT DOCUMENTS

CN   101027085 A    8/2007
CN   101600470 A    12/2009
(Continued)

OTHER PUBLICATIONS

US 8,388,533 B2, 03/2013, Hafezi et al. (withdrawn)
(Continued)

*Primary Examiner* — Eun Hwa Kim
(74) *Attorney, Agent, or Firm* — Foley & Lardner LLP; James De Vellis

(57) ABSTRACT

Described herein are microelectrode devices to provide localized neural recording or neural stimulation to a neurological target. The device includes a plurality of electrodes disposed along the shafts of deployable flexible pins. The deployable flexible pins are enclosed within an elongated probe shaft, and can be expanded from their enclosure. Additionally, a specifically manufactured outer housing can be coupled to at least a portion of the elongated probe shaft. During deployment of the flexible pins the outer housing of the microelectrode device reduces friction between the flex-
(Continued)

ible pins and the probe shaft and reduces delamination of the flexible pins during deployment.

24 Claims, 30 Drawing Sheets

(52) U.S. Cl.
CPC .......... *A61N 1/0534* (2013.01); *A61N 1/0551* (2013.01); *A61B 2562/028* (2013.01)

(58) Field of Classification Search
CPC ........ A61B 2018/143; A61B 2562/028; A61N 1/0551; A61N 1/686; A61N 1/0534; A61N 1/0472; A61N 1/048
See application file for complete search history.

(56) References Cited

U.S. PATENT DOCUMENTS

| | | | |
|---|---|---|---|
| 4,837,049 A | 6/1989 | Byers et al. |
| 4,917,093 A | 4/1990 | Dufresne et al. |
| 4,928,297 A | 5/1990 | Tsutsui et al. |
| 4,969,468 A | 11/1990 | Byers et al. |
| 4,989,617 A | 2/1991 | Memberg et al. |
| 5,095,905 A | 3/1992 | Klepinski |
| 5,215,088 A | 6/1993 | Normann et al. |
| 5,391,250 A | 2/1995 | Cheney et al. |
| 5,400,784 A | 3/1995 | Durand et al. |
| 5,419,777 A | 5/1995 | Hofling |
| 5,458,629 A | 10/1995 | Baudino et al. |
| 5,496,369 A | 3/1996 | Howard, III |
| 5,524,338 A | 6/1996 | Martyniuk et al. |
| 5,628,317 A | 5/1997 | Starkebaum et al. |
| 5,643,330 A | 7/1997 | Holsheimer et al. |
| 5,679,355 A | 10/1997 | Alexander et al. |
| 5,683,422 A | 11/1997 | Rise |
| 5,697,651 A | 12/1997 | Fernandes |
| 5,697,975 A | 12/1997 | Howard et al. |
| 5,702,429 A | 12/1997 | King |
| 5,713,922 A | 2/1998 | King |
| 5,713,923 A | 2/1998 | Ward et al. |
| 5,716,377 A | 2/1998 | Rise et al. |
| 5,727,552 A | 3/1998 | Ryan |
| 5,752,979 A | 5/1998 | Benabid |
| 5,755,759 A | 5/1998 | Cogan |
| 5,782,798 A | 7/1998 | Rise |
| 5,797,970 A | 8/1998 | Pouvreau |
| 5,800,474 A | 9/1998 | Benabid et al. |
| 5,800,535 A | 9/1998 | Howard, III |
| 5,814,092 A | 9/1998 | King |
| 5,824,029 A | 10/1998 | Weijand et al. |
| 5,792,186 A | 11/1998 | Rise |
| 5,833,709 A | 11/1998 | Rise et al. |
| 5,833,714 A | 11/1998 | Loeb |
| 5,843,148 A | 12/1998 | Gijsbers et al. |
| 5,893,883 A | 4/1999 | Torgerson et al. |
| 5,913,882 A | 6/1999 | King |
| 5,921,924 A | 7/1999 | Avitall |
| 5,927,277 A | 7/1999 | Baudino et al. |
| 5,941,906 A | 8/1999 | Barreras et al. |
| 5,957,958 A | 9/1999 | Schulman et al. |
| 5,975,085 A | 11/1999 | Rise |
| 5,978,702 A | 11/1999 | Ward et al. |
| 5,991,668 A | 11/1999 | Leinders et al. |
| 6,011,996 A | 1/2000 | Gielen et al. |
| 6,018,682 A | 1/2000 | Rise |
| 6,024,095 A | 2/2000 | Stanley, III |
| 6,033,403 A | 3/2000 | Tu et al. |
| 6,038,480 A | 3/2000 | Hrdlicka et al. |
| 6,050,992 A | 4/2000 | Nichols |
| 6,094,598 A | 7/2000 | Elsberry et al. |
| 6,104,960 A | 8/2000 | Duysens et al. |
| 6,109,269 A | 8/2000 | Rise et al. |
| 6,125,300 A | 9/2000 | Weijand et al. |
| 6,128,537 A | 10/2000 | Rise |
| 6,129,685 A | 10/2000 | Howard, III |
| 6,161,047 A | 12/2000 | King et al. |
| 6,205,359 B1 | 3/2001 | Boveja |
| 6,205,361 B1 | 3/2001 | Kuzma et al. |
| 6,216,043 B1 | 4/2001 | Swanson et al. |
| 6,227,203 B1 | 5/2001 | Rise et al. |
| 6,253,109 B1 | 6/2001 | Gielen |
| 6,253,110 B1 | 6/2001 | Brabec et al. |
| 6,263,237 B1 | 7/2001 | Rise |
| 6,266,564 B1 | 7/2001 | Hill et al. |
| 6,295,476 B1 | 9/2001 | Schaenzer |
| 6,301,492 B1 | 10/2001 | Zonenshayn |
| 6,319,241 B1 | 11/2001 | King et al. |
| 6,330,466 B1 | 12/2001 | Hofmann et al. |
| 6,337,997 B1 | 1/2002 | Rise |
| 6,343,226 B1 | 1/2002 | Sunde et al. |
| 6,353,762 B1 | 3/2002 | Baudino et al. |
| 6,356,784 B1 | 3/2002 | Lozano et al. |
| 6,356,786 B1 | 3/2002 | Rezai et al. |
| 6,356,787 B1 | 3/2002 | Rezai et al. |
| 6,364,875 B1 | 4/2002 | Stanley, III |
| 6,366,813 B1 | 4/2002 | DiLorenzo |
| 6,374,140 B1 | 4/2002 | Rise |
| 6,375,666 B1 | 4/2002 | Mische |
| 6,379,353 B1 | 4/2002 | Nichols |
| 6,415,187 B1 | 7/2002 | Kuzma et al. |
| 6,434,431 B1 | 8/2002 | Camps et al. |
| 6,459,936 B2 | 10/2002 | Fischell et al. |
| 6,479,999 B1 | 11/2002 | Demeester et al. |
| 6,484,059 B2 | 11/2002 | Gielen |
| 6,493,590 B1 | 12/2002 | Wessman et al. |
| 6,510,347 B2 | 1/2003 | Borkan |
| 6,529,774 B1 | 3/2003 | Greene |
| 6,538,443 B2 | 3/2003 | Morich et al. |
| 6,549,812 B1 | 4/2003 | Smits |
| 6,556,873 B1 | 4/2003 | Smits |
| 6,560,472 B2 | 5/2003 | Hill et al. |
| 6,560,486 B1 | 5/2003 | Osorio et al. |
| 6,581,046 B1 | 6/2003 | Ahissar |
| 6,587,733 B1 | 7/2003 | Cross et al. |
| 6,591,128 B1 | 7/2003 | Wu et al. |
| 6,594,524 B2 | 7/2003 | Esteller et al. |
| 6,597,953 B2 | 7/2003 | Boling |
| 6,643,552 B2 | 11/2003 | Edell et al. |
| 6,671,544 B2 | 12/2003 | Baudino |
| 6,675,046 B2 | 1/2004 | Holsheimer |
| 6,687,538 B1 | 2/2004 | Hrdlicka et al. |
| 6,690,973 B2 | 2/2004 | Hill et al. |
| 6,708,064 B2 | 3/2004 | Rezai |
| 6,718,208 B2 | 4/2004 | Hill et al. |
| 6,718,211 B2 | 4/2004 | Smits |
| 6,741,893 B2 | 5/2004 | Smits |
| 6,745,079 B2 | 6/2004 | King |
| 6,757,970 B1 | 7/2004 | Kuzma et al. |
| 6,795,737 B2 | 9/2004 | Gielen et al. |
| 6,804,552 B2 | 10/2004 | Thompson et al. |
| 6,818,396 B1 | 11/2004 | Bloch et al. |
| 6,829,498 B2 | 12/2004 | Kipke et al. |
| 6,850,802 B2 | 2/2005 | Holsheimer |
| 6,871,098 B2 | 3/2005 | Nuttin et al. |
| 6,882,881 B1 | 4/2005 | Lesser et al. |
| 6,892,097 B2 | 5/2005 | Holsheimer |
| 6,892,438 B1 | 5/2005 | Hill et al. |
| 6,904,306 B1 | 6/2005 | Wu et al. |
| 6,909,920 B2 | 6/2005 | Lokhoff et al. |
| 6,920,359 B2 | 7/2005 | Meadows et al. |
| 6,928,320 B2 | 8/2005 | King |
| 6,950,706 B2 | 9/2005 | Rodriguez et al. |
| 6,950,709 B2 | 9/2005 | Baudino |
| 6,978,171 B2 | 12/2005 | Goetz et al. |
| 6,978,178 B2 | 12/2005 | Sommer et al. |
| 6,999,819 B2 | 2/2006 | Swoyer et al. |
| 7,006,859 B1 | 2/2006 | Osorio et al. |
| 7,010,351 B2 | 3/2006 | Firlik et al. |
| 7,010,356 B2 | 3/2006 | Jog et al. |
| 7,024,246 B2 | 4/2006 | Acosta et al. |
| 7,035,690 B2 | 4/2006 | Goetz |
| 7,047,082 B1 | 5/2006 | Schrom et al. |

(56) References Cited

U.S. PATENT DOCUMENTS

| | | | |
|---|---|---|---|
| 7,047,084 | B2 | 5/2006 | Erickson et al. |
| 7,050,856 | B2 | 5/2006 | Stypulkowski |
| 7,051,419 | B2 | 5/2006 | Schrom et al. |
| 7,061,240 | B2 | 6/2006 | Ham et al. |
| 7,063,767 | B1 | 6/2006 | Tyson et al. |
| 7,076,292 | B2 | 7/2006 | Forsberg |
| 7,077,822 | B1 | 7/2006 | Howard, III |
| 7,107,104 | B2 | 9/2006 | Keravel et al. |
| 7,133,718 | B2 | 11/2006 | Bakken et al. |
| 7,146,222 | B2 | 12/2006 | Boling |
| 7,151,961 | B1 | 12/2006 | Whitehurst et al. |
| 7,174,219 | B2 | 2/2007 | Wahlstrand et al. |
| 7,177,701 | B1 | 2/2007 | Pianca |
| 7,181,288 | B1 | 2/2007 | Rezai et al. |
| 7,184,829 | B2 | 2/2007 | Hill et al. |
| 7,187,978 | B2 | 3/2007 | Malek et al. |
| 7,191,016 | B2 | 3/2007 | Marshall et al. |
| 7,191,018 | B2 | 3/2007 | Gielen et al. |
| 7,198,626 | B2 * | 4/2007 | Lee .................. A61B 18/1482 606/114 |
| 7,200,439 | B2 | 4/2007 | Zdeblick et al. |
| 7,203,548 | B2 | 4/2007 | Whitehurst et al. |
| 7,204,798 | B2 | 4/2007 | Zdeblick et al. |
| 7,204,833 | B1 | 4/2007 | Osorio et al. |
| 7,209,787 | B2 | 4/2007 | DiLorenzo |
| 7,212,851 | B2 | 5/2007 | Donoghue et al. |
| 7,212,867 | B2 | 5/2007 | Van Venrooij et al. |
| 7,214,189 | B2 | 5/2007 | Zdeblick |
| 7,216,000 | B2 | 5/2007 | Sieracki et al. |
| 7,216,001 | B2 | 5/2007 | Hacker et al. |
| 7,231,256 | B2 | 6/2007 | Wahlstrand et al. |
| 7,236,822 | B2 | 6/2007 | Dobak, III |
| 7,242,984 | B2 | 7/2007 | DiLorenzo |
| 7,276,061 | B2 | 10/2007 | Schaer et al. |
| 7,280,867 | B2 | 10/2007 | Frei et al. |
| 7,282,030 | B2 | 10/2007 | Frei et al. |
| 7,282,050 | B2 | 10/2007 | Starkebaum et al. |
| 7,286,878 | B2 | 10/2007 | Stypulkowski |
| 7,286,882 | B2 | 10/2007 | Cole |
| 7,288,066 | B2 | 10/2007 | Drew |
| 7,289,851 | B2 | 10/2007 | Gunderson et al. |
| 7,289,852 | B2 | 10/2007 | Helfinstine et al. |
| 7,295,880 | B2 | 11/2007 | Gielen |
| 7,298,143 | B2 | 11/2007 | Jaermann et al. |
| 7,307,223 | B2 | 12/2007 | Tyson et al. |
| 7,313,430 | B2 | 12/2007 | Urquhart et al. |
| 7,313,440 | B2 | 12/2007 | Miesel |
| 7,315,759 | B2 | 1/2008 | Markowitz et al. |
| 7,317,947 | B2 | 1/2008 | Wahlstrand et al. |
| 7,317,948 | B1 | 1/2008 | King et al. |
| 7,319,899 | B2 | 1/2008 | Keizer |
| 7,319,904 | B2 | 1/2008 | Cross et al. |
| 7,321,798 | B2 | 1/2008 | Muhlenberg et al. |
| 7,321,837 | B2 | 1/2008 | Osorio et al. |
| 7,322,832 | B2 | 1/2008 | Kronich et al. |
| 7,328,057 | B2 | 2/2008 | Freas et al. |
| 7,328,068 | B2 | 2/2008 | Spinelli et al. |
| 7,328,069 | B2 | 2/2008 | Gerber |
| 7,330,760 | B2 | 2/2008 | Heruth et al. |
| 7,337,010 | B2 | 2/2008 | Howard et al. |
| 7,343,206 | B2 | 3/2008 | Sage et al. |
| 7,346,395 | B2 | 3/2008 | Lozano et al. |
| 7,356,369 | B2 | 4/2008 | Phillips et al. |
| 7,359,837 | B2 | 4/2008 | Drew |
| 7,366,572 | B2 | 4/2008 | Heruth et al. |
| 7,367,956 | B2 | 5/2008 | King |
| 7,369,891 | B2 | 5/2008 | Augustijn et al. |
| 7,369,893 | B2 | 5/2008 | Gunderson |
| 7,369,894 | B2 | 5/2008 | Gerber |
| 7,385,443 | B1 | 6/2008 | Denison |
| 7,388,378 | B2 | 6/2008 | Gray et al. |
| 7,389,147 | B2 | 6/2008 | Wahlstrand et al. |
| 7,390,311 | B2 | 6/2008 | Hildebrand et al. |
| 7,391,257 | B1 | 6/2008 | Denison et al. |
| 7,392,089 | B2 | 6/2008 | Wahlstrand et al. |
| 7,395,113 | B2 | 7/2008 | Heruth et al. |
| 7,400,927 | B1 | 7/2008 | Litvin |
| 7,403,820 | B2 | 7/2008 | DiLorenzo |
| 7,406,351 | B2 | 7/2008 | Wesselink |
| 7,418,292 | B2 | 8/2008 | Shafer |
| 7,421,297 | B2 | 9/2008 | Giftakis et al. |
| 7,427,280 | B2 | 9/2008 | Gerber |
| 7,429,938 | B1 | 9/2008 | Corndorf |
| 7,433,734 | B2 | 10/2008 | King |
| 7,442,183 | B2 | 10/2008 | Baudino et al. |
| 7,447,545 | B2 | 11/2008 | Heruth et al. |
| 7,450,996 | B2 | 11/2008 | MacDonald et al. |
| 7,463,917 | B2 | 12/2008 | Martinez |
| 7,463,928 | B2 | 12/2008 | Lee et al. |
| 7,474,247 | B1 | 1/2009 | Heinks et al. |
| 7,479,910 | B1 | 1/2009 | Heinks et al. |
| 7,483,748 | B2 | 1/2009 | Torgerson et al. |
| 7,489,966 | B2 | 2/2009 | Leinders et al. |
| 7,489,970 | B2 | 2/2009 | Lee et al. |
| 7,491,181 | B2 | 2/2009 | Heruth et al. |
| 7,497,844 | B2 | 3/2009 | Spear et al. |
| 7,497,863 | B2 | 3/2009 | Solar et al. |
| 7,502,217 | B2 | 3/2009 | Zhao et al. |
| 7,505,815 | B2 | 3/2009 | Lee et al. |
| 7,505,869 | B2 | 3/2009 | Hartlaub |
| 7,515,961 | B2 | 4/2009 | Germanson et al. |
| 7,519,431 | B2 | 4/2009 | Goetz et al. |
| 7,519,432 | B2 | 4/2009 | Bolea et al. |
| 7,520,890 | B2 | 4/2009 | Phillips |
| 7,526,339 | B2 | 4/2009 | Lahti et al. |
| 7,526,340 | B2 | 4/2009 | Drew |
| 7,526,341 | B2 | 4/2009 | Goetz et al. |
| 7,529,582 | B1 | 5/2009 | DiLorenzo |
| 7,529,586 | B2 | 5/2009 | Wahlstrand et al. |
| 7,542,803 | B2 | 6/2009 | Heruth et al. |
| 7,546,164 | B2 | 6/2009 | King |
| 7,546,166 | B2 | 6/2009 | Michels et al. |
| 7,548,775 | B2 | 6/2009 | Kipke et al. |
| 7,548,786 | B2 | 6/2009 | Lee et al. |
| 7,551,951 | B1 | 6/2009 | Osorio et al. |
| 7,551,960 | B2 | 6/2009 | Forsberg et al. |
| 7,555,345 | B2 | 6/2009 | Wahlstrand et al. |
| 7,561,921 | B2 | 7/2009 | Phillips et al. |
| 7,563,141 | B2 | 7/2009 | Alexander et al. |
| 7,563,541 | B2 | 7/2009 | Howard et al. |
| 7,578,819 | B2 | 8/2009 | Bleich et al. |
| 7,580,756 | B2 | 8/2009 | Schulte et al. |
| 7,582,387 | B2 | 9/2009 | Howard et al. |
| 7,590,451 | B2 | 9/2009 | Tronnes et al. |
| 7,590,453 | B2 | 9/2009 | Heruth et al. |
| 7,590,455 | B2 | 9/2009 | Heruth et al. |
| 7,591,970 | B2 | 9/2009 | Olson |
| 7,594,828 | B2 | 9/2009 | Alexander et al. |
| 7,594,889 | B2 | 9/2009 | St. Ores et al. |
| 7,596,399 | B2 | 9/2009 | Singhal et al. |
| 7,596,408 | B2 | 9/2009 | Singhal et al. |
| 7,596,415 | B2 | 9/2009 | Brabec et al. |
| 7,599,730 | B2 | 10/2009 | Hunter et al. |
| 7,603,161 | B2 | 10/2009 | Wurmfeld et al. |
| 7,603,177 | B2 | 10/2009 | Sieracki et al. |
| 7,604,629 | B2 | 10/2009 | Gerber et al. |
| 7,604,644 | B2 | 10/2009 | Schulte et al. |
| 7,608,458 | B2 | 10/2009 | Soykan et al. |
| 7,610,083 | B2 | 10/2009 | Drew et al. |
| 7,611,483 | B2 | 11/2009 | Gerber et al. |
| 7,614,743 | B2 | 11/2009 | Geiger |
| 7,615,015 | B2 | 11/2009 | Coleman |
| 7,616,998 | B2 | 11/2009 | Nuttin et al. |
| 7,617,002 | B2 | 11/2009 | Goetz |
| 7,620,454 | B2 | 11/2009 | Dinsmoor et al. |
| 7,622,303 | B2 | 11/2009 | Soykan et al. |
| 7,622,988 | B2 | 11/2009 | Denison et al. |
| 7,623,053 | B2 | 11/2009 | Terry et al. |
| 7,623,918 | B2 | 11/2009 | Goetz |
| 7,623,919 | B2 | 11/2009 | Goetz et al. |
| 7,623,923 | B2 | 11/2009 | Gerber et al. |
| 7,623,930 | B2 | 11/2009 | Zeijlemaker et al. |
| 7,624,293 | B2 | 11/2009 | Osorio et al. |
| 7,628,780 | B2 | 12/2009 | Bonner et al. |

(56) References Cited

U.S. PATENT DOCUMENTS

| | | |
|---|---|---|
| 7,631,415 B2 | 12/2009 | Phillips et al. |
| 7,632,225 B2 | 12/2009 | Stypulkowski |
| 7,635,541 B2 | 12/2009 | Scott et al. |
| 7,637,867 B2 | 12/2009 | Zdeblick |
| 7,640,059 B2 | 12/2009 | Forsberg et al. |
| 7,640,060 B2 | 12/2009 | Zdeblick |
| 7,641,992 B2 | 1/2010 | Howard et al. |
| 7,642,013 B2 | 1/2010 | Howard et al. |
| 7,647,111 B2 | 1/2010 | Ries et al. |
| 7,647,116 B2 | 1/2010 | Bauhahn |
| 7,647,117 B2 | 1/2010 | Bauhahn |
| 7,647,121 B2 | 1/2010 | Wahlstrand et al. |
| 7,650,291 B2 | 1/2010 | Rosenfeld et al. |
| 7,653,433 B2 | 1/2010 | Lozano et al. |
| 7,657,318 B2 | 2/2010 | King et al. |
| 7,657,319 B2 | 2/2010 | Goetz et al. |
| 7,660,620 B2 | 2/2010 | Zeijlemaker et al. |
| 7,660,630 B2 | 2/2010 | Dudding et al. |
| 7,662,140 B2 | 2/2010 | Heruth et al. |
| 7,662,509 B2 | 2/2010 | Howard et al. |
| 7,663,066 B2 | 2/2010 | Tyson et al. |
| 7,664,551 B2 | 2/2010 | Cigaina |
| 7,664,552 B2 | 2/2010 | Wahlstrand et al. |
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |
| 7,682,355 B2 | 3/2010 | Gerber et al. |
| 7,682,745 B2 | 3/2010 | Howard et al. |
| 7,684,860 B2 | 3/2010 | Wahlstrand et al. |
| 7,684,866 B2 | 3/2010 | Fowler et al. |
| 7,684,873 B2 | 3/2010 | Gerber |
| 7,689,289 B2 | 3/2010 | King |
| 7,697,972 B2 | 4/2010 | Verard et al. |
| 7,697,995 B2 | 4/2010 | Cross et al. |
| 7,706,124 B2 | 4/2010 | Zhao et al. |
| 7,706,889 B2 | 4/2010 | Gerber et al. |
| 7,711,421 B2 | 5/2010 | Shafer et al. |
| 7,711,428 B2 | 5/2010 | Janzig et al. |
| 7,711,436 B2 | 5/2010 | Stone |
| 7,713,194 B2 | 5/2010 | Zdeblick |
| 7,713,195 B2 | 5/2010 | Zdeblick |
| 7,720,548 B2 | 5/2010 | King |
| 7,729,768 B2 | 6/2010 | White et al. |
| 7,729,780 B2 | 6/2010 | Vardiman |
| 7,738,958 B2 | 6/2010 | Zdeblick et al. |
| 7,742,823 B2 | 6/2010 | King et al. |
| 7,756,588 B2 | 7/2010 | Jog et al. |
| 7,765,012 B2 | 7/2010 | Gerber |
| 7,769,472 B2 | 8/2010 | Gerber |
| 7,797,029 B2 | 9/2010 | Gibson et al. |
| 7,822,482 B2 | 10/2010 | Gerber |
| 7,822,483 B2 | 10/2010 | Stone et al. |
| 7,853,303 B2 | 12/2010 | Nikumb et al. |
| 7,877,149 B2 | 1/2011 | Zdeblick |
| 7,899,539 B2 | 3/2011 | Whitehurst et al. |
| 7,925,329 B2 | 4/2011 | Zdeblick et al. |
| 7,930,035 B2 | 4/2011 | Dilorenzo |
| 7,935,056 B2 | 5/2011 | Zdeblick |
| 7,941,202 B2 | 5/2011 | Hetke et al. |
| 7,945,329 B2 | 5/2011 | Bedenbaugh |
| 7,945,336 B2 | 5/2011 | Sauter-Starace et al. |
| 7,969,161 B2 | 6/2011 | Behzadi et al. |
| 7,974,705 B2 | 7/2011 | Zdeblick et al. |
| 7,978,064 B2 | 7/2011 | Zdeblick et al. |
| 7,979,105 B2 | 7/2011 | Kipke et al. |
| 7,983,751 B2 | 7/2011 | Zdeblick et al. |
| 7,991,481 B2 | 8/2011 | Benabid et al. |
| 8,000,794 B2 | 8/2011 | Lozano |
| 8,000,808 B2 | 8/2011 | Hegland et al. |
| 8,010,202 B2 | 8/2011 | Shah et al. |
| 8,024,022 B2 | 9/2011 | Schulman et al. |
| 8,032,224 B2 | 10/2011 | Miesel et al. |
| 8,036,737 B2 | 10/2011 | Goetz et al. |
| 8,036,743 B2 | 10/2011 | Savage et al. |
| 8,036,748 B2 | 10/2011 | Zdeblick et al. |
| 8,055,334 B2 | 11/2011 | Savage et al. |
| 8,055,353 B2 | 11/2011 | Kreidler et al. |
| 8,090,450 B2 | 1/2012 | Swoyer et al. |
| 8,099,170 B2 | 1/2012 | Jensen et al. |
| 8,108,049 B2 | 1/2012 | King |
| 8,114,021 B2 | 2/2012 | Robertson et al. |
| 8,115,618 B2 | 2/2012 | Robertson et al. |
| 8,121,687 B2 | 2/2012 | Jensen et al. |
| 8,121,702 B2 | 2/2012 | King |
| 8,123,684 B2 | 2/2012 | Zdeblick |
| 8,170,676 B2 | 5/2012 | Greenberg et al. |
| 8,171,621 B2 | 5/2012 | Swanson et al. |
| 8,172,762 B2 | 5/2012 | Robertson |
| 8,187,161 B2 | 5/2012 | Li et al. |
| 8,195,308 B2 | 6/2012 | Frank et al. |
| 8,204,586 B2 | 6/2012 | Zdeblick |
| 8,224,417 B2 | 7/2012 | Vetter |
| 8,224,462 B2 | 7/2012 | Westlund et al. |
| 8,244,377 B1 | 8/2012 | Pianca et al. |
| 8,258,962 B2 | 9/2012 | Robertson et al. |
| 8,261,428 B2 | 9/2012 | Fang et al. |
| 8,271,094 B1 | 9/2012 | Moffitt et al. |
| 8,280,514 B2 | 10/2012 | Lozano et al. |
| 8,295,943 B2 | 10/2012 | Eggen et al. |
| 8,315,686 B2 | 11/2012 | Llinas et al. |
| 8,321,025 B2 | 11/2012 | Bedenbaugh |
| 8,332,020 B2 | 12/2012 | Zdeblick |
| 8,332,046 B2 | 12/2012 | Anderson et al. |
| 8,355,768 B2 | 1/2013 | Masmanidis et al. |
| 8,374,703 B2 | 2/2013 | Imran |
| 8,412,347 B2 | 4/2013 | Zdeblick |
| 8,463,353 B2 | 6/2013 | Seymour |
| 8,463,398 B2 | 6/2013 | Jackson et al. |
| 8,467,877 B2 | 6/2013 | Imran |
| 8,473,061 B2 | 6/2013 | Moffitt et al. |
| 8,473,069 B2 | 6/2013 | Bi et al. |
| 8,489,203 B2 | 7/2013 | Ortmann |
| 8,509,872 B2 | 8/2013 | Lee et al. |
| 8,509,876 B2 | 8/2013 | Karmarkar |
| 8,509,920 B2 | 8/2013 | Wahlstrand et al. |
| 8,560,085 B2 | 10/2013 | Moffitt et al. |
| 8,565,894 B2 | 10/2013 | Vetter et al. |
| 8,571,665 B2 | 10/2013 | Moffitt et al. |
| 8,583,253 B1 | 11/2013 | Shi et al. |
| 8,620,452 B2 | 12/2013 | King et al. |
| 8,626,312 B2 | 1/2014 | King et al. |
| 8,634,934 B2 | 1/2014 | Kokones et al. |
| 8,644,903 B1 | 2/2014 | Osa et al. |
| 8,649,879 B2 | 2/2014 | Digiore et al. |
| 8,666,509 B2 | 3/2014 | Howard et al. |
| 8,694,105 B2 | 4/2014 | Martens et al. |
| 8,694,123 B2 | 4/2014 | Wahlstrand et al. |
| 8,694,127 B2 | 4/2014 | Pianca et al. |
| 8,731,673 B2 | 5/2014 | Vetter et al. |
| 8,738,154 B2 | 5/2014 | Zdeblick et al. |
| 8,744,596 B2 | 6/2014 | Howard |
| 8,755,906 B2 | 6/2014 | Moffitt et al. |
| 8,762,065 B2 | 6/2014 | Dilorenzo |
| 8,774,891 B1 | 7/2014 | Osa et al. |
| 8,788,056 B2 | 7/2014 | King et al. |
| 8,788,063 B2 | 7/2014 | Chen |
| 8,788,064 B2 | 7/2014 | Mercanzini et al. |
| 8,792,993 B2 | 7/2014 | Pianca et al. |
| 8,800,140 B2 | 8/2014 | Hetke et al. |
| 8,825,175 B2 | 9/2014 | King |
| 8,831,739 B2 | 9/2014 | McCreery et al. |
| 8,831,742 B2 | 9/2014 | Pianca et al. |
| 8,849,369 B2 | 9/2014 | Cogan et al. |
| 8,849,415 B2 | 9/2014 | Bedenbaugh |
| 8,862,242 B2 | 10/2014 | Pianca |
| 8,874,232 B2 | 10/2014 | Chen |
| 8,875,391 B2 | 11/2014 | Pianca et al. |
| 8,897,891 B2 | 11/2014 | Romero |
| 8,923,982 B2 | 12/2014 | Howard |
| 8,934,965 B2 | 1/2015 | Rogers et al. |
| 8,934,980 B2 | 1/2015 | Pless et al. |

(56) References Cited

U.S. PATENT DOCUMENTS

| | | |
|---|---|---|
| 8,938,300 B2 | 1/2015 | Rosero |
| 8,938,308 B2 | 1/2015 | Meadows |
| 8,958,862 B2 | 2/2015 | Hetke et al. |
| 8,968,331 B1 | 3/2015 | Sochor |
| 8,977,335 B2 | 3/2015 | Putz |
| 8,977,367 B2 | 3/2015 | Elahi et al. |
| 8,989,864 B2 | 3/2015 | Funderburk et al. |
| 9,008,747 B2 | 4/2015 | Seymour et al. |
| 9,014,796 B2 | 4/2015 | Kipke et al. |
| 9,044,590 B2 | 6/2015 | Greenberg et al. |
| 9,061,134 B2 | 6/2015 | Askin et al. |
| 9,079,013 B2 | 7/2015 | Digiore et al. |
| 9,089,689 B2 | 7/2015 | Govea |
| 9,089,690 B2 | 7/2015 | Greenberg et al. |
| 9,095,267 B2 | 8/2015 | Halpern et al. |
| 9,149,630 B2 | 10/2015 | Howard et al. |
| 9,211,401 B2 | 12/2015 | Frewin et al. |
| 9,211,402 B2 | 12/2015 | Moffitt et al. |
| 9,220,897 B2 | 12/2015 | Perryman et al. |
| 9,227,050 B2 | 1/2016 | Romero |
| 9,248,272 B2 | 2/2016 | Romero |
| 9,248,275 B2 | 2/2016 | Digiore et al. |
| 9,265,465 B2 | 2/2016 | Najafi et al. |
| 9,265,928 B2 | 2/2016 | Pellinen et al. |
| 9,283,375 B2 | 3/2016 | Moffitt et al. |
| 9,289,151 B2 | 3/2016 | Kipke et al. |
| 9,289,596 B2 | 3/2016 | Leven |
| 9,295,830 B2 | 3/2016 | Pianca |
| 9,314,614 B2 | 4/2016 | Bedenbaugh |
| 9,358,398 B2 | 6/2016 | Moffitt et al. |
| 9,364,659 B1 | 6/2016 | Rao |
| 9,381,347 B2 | 7/2016 | Howard et al. |
| 9,381,348 B2 | 7/2016 | Romero et al. |
| 9,381,356 B2 | 7/2016 | Parker et al. |
| 9,399,128 B2 | 7/2016 | Tooker et al. |
| 9,427,567 B2 | 8/2016 | Romero |
| 9,474,895 B2 | 10/2016 | Digiore et al. |
| 9,498,620 B2 | 11/2016 | Romero et al. |
| 9,517,020 B2 | 12/2016 | Shacham-Diamand et al. |
| 9,592,377 B2 | 3/2017 | Greenberg et al. |
| 9,604,051 B2 | 3/2017 | Vetter et al. |
| 9,662,494 B2 | 5/2017 | Young |
| 9,700,715 B2 | 7/2017 | Dou |
| 9,743,878 B2 | 8/2017 | Drew |
| 9,775,983 B2 | 10/2017 | Digiore et al. |
| 9,775,988 B2 | 10/2017 | Govea et al. |
| 9,827,413 B2 | 11/2017 | Barker et al. |
| 9,833,611 B2 | 12/2017 | Govea et al. |
| 9,855,428 B2 | 1/2018 | Henry et al. |
| 9,861,288 B2 | 1/2018 | Ma et al. |
| 9,925,368 B2 | 3/2018 | Ryu et al. |
| 10,046,165 B2 | 8/2018 | Frewin et al. |
| 2001/0051802 A1* | 12/2001 | Woloszko .......... A61B 18/1206 606/41 |
| 2001/0051819 A1 | 12/2001 | Fischell et al. |
| 2002/0062143 A1 | 5/2002 | Baudino et al. |
| 2002/0116042 A1 | 8/2002 | Boling |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0060822 A1 | 3/2003 | Schaer et al. |
| 2003/0083724 A1 | 5/2003 | Jog et al. |
| 2003/0100823 A1 | 5/2003 | Kipke et al. |
| 2003/0135253 A1 | 7/2003 | Kokones et al. |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0039434 A1 | 2/2004 | Schrom et al. |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0193021 A1 | 9/2004 | Zdeblick et al. |
| 2004/0215288 A1 | 10/2004 | Lee et al. |
| 2004/0220637 A1 | 11/2004 | Zdeblick et al. |
| 2004/0225335 A1 | 11/2004 | Whitehurst et al. |
| 2004/0243011 A1 | 12/2004 | Plaza |
| 2004/0249417 A1 | 12/2004 | Ransbury et al. |
| 2004/0254483 A1 | 12/2004 | Zdeblick et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0021103 A1 | 1/2005 | DiLorenzo |
| 2005/0027284 A1 | 2/2005 | Lozano et al. |
| 2005/0033136 A1 | 2/2005 | Govari et al. |
| 2005/0038489 A1 | 2/2005 | Grill |
| 2005/0049655 A1 | 3/2005 | Boveja et al. |
| 2005/0070971 A1 | 3/2005 | Fowler et al. |
| 2005/0075681 A1 | 4/2005 | Rezai et al. |
| 2005/0113882 A1 | 5/2005 | Cameron et al. |
| 2005/0137647 A1 | 6/2005 | Wallace et al. |
| 2005/0143790 A1 | 6/2005 | Kipke et al. |
| 2005/0154425 A1 | 7/2005 | Boveja et al. |
| 2005/0171522 A1* | 8/2005 | Christopherson .. A61B 18/1477 606/34 |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0222642 A1 | 10/2005 | Przybyszewski et al. |
| 2005/0240242 A1 | 10/2005 | DiLorenzo |
| 2005/0245988 A1 | 11/2005 | Miesel |
| 2006/0004422 A1 | 1/2006 | De Ridder |
| 2006/0030897 A1 | 2/2006 | Gilmer et al. |
| 2006/0041295 A1 | 2/2006 | Osypka |
| 2006/0049957 A1 | 3/2006 | Surgenor et al. |
| 2006/0058588 A1 | 3/2006 | Zdeblick |
| 2006/0058727 A1 | 3/2006 | Bernabei |
| 2006/0058855 A1 | 3/2006 | Gill |
| 2006/0084965 A1* | 4/2006 | Young .................. A61B 18/148 606/41 |
| 2006/0095029 A1* | 5/2006 | Young .................. A61B 18/148 606/41 |
| 2006/0095105 A1 | 5/2006 | Jog et al. |
| 2006/0116581 A1 | 6/2006 | Zdeblick et al. |
| 2006/0129203 A1 | 6/2006 | Garabedian et al. |
| 2006/0135877 A1 | 6/2006 | Giftakis et al. |
| 2006/0149336 A1 | 7/2006 | Meadows |
| 2006/0149337 A1 | 7/2006 | John |
| 2006/0167497 A1 | 7/2006 | Armstrong et al. |
| 2006/0173263 A1 | 8/2006 | He et al. |
| 2006/0173510 A1 | 8/2006 | Besio et al. |
| 2006/0178709 A1 | 8/2006 | Foster et al. |
| 2006/0184060 A1 | 8/2006 | Belalcazar et al. |
| 2006/0195154 A1 | 8/2006 | Jaax et al. |
| 2006/0200206 A1 | 9/2006 | Firlik et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0276866 A1 | 12/2006 | McCreery |
| 2006/0282014 A1 | 12/2006 | Kipke et al. |
| 2006/0293720 A1 | 12/2006 | DiLorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |

(56) References Cited

U.S. PATENT DOCUMENTS

| | | |
|---|---|---|
| 2007/0106143 A1 | 5/2007 | Flaherty |
| 2007/0123765 A1 | 5/2007 | Hetke et al. |
| 2007/0123944 A1 | 5/2007 | Zdeblick |
| 2007/0135721 A1 | 6/2007 | Zdeblick |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173896 A1 | 7/2007 | Zdeblick |
| 2007/0173897 A1 | 7/2007 | Zdeblick |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0179569 A1 | 8/2007 | Zdeblick |
| 2007/0185537 A1 | 8/2007 | Zdeblick |
| 2007/0185544 A1 | 8/2007 | Dawant et al. |
| 2007/0185548 A1 | 8/2007 | Zdeblick |
| 2007/0185549 A1 | 8/2007 | Zdeblick |
| 2007/0197892 A1 | 8/2007 | Shen et al. |
| 2007/0203537 A1 | 8/2007 | Goetz et al. |
| 2007/0203546 A1 | 8/2007 | Stone et al. |
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0219591 A1 | 9/2007 | Zdeblick et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2007/0293908 A1 | 12/2007 | Cowan et al. |
| 2008/0021514 A1 | 1/2008 | Pless |
| 2008/0021517 A1 | 1/2008 | Dietrich |
| 2008/0027289 A1 | 1/2008 | Zdeblick |
| 2008/0027487 A1 | 1/2008 | Patel et al. |
| 2008/0027503 A1 | 1/2008 | Marrosu et al. |
| 2008/0027504 A1 | 1/2008 | Bedenbaugh |
| 2008/0027514 A1 | 1/2008 | Demulling et al. |
| 2008/0027540 A1 | 1/2008 | Cumming |
| 2008/0039895 A1 | 2/2008 | Fowler et al. |
| 2008/0046012 A1 | 2/2008 | Covalin et al. |
| 2008/0046013 A1 | 2/2008 | Lozano |
| 2008/0058630 A1 | 3/2008 | Robertson |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0103578 A1 | 5/2008 | Gerber |
| 2008/0114417 A1 | 5/2008 | Leyde |
| 2008/0119900 A1 | 5/2008 | DiLorenzo |
| 2008/0139870 A1 | 6/2008 | Gliner et al. |
| 2008/0140152 A1 | 6/2008 | Imran et al. |
| 2008/0154328 A1 | 6/2008 | Thompson et al. |
| 2008/0154331 A1 | 6/2008 | John et al. |
| 2008/0154340 A1 | 6/2008 | Goetz et al. |
| 2008/0161881 A1 | 7/2008 | Firlik et al. |
| 2008/0161896 A1* | 7/2008 | Sauter-Starace ... A61B 5/04001 607/116 |
| 2008/0172103 A1 | 7/2008 | Kao et al. |
| 2008/0177196 A1 | 7/2008 | Burdick et al. |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1 | 8/2008 | Vetter et al. |
| 2008/0208287 A1 | 8/2008 | Palermo et al. |
| 2008/0215125 A1 | 9/2008 | Farah et al. |
| 2008/0221642 A1 | 9/2008 | Humayun et al. |
| 2008/0242976 A1 | 10/2008 | Robertson et al. |
| 2008/0255439 A1 | 10/2008 | Tang et al. |
| 2008/0255629 A1 | 10/2008 | Jenson et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0275526 A1 | 11/2008 | Lozano |
| 2008/0284599 A1 | 11/2008 | Zdeblick et al. |
| 2008/0294218 A1 | 11/2008 | Savage et al. |
| 2008/0300652 A1 | 12/2008 | Lim et al. |
| 2008/0306394 A1 | 12/2008 | Zdeblick et al. |
| 2008/0312726 A1 | 12/2008 | Frank et al. |
| 2008/0316020 A1 | 12/2008 | Robertson et al. |
| 2009/0027504 A1 | 1/2009 | Lim et al. |
| 2009/0062879 A1 | 3/2009 | Li et al. |
| 2009/0082645 A1 | 3/2009 | Hafezi et al. |
| 2009/0105784 A1 | 4/2009 | Massoud-Ansari et al. |
| 2009/0118806 A1 | 5/2009 | Vetter et al. |
| 2009/0132042 A1 | 5/2009 | Hetke et al. |
| 2009/0171416 A1 | 7/2009 | Firlik et al. |
| 2009/0177144 A1 | 7/2009 | Masmanidis et al. |
| 2009/0187196 A1 | 7/2009 | Vetter |
| 2009/0204183 A1 | 8/2009 | Kreidler et al. |
| 2009/0240314 A1 | 9/2009 | Kong et al. |
| 2009/0253977 A1 | 10/2009 | Kipke et al. |
| 2009/0256702 A1 | 10/2009 | Robertson et al. |
| 2009/0292325 A1 | 11/2009 | Cederna et al. |
| 2009/0299174 A1 | 12/2009 | Wright et al. |
| 2009/0306728 A1 | 12/2009 | Wright et al. |
| 2009/0306729 A1 | 12/2009 | Doerr |
| 2009/0312770 A1 | 12/2009 | Kozai et al. |
| 2009/0318824 A1 | 12/2009 | Nishida et al. |
| 2009/0325424 A1 | 12/2009 | Aarts et al. |
| 2010/0014541 A1 | 1/2010 | Harriman |
| 2010/0015274 A1 | 1/2010 | Fill |
| 2010/0030298 A1 | 2/2010 | Martens et al. |
| 2010/0036468 A1 | 2/2010 | Decre et al. |
| 2010/0047376 A1 | 2/2010 | Imbeau et al. |
| 2010/0069717 A1 | 3/2010 | Hafezi et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0106178 A1 | 4/2010 | Obermiller et al. |
| 2010/0114193 A1 | 5/2010 | Lozano et al. |
| 2010/0114234 A1 | 5/2010 | Zdeblick |
| 2010/0114250 A1 | 5/2010 | Zdeblick |
| 2010/0130844 A1 | 5/2010 | Williams et al. |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0198315 A1 | 8/2010 | Martens et al. |
| 2010/0249883 A1 | 9/2010 | Zdeblick |
| 2010/0274305 A1 | 10/2010 | Gliner et al. |
| 2010/0292602 A1 | 11/2010 | Worrell et al. |
| 2010/0298908 A1 | 11/2010 | Vardiman |
| 2010/0298917 A1 | 11/2010 | Vardiman |
| 2010/0298918 A1 | 11/2010 | Vardiman |
| 2010/0312188 A1 | 12/2010 | Robertson et al. |
| 2010/0312228 A1 | 12/2010 | Zdeblick et al. |
| 2010/0318163 A1 | 12/2010 | Zdeblick |
| 2010/0331807 A1 | 12/2010 | Whitehurst et al. |
| 2011/0001488 A1 | 1/2011 | Behzadi et al. |
| 2011/0022124 A1 | 1/2011 | Zdeblick et al. |
| 2011/0034964 A1 | 2/2011 | Bi et al. |
| 2011/0034970 A1 | 2/2011 | Barker |
| 2011/0040203 A1 | 2/2011 | Savage et al. |
| 2011/0071766 A1 | 3/2011 | Dolan et al. |
| 2011/0130809 A1 | 6/2011 | Zdeblick |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0196454 A1 | 8/2011 | Strand et al. |
| 2011/0208225 A1 | 8/2011 | Martens et al. |
| 2011/0213382 A1 | 9/2011 | Decre et al. |
| 2011/0218417 A1 | 9/2011 | Boogaard et al. |
| 2011/0224757 A1 | 9/2011 | Zdeblick et al. |
| 2011/0224765 A1 | 9/2011 | Harberts et al. |
| 2011/0224766 A1 | 9/2011 | Tol et al. |

(56) References Cited

U.S. PATENT DOCUMENTS

| | | |
|---|---|---|
| 2011/0282179 A1 | 11/2011 | Zdeblick |
| 2012/0004520 A1 | 1/2012 | Whitworth et al. |
| 2012/0004527 A1 | 1/2012 | Thompson et al. |
| 2012/0004716 A1 | 1/2012 | Langhammer et al. |
| 2012/0007734 A1 | 1/2012 | Berkman et al. |
| 2012/0022341 A1 | 1/2012 | Zdeblick |
| 2012/0035684 A1 | 2/2012 | Thompson et al. |
| 2012/0053344 A1 | 3/2012 | Lagos Gonzalez |
| 2012/0059444 A1 | 3/2012 | Pardoel et al. |
| 2012/0062379 A1 | 3/2012 | Hafezi et al. |
| 2012/0095355 A1 | 4/2012 | Zdeblick |
| 2012/0109262 A1 | 5/2012 | Martens |
| 2012/0109599 A1 | 5/2012 | Martens |
| 2012/0116188 A1 | 5/2012 | Frank et al. |
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0253442 A1 | 10/2012 | Gliner et al. |
| 2012/0277821 A1 | 11/2012 | Martens et al. |
| 2012/0296444 A1 | 11/2012 | Greenberg et al. |
| 2012/0302912 A1 | 11/2012 | Moffitt et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2012/0316630 A1 | 12/2012 | Firlik et al. |
| 2013/0009691 A1 | 1/2013 | Blanken et al. |
| 2013/0030366 A1 | 1/2013 | Robertson et al. |
| 2013/0046356 A1 | 2/2013 | Jensen et al. |
| 2013/0060102 A1 | 3/2013 | Zdeblick |
| 2013/0085361 A1* | 4/2013 | Mercanzini ........ A61B 5/04001 600/377 |
| 2013/0131754 A1 | 5/2013 | Sarvazyan |
| 2013/0144132 A1 | 6/2013 | Hafezi et al. |
| 2013/0172716 A1 | 7/2013 | Lozano et al. |
| 2013/0193950 A1 | 8/2013 | Hafezi et al. |
| 2013/0204318 A1 | 8/2013 | Young |
| 2013/0223028 A1 | 8/2013 | Arne et al. |
| 2013/0231188 A1 | 9/2013 | Berberich et al. |
| 2013/0282090 A1 | 10/2013 | Decre et al. |
| 2013/0345780 A1 | 12/2013 | Tabada et al. |
| 2013/0345789 A1 | 12/2013 | Havel et al. |
| 2014/0039578 A1 | 2/2014 | Whitehurst et al. |
| 2014/0066999 A1 | 3/2014 | Carcieri et al. |
| 2014/0200633 A1 | 7/2014 | Moffitt |
| 2014/0277284 A1 | 9/2014 | Chen et al. |
| 2015/0051678 A1 | 2/2015 | Reed et al. |
| 2015/0105774 A1 | 4/2015 | Lindquist et al. |
| 2015/0142090 A1 | 5/2015 | Duijsens et al. |
| 2015/0151111 A1 | 6/2015 | Pianca et al. |
| 2015/0209578 A1 | 7/2015 | Kast et al. |
| 2015/0246233 A1 | 9/2015 | Kaemmerer |
| 2015/0290452 A1 | 10/2015 | Kokones et al. |
| 2015/0335258 A1 | 11/2015 | Masmanidis |
| 2015/0355413 A1* | 12/2015 | Bhagavatula ........ A61B 5/0066 385/26 |
| 2015/0360023 A1 | 12/2015 | Howard et al. |
| 2016/0008592 A1 | 1/2016 | Romero et al. |
| 2016/0023003 A1 | 1/2016 | Perryman et al. |
| 2016/0074651 A1 | 3/2016 | Moffitt et al. |
| 2016/0144186 A1 | 5/2016 | Kaemmerer et al. |
| 2016/0228706 A1 | 8/2016 | Hershey et al. |
| 2016/0331953 A1 | 11/2016 | Reed et al. |
| 2016/0331975 A1 | 11/2016 | Henry et al. |
| 2016/0361535 A1 | 12/2016 | Perryman et al. |
| 2017/0007813 A1 | 1/2017 | Negi et al. |
| 2017/0049345 A1 | 2/2017 | Single |
| 2017/0136238 A1 | 5/2017 | Hartig et al. |
| 2017/0143982 A1 | 5/2017 | Mercanzini |
| 2017/0189700 A1 | 7/2017 | Moffitt et al. |
| 2017/0197086 A1 | 7/2017 | Howard et al. |
| 2017/0266432 A1 | 9/2017 | Seeley et al. |
| 2017/0296808 A1 | 10/2017 | Greenberg et al. |
| 2017/0361101 A1 | 12/2017 | Single |
| 2018/0185656 A1 | 7/2018 | Shepard et al. |

FOREIGN PATENT DOCUMENTS

| | | |
|---|---|---|
| CN | 201871104 U | 6/2011 |
| CN | 102274074 A | 12/2011 |
| CN | 102341036 A | 2/2012 |
| EP | 0 586 664 A1 | 3/1994 |
| EP | 0 677 743 | 10/1995 |
| EP | 0 743 839 | 11/1996 |
| EP | 0 892 654 | 1/1999 |
| EP | 0 895 483 | 2/1999 |
| EP | 0 959 942 | 12/1999 |
| EP | 1 048 319 | 11/2000 |
| EP | 1 062 973 | 12/2000 |
| EP | 1 102 607 | 5/2001 |
| EP | 1 257 320 | 11/2002 |
| EP | 1 446 189 | 8/2004 |
| EP | 1 514 576 | 3/2005 |
| EP | 1 750 798 | 2/2007 |
| EP | 1 890 764 | 2/2008 |
| EP | 1 931 419 | 6/2008 |
| EP | 1 985 579 | 10/2008 |
| EP | 1 993 665 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 144 665 A1 | 1/2010 |
| EP | 2 167 188 | 3/2010 |
| EP | 2 320 221 | 5/2011 |
| EP | 2 341 979 | 7/2011 |
| EP | 2 389 975 B1 | 11/2011 |
| EP | 2 456 513 A1 | 5/2012 |
| EP | 2 476 453 A1 | 7/2012 |
| EP | 2 542 303 A1 | 1/2013 |
| EP | 2 559 454 A1 | 2/2013 |
| EP | 2 604 313 | 6/2013 |
| EP | 2 618 889 | 7/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 664 354 B1 | 11/2013 |
| EP | 2 674 193 A1 | 12/2013 |
| EP | 2 862 595 B1 | 4/2015 |
| EP | 3 111 835 A1 | 1/2017 |
| EP | 3 231 476 A1 | 10/2017 |
| JP | 2005-052647 | 3/2005 |
| JP | 2012-179333 A | 9/2012 |
| WO | WO-98/10010 | 3/1998 |
| WO | WO-03/022354 | 3/2003 |
| WO | WO-03/028521 | 4/2003 |
| WO | WO-03/066152 | 8/2003 |
| WO | WO-03/066153 A2 | 8/2003 |
| WO | WO-03/066157 | 8/2003 |
| WO | WO-2004/043536 A1 | 5/2004 |
| WO | WO-2018/068013 A1 | 5/2004 |
| WO | WO-2004/045707 | 6/2004 |
| WO | WO-2005/002467 | 1/2005 |
| WO | WO-2005/067792 | 7/2005 |
| WO | WO-2005/112216 | 11/2005 |
| WO | WO-2006/104432 | 10/2006 |
| WO | WO-2007/002144 | 1/2007 |
| WO | WO-2007/009070 | 1/2007 |
| WO | WO-2007/011611 | 1/2007 |
| WO | WO-2007/025356 | 3/2007 |
| WO | WO-2007/028003 A2 | 3/2007 |
| WO | WO-2007/042999 | 4/2007 |
| WO | WO-2007/092330 | 8/2007 |
| WO | WO-2007/100428 | 9/2007 |
| WO | WO-2007/108718 | 9/2007 |
| WO | WO-2008/003318 | 1/2008 |
| WO | WO-2008/005478 | 1/2008 |
| WO | WO-2008/016881 | 2/2008 |
| WO | WO-2008/035285 | 3/2008 |
| WO | WO-2008/035344 | 3/2008 |

(56) References Cited

FOREIGN PATENT DOCUMENTS

| WO | WO-2008/051463 | 5/2008 |
|---|---|---|
| WO | WO-2008/064269 A2 | 5/2008 |
| WO | WO-2008/068759 | 6/2008 |
| WO | WO-2008/075294 | 6/2008 |
| WO | WO-2008/077440 | 7/2008 |
| WO | WO-2008/088897 | 7/2008 |
| WO | WO-2008/089726 | 7/2008 |
| WO | WO-2008/107822 | 9/2008 |
| WO | WO-2008/109298 | 9/2008 |
| WO | WO-2008/133616 | 11/2008 |
| WO | WO-2008/133683 | 11/2008 |
| WO | WO-2008/138305 | 11/2008 |
| WO | WO-2010/014686 | 2/2010 |
| WO | WO-2010/055421 | 5/2010 |
| WO | WO-2011/000791 A1 | 1/2011 |
| WO | WO-2011/115999 | 9/2011 |
| WO | WO-2013/014206 | 1/2013 |

OTHER PUBLICATIONS

US 8,469,885 B2, 06/2013, Hafezi et al. (withdrawn)
Extended European Search Report for EP Application No. 18208814.6 dated Mar. 28, 2019.
Final Office Action on U.S. Appl. No. 15/369,766 dated Feb. 7, 2019
International Preliminary Report on Patentability and Written Opinion for PCT/IB2017/050551 dated Aug. 16, 2018.
Notice of Allowance on U.S. Appl. No. 14/731,296 dated Aug. 15, 2018.
Notice of Allowance on U.S. Appl. No. 15/185,709 dated Nov. 9, 2018.
Notice of Allowance on U.S. Appl. No. 15/281,468 dated Jun. 1, 2018.
Notice of Allowance on U.S. Appl. No. 15/878,066 dated Oct. 3, 2018.
Notice of Allowance on U.S. Appl. No. 15/878,066 dated Dec. 5, 2018.
Office Action for CA Application No. 2,795,159 dated Dec. 18, 2018.
Office Action for Chinese Application No. 201580016170.1 dated Jan. 28, 2019.
Notice of Allowance for U.S. Appl. No. 15/369,766 dated Oct. 17, 2019 (12 pages).
Bucher et al., "Low-impedance thin-film polycrystalline silicon microelectrodes for extracellular stimulation and recording", Biosensors & Bioelectronics, vol. 14, 1999, pp. 639-649 (11 pages).
European Search Report on EP 16190439 dated Jul. 19, 2017 (2 pages).
Extended European Search Report on EP 19165102.5 dated Jul. 8, 2019 (7 pages).
Final Office Action on U.S. Appl. No. 16/015,625 dated Dec. 28, 2018 (13 pages).
Hosp et al., "Thin-film epidural microelectrode arrays for somatosensory and motor cortex mapping in rat", Journal of Neuroscience Methods, vol. 172, 2008, pp. 255-262 (8 pages).
International Search Report and Written Opinion of the International Searching Authority on PCT/IB2019/051635 dated Jun. 3, 2019 (13 pages).
International Search Report and Written Opinion of the International Searching Authority on PCT/IB2019/053275 dated Jul. 4, 2019 (12 pages).
Janders et al., "Novel Thin Film Titanium Nitride Micro-Electrodes With Excellent Charge Transfer Capability for Cell Stimulation and Sensing Applications", 18th Annual International Conference of the IEEE Engineering in Medicine and Biology Society, 1996, Amsterdam (3 pages).
Moxon et al., "Nanostructured Surface Modification of Ceramic-Based Microelectrodes to Enhance Biocompatibility for a Direct Brain-Machine Interface", IEEE Transactions on Biomedical Engineering, vol. 51, No. 6, Jun. 2004, pp. 881-889 (9 pages).

Non-Final Office Action on U.S. Appl. No. 15/369,766 dated May 31, 2019 (10 pages).
Non-Final Office Action on U.S. Appl. No. 16/015,625 dated Aug. 9, 2018 (14 pages).
Notice of Allowance on U.S. Appl. No. 15/185,709 dated Jun. 10, 2019 (2 pages).
Notice of Allowance on U.S. Appl. No. 15/185,709 dated Apr. 26, 2019 (5 pages).
Notice of Allowance on U.S. Appl. No. 15/281,468 dated Jul. 27, 2018 (2 pages).
Notice of Allowance on U.S. Appl. No. 16/015,625 dated Mar. 28, 2019 (8 pages).
Notice of Allowance on U.S. Appl. No. 16/015,625 dated May 8, 2019 (8 pages).
Notice of Reasons for Rejection on JP 2017-530450 dated Jul. 11, 2019 (4 pages).
Office Action on CN 201580016170.1 dated Jan. 28, 2019 (10 pages).
Ziaie et al., "A Single-Channel Implantable Microstimulator for Functional Neuromuscular Stimulation", IEEE Transactions on Biomedical Engineering, vol. 44, No. 10, Oct. 1997, pp. 909-920 (12 pages).
Cogan, S., et al. "Plasma-enhanced chemical vapor deposited silicon carbide as an implantable dielectric coating." Journal of Biomedical Materials Research Part A 67.3 (2003): 856-867.
Communication from the European Patent Office in Application No. 09795810.2 dated Sep. 14, 2011.
EIC Biomedical, "Thin-film Encapsulation for Neural Recording and Stimulation Electrodes", Silicon carbide and oxycarbide, Apr. 2008: pp. 1-2.
European Search Report for Appl. Serial No. 09803534.8 dated Jul. 21, 2011.
Fierce Medical Devices, "Medtronic Announces First U.S. Implant of World's Smallest, Minimally Invasive Cardiac Pacemaker", Feb. 20, 2014, pp. 1-3.
Gibney, "St. Jude places its Nanostim leadless pacemaker in a U.K. patient", Fierce Medical Devices, Jan. 27, 2014, pp. 1-3.
International Search Report and Written Opinion in PCT/US09/52077 dated Sep. 25, 2009.
International Search Report for PCT/IB2009/007715 dated Apr. 22, 2010.
Written Opinion of the International Search Authority for PCT/IB2009/07715 dated May 12, 2011.
Extended European Search Report for EP 19174013.3 dated Oct. 8, 2019 (7 pages).
U.S. Appl. No. 07/151,961, filed Feb. 3, 1988, Masahiko Okunuki et al.
U.S. Appl. No. 07/184,829, filed Apr. 22, 1988, Tsutsui et al.
Australian Patent Examination Report No. 1 dated Jan. 30, 2014 in corresponding Australian Application No. 2010326613, 2 pages.
Australian Patent Examination Report No. 1 dated Jan. 31, 2014 in corresponding Australian Application No. 2009315316, 3 pages.
Benabid, et al. "Combined (Thalamotomy and Stimulation) Stereotactic Surgery of the VIM Thalamic Nucleus for Bilateral Parkinson Disease", Proceedings of the Meeting of the American Society for Stereotactic and Functional Neurosurgery, Montreal 1987 Appl. Neurophysiol. 50: 344-346.
Canadian Office Action for Application No. 2,743,575 dated Sep. 25, 2014, 3 pages.
Decision of Rejection and Decision for Dismissal of Amendment in JP Patent Application No. 2011-543841 dated May 15, 2014.
Decision of Rejection for Japanese Appl. Ser. No. 2012-541491 dated Oct. 26, 2015.
English translation of Notice of Reasons for Rejection in JP application No. 2011-543841 dated Oct. 21, 2013.
European Communication and Search Report for Application No. 09795810.2 dated Sep. 25, 2013.
European Communication dated May 22, 2013 including search report for EP application No. 12198290.4-1652.
European Search Report for Appl. Ser. No. 09803534.8 dated Jul. 21, 2011.
European Search Report for Appl. Ser. No. 13169272.5 dated Aug. 30, 2013.

(56) References Cited

OTHER PUBLICATIONS

European Search Report for application No. EP 14172592 dated Aug. 28, 2014, 8 pages.
Examination Report for EP09795810.2 dated Jun. 22, 2012.
Examination Report from European Patent Office in 09 795 810.2 dated May 8, 2014.
Examination Report in AU Patent Application No. 2009276603 dated Mar. 3, 2014.
Examination report in AU Patent Application No. 2011234422 dated Feb. 11, 2014.
Examination Report in EP Patent Application No. 11 711 884.4 dated Mar. 28, 2014.
International Preliminary Report on Patentability for PCT/EP2010/068658 dated Jun. 5, 2012.
International Preliminary Report on Patentability for PCT/IB2009/007715 dated May 17, 2011.
International Preliminary Report on Patentability for PCT/US2009/052077 dated Feb. 1, 2011.
International Search Report and Written Opinion for PCT Appl. Ser. No. PCT/IB2015/053610 dated Jul. 20, 2015.
International Search Report and Written Opinion for PCT Appl. Ser. No. PCT/IB2015/056437 dated Nov. 5, 2015.
International Search Report and Written Opinion for PCT Appl. Ser. No. PCT/IB2015/056438 dated Nov. 5, 2015.
International Search Report and Written Opinion for PCT/EP2010/068658 dated Mar. 21, 2011.
International Search Report and Written Opinion in Application No. PCT/EP2011/055045 dated Jul. 18, 2011.
Notice of Allowance for U.S. Appl. No. 14/287,917 dated Apr. 15, 2015.
Notice of Allowance on U.S. Appl. No. 14/470,423 dated Jun. 15, 2016.
Notice of Allowance on U.S. Appl. No. 15/194,033 dated Oct. 27, 2016.
Notice of Reasons for Rejection for Japanese Patent Application No. 2011-543841 dated May 30, 2013.
Notice of Reasons for Rejection in JP Patent Application No. 2011-521276 dated Mar. 3, 2014.
Notice of Reasons for Rejection in JP Patent Application No. 2011-521276 dated May 30, 2013.
Notice of Reasons for Rejections for Japanese Patent Appl. Serial No. 2012-541491 dated Aug. 28, 2014, 8 pages.
Office Action for Canadian Appl. Ser. No. 2732309 dated Dec. 7, 2015.
Office Action for Canadian Appl. Ser. No. 2743575 dated Jan. 21, 2015 (4 pages).
Office Action for Canadian Appl. Ser. No. 2743575 dated Jun. 11, 2015.
Office Action for Canadian Appl. Ser. No. 2743575 dated Sep. 14, 2015.
Office Action for EPO Appl. Ser. No. 10787404.2 dated May 6, 2015.
Office Action for EPO Appl. Ser. No. 14172592.9 dated Aug. 20, 2015.
Office Action for European Application No. 10787404.2 dated Mar. 26, 2013.
Office Action for Japanese Appl. Ser. No. 2013-501857 dated Jun. 1, 2015.
Office Action for Japanese Appl. Ser. No. 2013-501857 dated Sep. 17, 2014.
Office Action on U.S. Appl. No. 14/731,296 dated Oct. 5, 2016.
Office Action on U.S. Appl. No. 14/945,952 dated Jul. 26, 2016.
Office Action on U.S. Appl. No. 15/194,033 dated Aug. 22, 2016.
Pollak, et al. "Effets de la Stimulation du Noyau Sous-Thalamique Dans La Maladie De Parkinson", Rev. Neurol (Paris),149, 3, 175-176. Mason, Paris, 1993.
Rousche, et al., "Flexible polyimide-based intracortical electrode arrays with bioactive capability," IEEE Transactions on Biomedical Engineering 48(3): 361-371 (Mar. 2001).
Second Notice of Reasons for Rejection for Japanese Application No. 2012-541491 dated Apr. 8, 2015.
Sepulveda et al., "Finite Element Analysis of Current Pathways with Implanted Electrodes", J. Biomed. Eng. 1983, vol. 5, pp. 41-48.
U.S. Corrected Notice of Allowability for U.S. Appl. No. 14/470,356 dated May 18, 2016.
U.S. Notice of Allowance for U.S. Appl. No. 14/287,917 dated Jul. 20, 2015.
U.S. Notice of Allowance for U.S. Appl. No. 14/309,491 dated May 11, 2016.
U.S. Notice of Allowance for U.S. Appl. No. 14/316,154 dated Apr. 20, 2015.
U.S. Notice of Allowance for U.S. Appl. No. 14/470,356 dated Apr. 13, 2016.
U.S. Notice of Allowance for U.S. Appl. No. 14/470,356 dated Mar. 18, 2016.
U.S. Notice of Allowance for U.S. Appl. No. 13/512,936 dated Feb. 20, 2014.
U.S. Notice of Allowance for U.S. Appl. No. 13/512,936 dated Nov. 25, 2013.
U.S. Notice of Allowance for U.S. Appl. No. 13/056,261 dated May 8, 2014.
U.S. Notice of Allowance in U.S. Appl. No. 13/128,821 dated Dec. 24, 2013.
U.S. Notice of Allowance in U.S. Appl. No. 13/128,821 dated Mar. 25, 2014.
U.S. Notice of Allowance on U.S. Appl. No. 13/638,435 dated Sep. 16, 2016.
U.S. Office Action for U.S. Appl. No. 13/128,821 dated Nov. 14, 2013.
U.S. Office Action for U.S. Appl. No. 13/638,435 dated Feb. 10, 2016.
U.S. Office Action for U.S. Appl. No. 13/638,435 dated Jun. 30, 2015.
U.S. Office Action for U.S. Appl. No. 13/638,435 dated Mar. 12, 2015.
U.S. Office Action for U.S. Appl. No. 14/309,491 dated Jul. 28, 2015.
U.S. Office Action for U.S. Appl. No. 14/309,491 dated Mar. 3, 2016.
U.S. Office Action for U.S. Appl. No. 14/470,423 dated Jan. 21, 2016.
U.S. Office Action for U.S. Appl. No. 13/128,821 dated Dec. 14, 2012.
U.S. Office Action for U.S. Appl. No. 13/128,821 dated Apr. 24, 2012.
U.S. Office Action for U.S. Appl. No. 14/316,154 dated Dec. 18, 2014.
U.S. Office Action for U.S. Appl. No. 13/512,936 dated Aug. 14, 2013.
U.S. Office Action for U.S. Appl. No. 13/056,261 dated Jan. 9, 2014.
U.S. Office Action in U.S. Appl. No. 13/056,261 dated Aug. 7, 2013.
U.S. Office Action on U.S. Appl. No. 14/287,917 dated Sep. 26, 2014.
Written Opinion for PCT/EP2010/068658 dated Jun. 1, 2012.
Written Opinion for Singapore Application No. 201103393-3 dated May 2, 2012.
Canadian Office Action for CA 2,732,309 dated Nov. 8, 2016.
U.S. Notice of Allowance on U.S. Appl. No. 14/945,952 dated Dec. 7, 2016.
Non-Final Office Action for U.S. Appl. No. 15/910,278 dated Nov. 26, 2019 (7 pages).
First Office Action for CN 201580019701.2 dated Nov. 15, 2019 (18 pages).
Office Action for CA 3026948 dated Jan. 15, 2020 (4 pages).
Non-Final Office Action on U.S. Appl. No. 15/962,632 dated Mar. 30, 2020 (10 pages).
Non-Final Office Action on U.S. Appl. No. 16/236,716 dated Apr. 29, 2020 (9 pages).
Notice of Allowance on U.S. Appl. No. 15/369766 dated Mar. 5, 2020 (8 pages).
Notice of Allowance on U.S. Appl. No. 15/910278 dated Mar. 9, 2020 (8 pages).

(56) References Cited

OTHER PUBLICATIONS

Chinese Office Action on CN 201580019701.2 dated Aug. 17, 2020 (9 pages)
Final Office Action on U.S. Appl. No. 15/962,632 dated Oct. 6, 2020 (13 pages).
International Preliminary Report on Patentability on PCT/IB2019/051635 dated Sep. 17, 2020 (7 pages).
International Preliminary Report on Patentability on PCT/IB2019/053275 dated Nov. 5, 2020 (8 pages).

\* cited by examiner

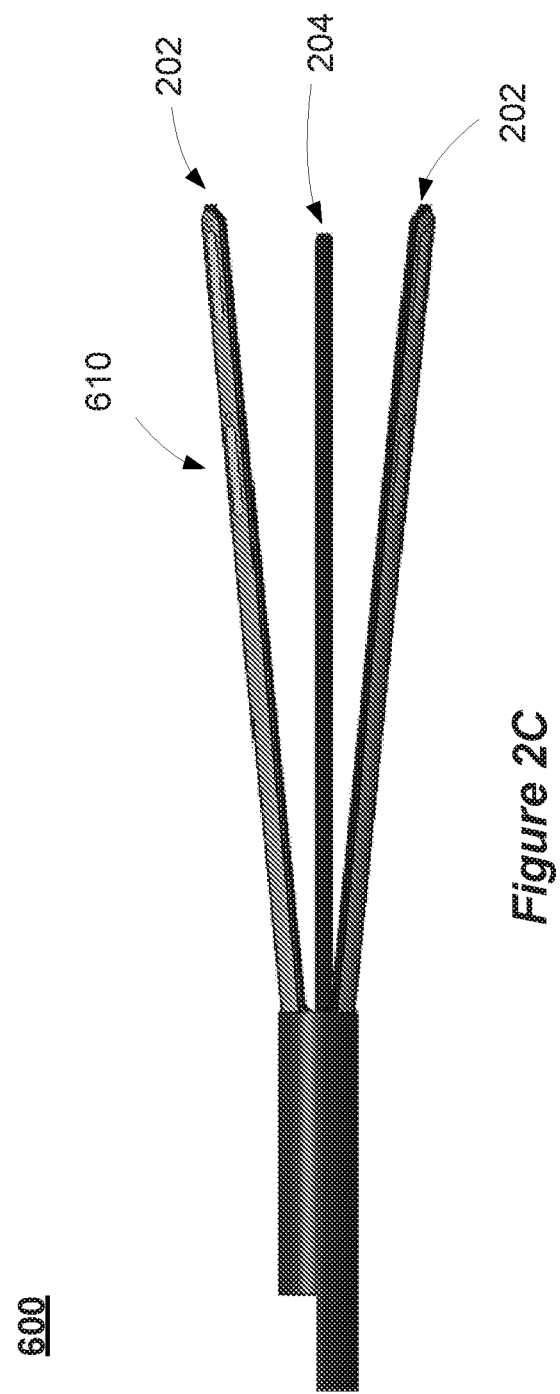

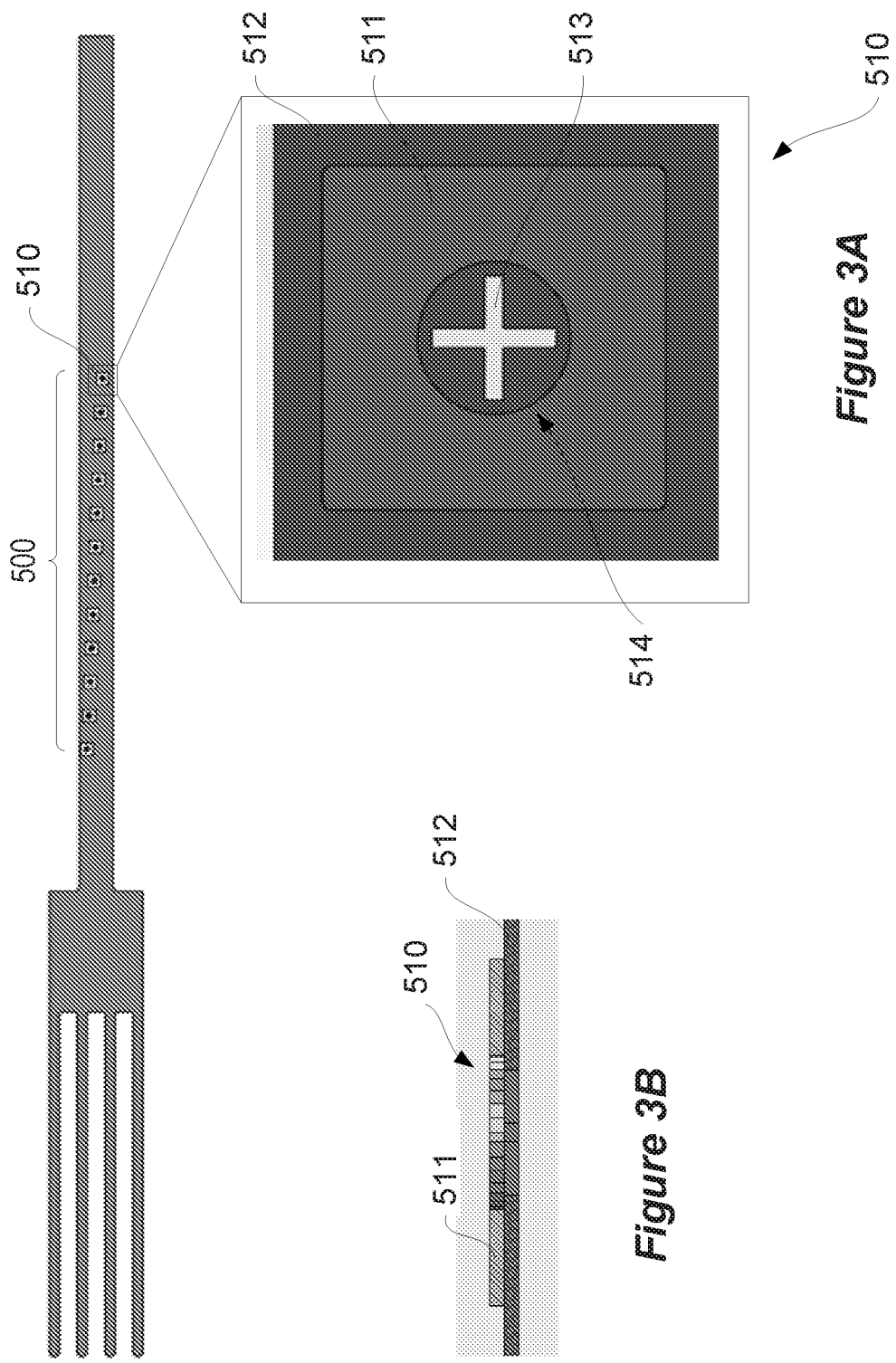

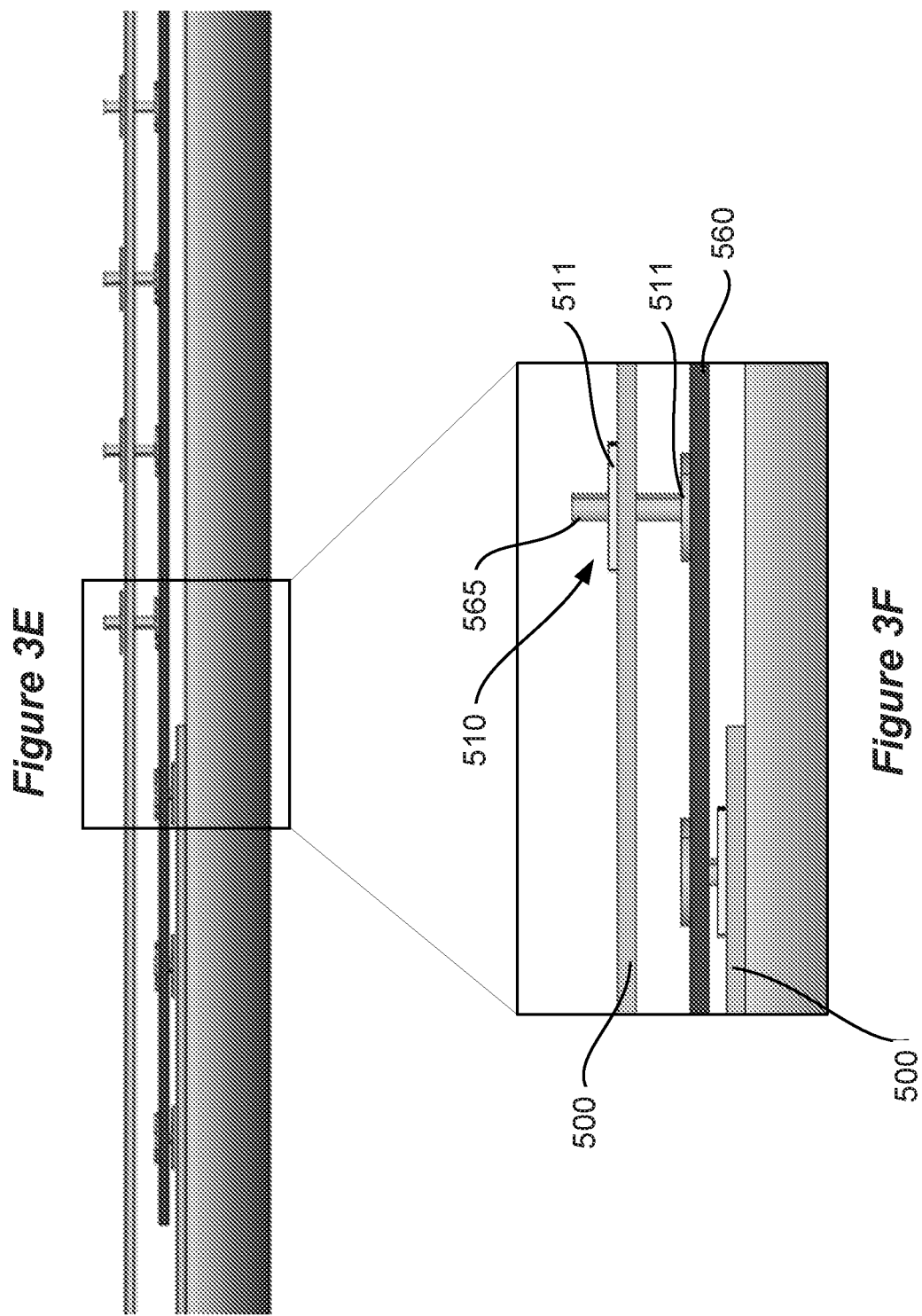

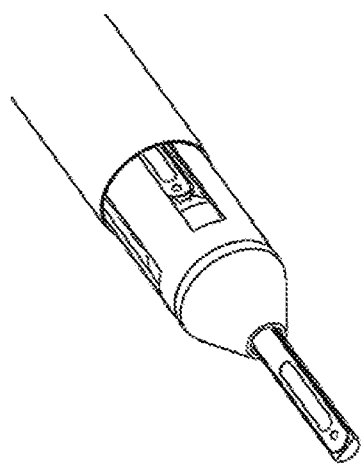
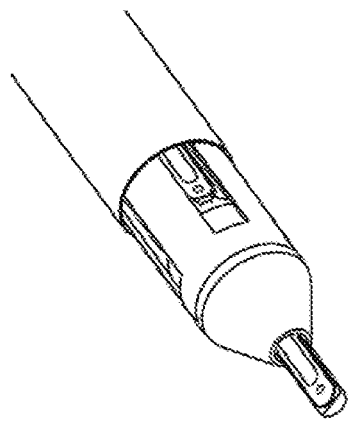
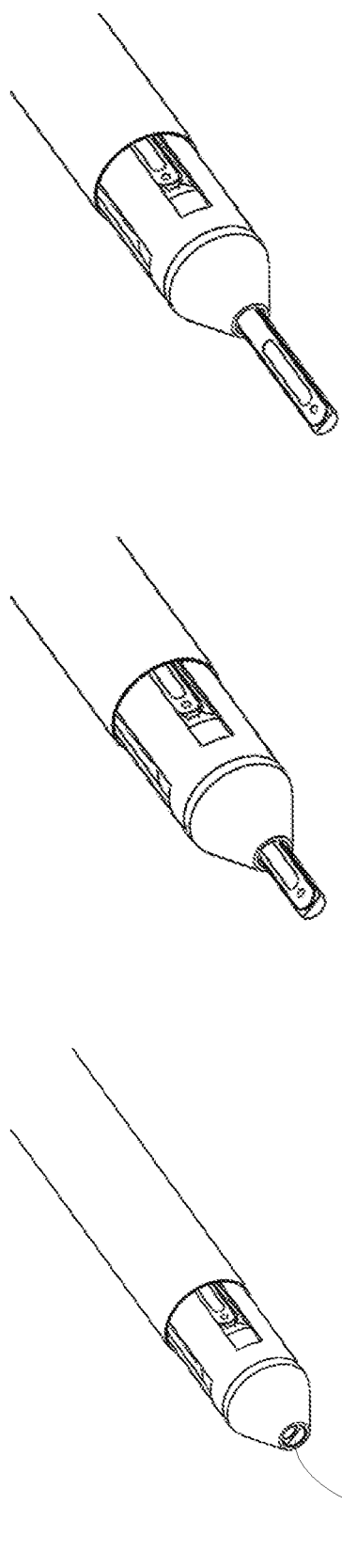
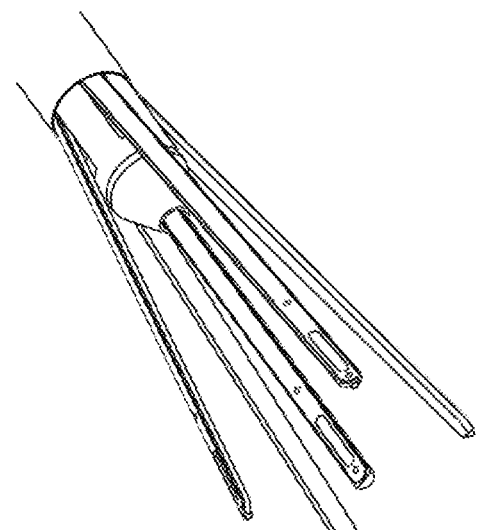
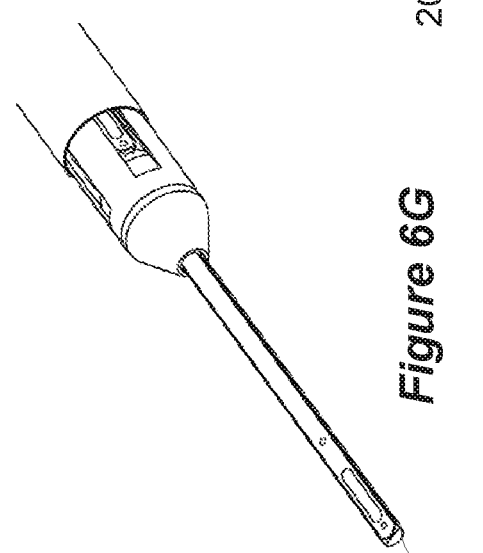
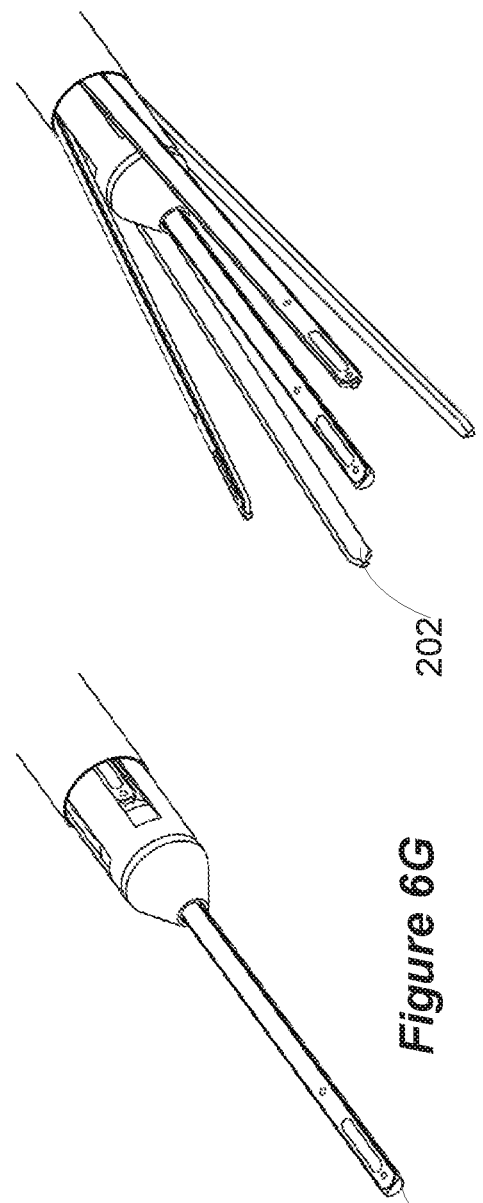

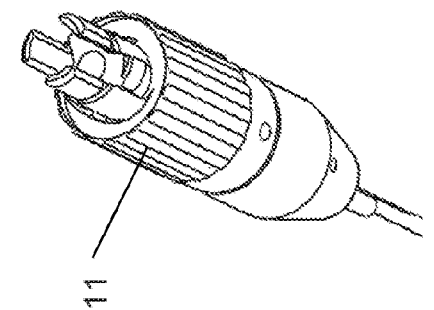
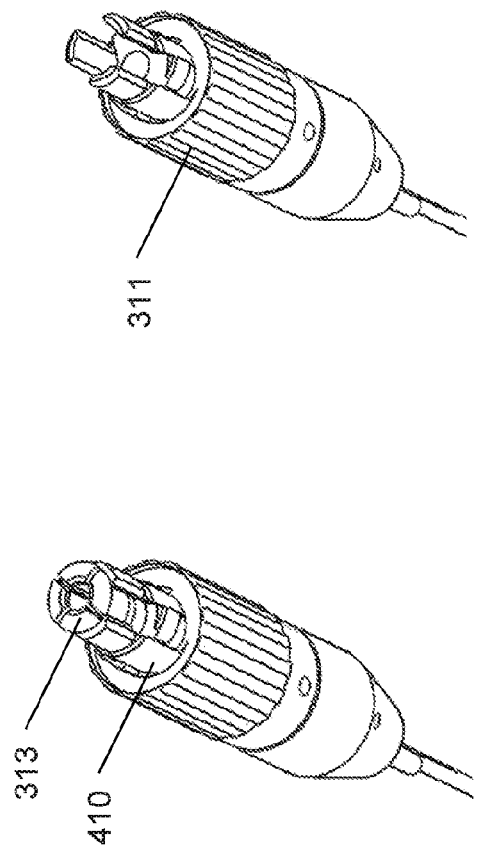
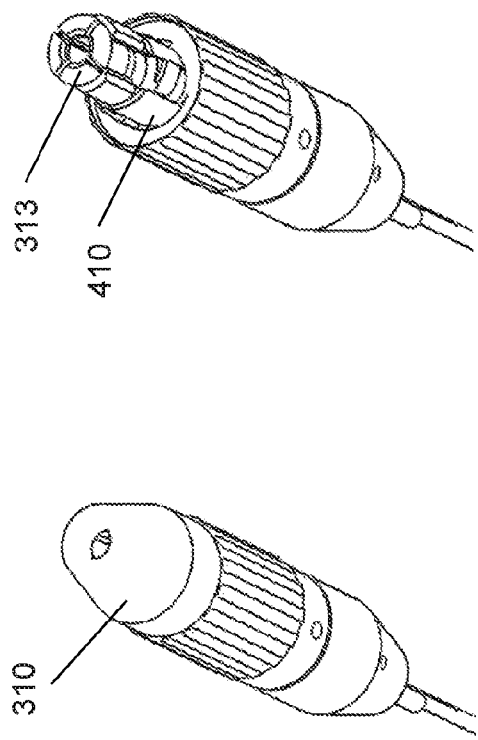
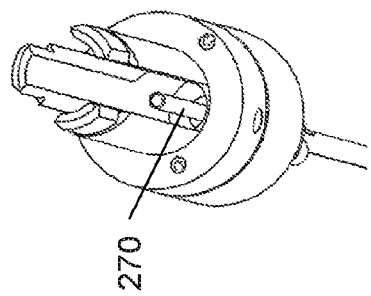
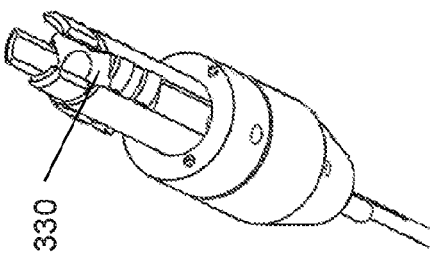

DEVICE FOR INTERACTING WITH NEUROLOGICAL TISSUE AND METHODS OF MAKING AND USING THE SAME

RELATED APPLICATIONS

The present application is a national stage application, filed under 35 U.S.C. § 371, of PCT Application No. PCT/IB2015/053610, filed May 15, 2015, entitled "DEVICE FOR INTERACTING WITH NEUROLOGICAL TISSUE AND METHODS OF MAKING AND USING THE SAME," which claims priority to U.S. Application No. 61/994,359, filed May 16, 2014, all of which are hereby incorporated by reference in their entireties.

BACKGROUND

Medical devices can interact with tissue of a subject to diagnose or treat the subject. For example, the subject can have neurological pathologies, which need to be diagnosed and treated.

SUMMARY

Neural recording and neurostimulation devices can be used in the cochlea, the retina, the peripheral nervous system, the spine, the brain, and other parts of the body. Generally, neural recording can be performed in deep brain structures by surgically inserting conductive electrodes and amplifying neurological signals using external electronic equipment. Neurostimulation can be performed by surgically implanting conductive electrodes in the target, and using an implantable pulse generator to apply electrical signals to the conductive electrodes.

The conductive electrodes can be inserted into the deep brain structures through stereotaxy or endoscopy procedures. During these procedures a lead cannula can be implanted near the target tissue. The conductive electrodes can be fed through the cannula to the target tissue.

Described herein are microelectrode devices to provide highly localized neural recording or neural stimulation to a neurological target. The device includes a plurality of electrodes disposed along the shafts of deployable flexible pins. The deployable flexible pins are enclosed within an elongated probe shaft, and can be expanded from their enclosure. Additionally, a specifically manufactured protective housing can be coupled to at least a portion of the elongated probe shaft. During deployment of the flexible pins, the protective housing of the microelectrode device reduces friction between the flexible pins and the probe shaft and thus reduces the risk of delamination to the flexible pins during deployment.

According to one aspect of the disclosure, an implantable microelectrode device includes an elongated shaft having an outer wall and a distal end. The elongated shaft defines an internal lumen therethough and the outer wall defines a plurality of windows therein. An end cap is coupled with the distal end of the elongated shaft. The end cap has a frustum end projecting into the internal lumen of the elongated shaft. The device also includes a protective tube coupled with the outer surface of the elongated shaft. A portion of the protective tube covers a portion of each of the plurality of windows. The device also includes a probe assembly. The probe assembly includes a plurality of flexible pins. Each of the plurality of flexible pins can be deployed through a different one of the plurality of windows. Each of the plurality of flexible pins exit the elongated shaft at an angle defined by the frustum end of the end cap and a distal end of the protective tube.

In some implementations, the protective tube is configured to substantially reduce a friction induced on the plurality of flexible pins during deployment through the plurality of windows. Compared to a device without the protective tube, the protective tube may reduce the friction induced on the plurality of flexible pins during deployment by between about 50% and about 20%. The protective tube can include a polymeric material. In some implementations, the protective tube and the plurality of flexible pins include a same substrate material. The plurality of flexible pins can be configured to slide along the frustum end of the end cap projecting into the internal lumen and the protective tube. The coefficient of friction between the protective tube and the plurality of flexible pins may be between about 0.5 and about 0.01 or between about 0.2 and about 0.01.

In some implementations, the microelectrode device can also include a microelectromechanical system (MEMS) component that can include a first plurality of MEMS legs. Each of the first plurality of MEMS legs can be aligned and coupled with an outer face of one of the plurality of flexible pins. The device can also include a second plurality of MEMS legs that can be coupled to the first plurality of MEMS legs by a foldable strip. Each of the second plurality of MEMS legs can be aligned and coupled with an inner face of one of the plurality of flexible pins. The MEMS leas can include at least one electrode.

In some implementations, at least one electrode is disposed on each of the plurality of flexible pins. The probe assembly can further include a central pin that is deployed through a central channel of the end cap. The frustum end of the end cap can define the minimum exit angle of the flexible pins from the elongated shaft. The protective tube can define the maximum exit angle of the flexible pins from the elongated shaft. In some implementations, the device includes at least four windows.

The device can include a translation system. The translation system can include a translation ring and a translator rod. The translation system can be configured to convert a rotational movement of the translation ring into an axial movement of the translator rod. The translator rod is coupled to the probe assembly. In some implementations, the translation system includes a second translation ring that is configured to convert a rotational movement into an axial movement to deploy the central pin.

According to another aspect of the disclosure, a method for obtaining neurological activity data includes implanting a microelectrode device within a vicinity of a neurological target. The device includes an elongated shaft having an outer wall and a distal end. The elongated shaft defines an internal lumen and the outer wall defines a plurality of windows. The device also includes an end cap coupled with the distal end of the elongated shaft. The end cap has a frustum end projecting into the internal lumen of the elongated shaft. The device also includes a protective tube coupled with the outer surface of the elongated shaft. Portions of the protective tube cover a portion of each of the plurality of windows. The device further includes a probe assembly that includes a plurality of flexible pins. Each of the plurality of flexible pins includes a plurality of electrode sites. The method also includes deploying at least one of the plurality of flexible pins through a different one of the plurality of windows. The plurality of flexible pins can deploy at an exit angle defined by the frustum end of the end cap and a distal end of the protective tube. The method further includes recording the neurological activity using the plurality of electrode sites.

In some implementations, the method can include coupling the microelectrode device with a stereotactic apparatus. The plurality of flexible pins may be deployed by rotating a translator ring of the microelectrode device. In some implementations, the microelectrode device can include multiple translator rings to enable independent deployment of the flexible pins. The plurality of flexible pins can be retracted and the neurological probe can be removed from the neurological target. The position of the neurological probe within the brain of a subject can be determined responsive to the recorded neurological activity. The method can include coupling the neurological probe with a neural recording and neurostimulation device.

In some implementations, the protective tube is configured to substantially reduce a friction induced on the plurality of flexible pins during deployment through the plurality of windows. The protective tube can include a polymeric material. The protective tube and the plurality of flexible pins can include a same substrate material. A minimum of the exit angle can be defined by the frustum of the end cap, and a maximum of the exit angle can be defined by the distal end of the protective tube. In some implementations, the at least four windows are defined in the outer wall of the elongated shaft. In some implementations, the method includes sliding the plurality of flexible pins along the frustum end projecting into the internal lumen and the protective tube.

In some implementations, the method includes applying a rotational force to a rotational translation system. The rotational translation system can include a translator rod. The rotational translation system is configured to convert the rotational force applied to the rotational translation system into an axial movement of the translator rod. The translator rod can be coupled to the probe assembly.

BRIEF DESCRIPTION OF THE DRAWINGS

The figures, described herein, are for illustration purposes. Various aspects of the described implementations may be shown exaggerated or enlarged to facilitate an understanding of the described implementations. In the drawings, like reference characters generally refer to like features, functionally similar or structurally similar elements throughout the various drawings. The drawings are not necessarily to scale. The drawings are not intended to limit the scope of the present teachings in any way. The systems and methods may be understood from the following illustrative description with reference to the following drawings in which:

FIGS. 2B and 2C are views of an exemplary microelectrode probe assembly, suitable for use in the microelectrode device of FIG. 1.

FIGS. 3A-3H illustrate various views of an example connection pad, suitable for use in the microelectrode device of FIG. 1.

FIGS. 6C-6H illustrate the tip of the microelectrode drive with an independently controllable central pin.

FIGS. 9A-9E illustrate the systematic disassembling of the translation system.

DETAILED DESCRIPTION

Figure 1:
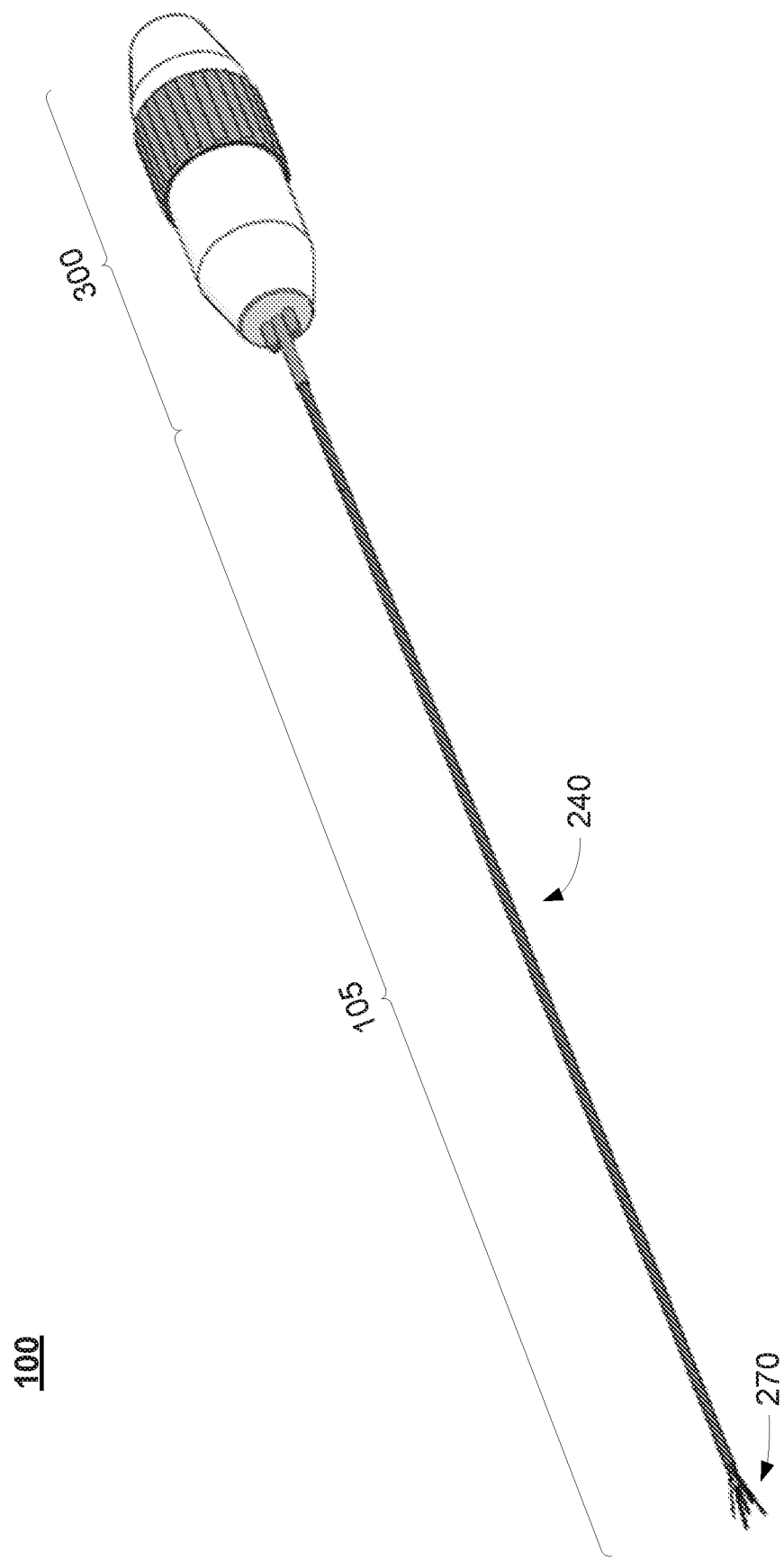
FIG. 1 is a perspective view of one implementation of a microelectrode device.

The various concepts introduced above and discussed in greater detail below may be implemented in any of numerous ways, as the described concepts are not limited to any particular manner of implementation. Examples of specific implementations and applications are provided primarily for illustrative purposes. Medical devices discussed herein can perform neural recording and neurostimulation operations to interact electrically with tissue. In the case of neural recording, physiological measurements can be performed on neurological tissue to diagnose or treat a patient. In the case of neurostimulation, an electric charge can be transferred to the tissue in order to create a therapeutic outcome or to generate a diagnosis.

Described herein are microelectrode array devices, and methods of fabrication and use of the same, to provide localized and efficient electrical stimulation of a neurological target, such as individual neurons, groups of neurons, and neural tissue as may be located in an animal nervous system, such as deep within a human or animal brain. In small, difficult to find brain targets such as the Pedunculopontine Nucleus, or in targets that require localized levels of neural stimulation, such as the Subthalamic Nucleus, many microelectrodes are required in the brain region to find the target using electrophysiological recording. A higher number of microelectrodes can increase the chance of finding the neurons required for therapeutic stimulation. The microelectrode or group of microelectrodes that are closest to the target brain region can be used for chronic, therapeutic stimulation or inhibition.

The stimulation can be highly localized. In some implementations, the stimulation is localized by using small electrodes—for example between about 2 μm and about 2 mm in either of diameter or width. The relative spacing between such microelectrode elements can be between about 2 μm and about 2 mm. In some examples, microelectrodes of about 150 μm in diameter, with about a 1000 μm spacing are used to stimulate neural tissue. An array of such microelectrode elements may include one or more such elements (e.g., sixteen elements), each disposed at a respective position or site.

Smaller microelectrode elements can provide neurological stimulation that is highly localized and efficient because an array of such microelectrodes can identify the stimulation region of interest. For example, one or more microelectrode elements of such an array of microelectrode elements can be used to record neuronal activity in the vicinity of the detecting or recording microelectrode elements. Such refinement offered by the relatively small size or spacing of the microelectrode elements can be used to obtain a highly localized map of neuronal activity in the region surrounding the implant. A suitably dimensioned microelectrode array having multiple microelectrode elements positioned in a general vicinity of a neurological target, can be used to locate a precise neurological target without further repositioning, by identifying those one or more microelectrode elements located in a very specific region of the neurological target. The microelectrode array can be programmed to stimulate in a very specific region, for example, using a certain number of the microelectrode elements to actively stimulate the surrounding neurons or neuronal tissue, while other electrode elements of the array remain inactive.

In some embodiments, the microelectrode arrays are positioned in three-dimensional spaces, rather than implanted as linear arrays or two-dimensional arrays on films. The microelectrode arrays can be positioned along shafts, which radiate from a central lumen in order to cover the target tissue.

In some embodiments, an elongated device that includes microelectrode arrays having elements with relatively small size or spacing can be used to obtain a highly localized map of neuronal activity in the region surrounding the implant. For example, such a device configured with a linear array of microelectrodes positioned along a length of a distal end of the device can be placed into a patient's brain. The elements of the microelectrode array can envelop a region including the neurological target. Neurological activity can be independently detected by one or more of the microelectrode elements. The detected activity may be captured in a recorder or display device, allowing a clinician to identify which one or more of the microelectrode elements is positioned closest to the intended target. Knowing a respective location of each of the microelectrode elements along the device, and determining the distance to a reference, such as the patient's skull, a precise location of the target can be determined as the distance along a trajectory of the device. The distance is measured from the reference to the particular microelectrode element. The location of the target can be determined without any repositioning of the elongated device, thereby simplifying the medical procedure.

In some embodiments, the device is for acute intra-surgical use; being removed after the target has been located. The device can be replaced with a chronic probe or positioned at the determined target location. The device can be left in place as a chronic device, with the same microelectrodes or different ones used to record or stimulate the neurological target over an extended period of time.

In some implementations, the microelectrode device described herein includes inner and outer stent subassemblies. The outer stent subassembly can include an elongated shaft that defines an internal lumen. Multiple windows are defined in the wall of the elongated shaft towards elongated shaft's distal end. The microelectrode device also includes an end cap coupled with the distal end of the elongated shaft. A portion of the end cap includes a frustum end. The frustum end of the end cap projects into the internal lumen of the elongated shaft. A protective tube can be coupled with an outer surface of the elongated shaft. The protective tube can cover a portion of each of the windows. The microelectrode device can also include a probe assembly. The probe assembly is configured to slid through the internal lumen of the elongated shaft. The probe assembly can include flexible pins. Each of the flexible pins are aligned with one of the windows defined in the elongated shaft such that the flexible pins can deploy through the window. The angle at which the flexible pins are deployed through the window is defined, at least in part, by the frustum end of the end cap and a distal end of the protective tube.

FIG. 1 illustrates an exemplary implementation of a microelectrode device 100. The microelectrode device 100 can include at least one elongated microelectrode lead assembly 105. The lead assembly 105 can include at least one outer stent sub-assembly 240 and at least one inner stent sub-assembly 270. As illustrated in FIG. 1, the microelectrode device 100 is in a deployed state. In the deployed state, the distal end of the inner stem sub-assembly 270 can be visible as its microelectrode probe assembly protrudes out of the outer stent sub-assembly 240. At least one translation system 300 (also referred to as a controller 300) can be coupled with the proximal end of the lead assembly 105.

The outer stent sub-assembly 240 can provide a protective housing through which the inner stent sub-assembly 270 slides when driven by the translation system 300. In some implementations, the walls of the outer stent sub-assembly 240 form an elongated shaft that defines an internal lumen. The inner stent sub-assembly 270 can run through the internal lumen of the outer stent sub-assembly 240. The translation system 300 can be controlled by an operator and can enable the operator to select to what length each of the flexible pins of the microelectrode probe assembly is deployed.

Figure 2A:
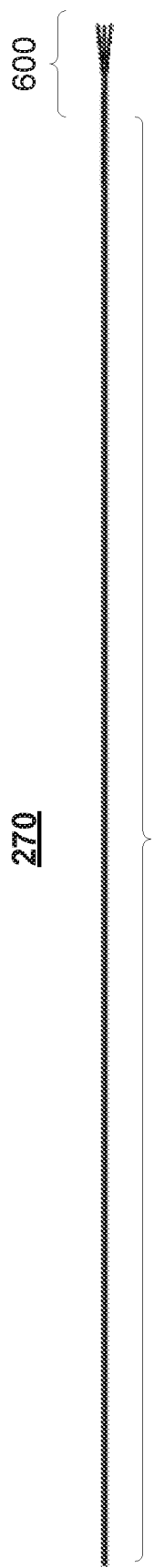
FIG. 2A is a planar view of an exemplary inner stent sub-assembly, suitable for use in the microelectrode device of FIG. 1.
Figure 2B:
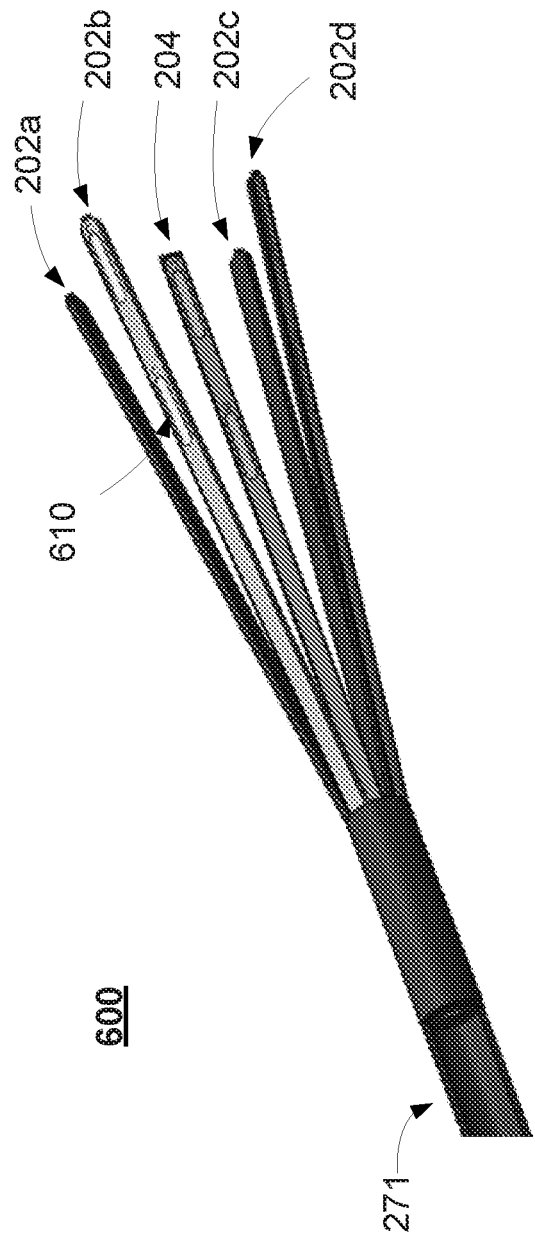

FIG. 2A illustrates an example inner stent sub-assembly 270. The inner stent sub-assembly 270 includes a microelectrode probe assembly 600 coupled to the distal end of a stent tube 271. The microelectrode probe assembly 600 is also illustrated in FIGS. 2B and 2C. In some implementations, the stent tube 271 makes up the majority of the length of the inner stent sub-assembly 270. The inner stent sub-assembly 270 can vary in length and diameter but is generally at least about 28 cm long, (e.g., at least 20 cm long, at least 25 cm long, at least 28 cm long, at least 30 cm long, etc. and around 1.27 mm in diameter (e.g., in the range of 1.0-2.0 mm in diameter).

FIGS. 2B and 2C illustrate views of the exemplary microelectrode probe assembly 600. As described above, the microelectrode probe assembly 600 can be coupled to the distal end of the stent tube 271. As revealed by the cut-a-way view of the stent tube 271, the stent tube 271 can be hollow. The stent tube 271 can also be solid or non-hollow. An electrical connection (such as a conductive wire or flexible PCB cable) can run through the stent tube 271 (e.g., through the hollow space) from the translation system 300 to the electrodes of the microelectrode probe assembly 600. The electrical connections can electrically couple the electrodes to a pulse generator or controller. For example, a stimulation signal can be delivered to the electrodes for delivery to the tissue surrounding the implanted electrodes. Additionally, recorded signals can be passed from the electrodes to a feedback system of the pulse generator or external data recorder.

With reference to FIGS. 2B and 2C, among others, the microelectrode probe assembly 600 can include four flexible pins 202a, 202b, 202c and 202d (collectively referred to as flexible pins 202). The flexible pins 202 can include a plurality of electrodes 610 disposed along their shafts. The four (or other number) of flexible pins 202 can project in an anterior, posterior, lateral, or medial direction. The flexible pins 202 can be manufactured by laser cutting the distal portion of the stent tube 271. The flexible pins 202 can also be manufactured separately from the stent tube 271 and then coupled, by gluing or laser welding, to the stent tube 271. The separate manufacture of the flexible pins 202 is discussed farther in relation to FIGS. 2D-2E, among others.

The microelectrode probe assembly 600 also includes a central pin 204 along the same longitudinal axis as the inner stent sub-assembly 270. The central pin 204 can be a flattened wire, and in some implementations, can be separate from the flexible pins 202. The central pin 204 can be coupled to the microelectrode probe assembly 600, by gluing or laser welding. The central pin 204 can include a plurality of electrodes 610 disposed along its shaft.

The components of the inner stent sub-assembly 270 can be manufactured from biocompatible materials. In some implementations, the materials are selected to withstand implantation for 24 hours. The material can also be selected such that they remain biocompatible for durations greater than 24 hours. The non-conducting components of the microelectrode probe assembly 600 can be manufactured from polyimide. The conducting components of the microelectrode probe assembly 600 (e.g., the electrodes 610) can be manufactured from platinum, platinum-iridium, and gold, for example.

The microelectrode probe assembly 600, the flexible pins 202, and the electrodes 610 can be sized and shaped for a specified neurological application. For example, the microelectrode probe assembly 600 may be at least partially placed within the central nervous system of a patient or other subject. The microelectrode probe assembly 600 may be placed within other parts or organs of the body, such as the epidural space of the spine, or other locations within the peripheral nervous system, or within an organ such as the liver or heart. The diameter and length of the microelectrode probe assembly 600 and flexible pins 202 may vary depending on the particular anatomical target. In some implementations, there are 2-4, 4-8, 8-12, and 12-16 flexible pins 202. In some implementations, each flexible pins 202 includes 2-4, 4-8, 8-12, 12-16, and 16-32 electrodes 610 per flexible pin 202.

The electrodes 610 can be sized or spaced to record from or stimulate neurons. The microelectrode probe assembly 600 can be used to detect or record neuronal activity at the neurological target. Neuronal activity naturally occurring within the neurological target gives rise to local electromagnetic fields that can be detected by one or more of the microelectrode elements of the microelectrode array. For example, electric fields produced by neurons can polarize one or more of the microelectrode elements. Such polarization gives rise to an electrical potential with respect to a reference, such as electrical ground, or another one of the electrodes 610. The detected electromagnetic fields are conducted from one or more of the electrodes 610 to a device external to the microelectrode device 100. The signals are conducted from the electrode 610 through the internal electrical conductors within the hollow stent tube 271. The external device that is connected to the microelectrode device 100 can be to one or more additional medical devices, which can further processing of the detected electrical activity. For example, the electrodes 610 can be coupled to a display device or recording device for displaying or recording electrical activity from the neurological target.

In some implementations, one or more of the electrodes 610 are used to electrically stimulate a neurological target. For example, one or more externally generated electrical signals can be applied to one or more of electrode 610. These electrical signals can be conducted through the internal electrical conductors to one or more of the electrodes 610. Depending on the amplitude and polarity of the electrical signals, an electrical field can be induced by the polarized electrodes 610. Electrical fields induced by such polarization can interact with one or more neurons at a target site.

Figure 2D:
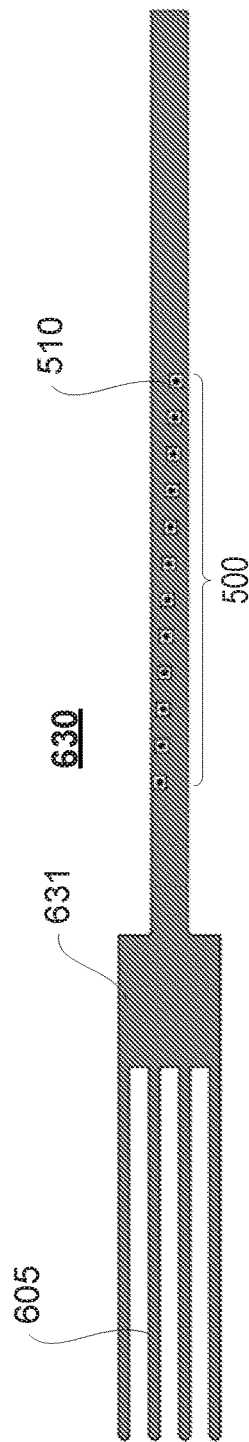
FIGS. 2D-2F illustrate the subcomponents of the microelectrode probe assembly, suitable for use in the microelectrode device of FIG. 1.
Figure 2E:
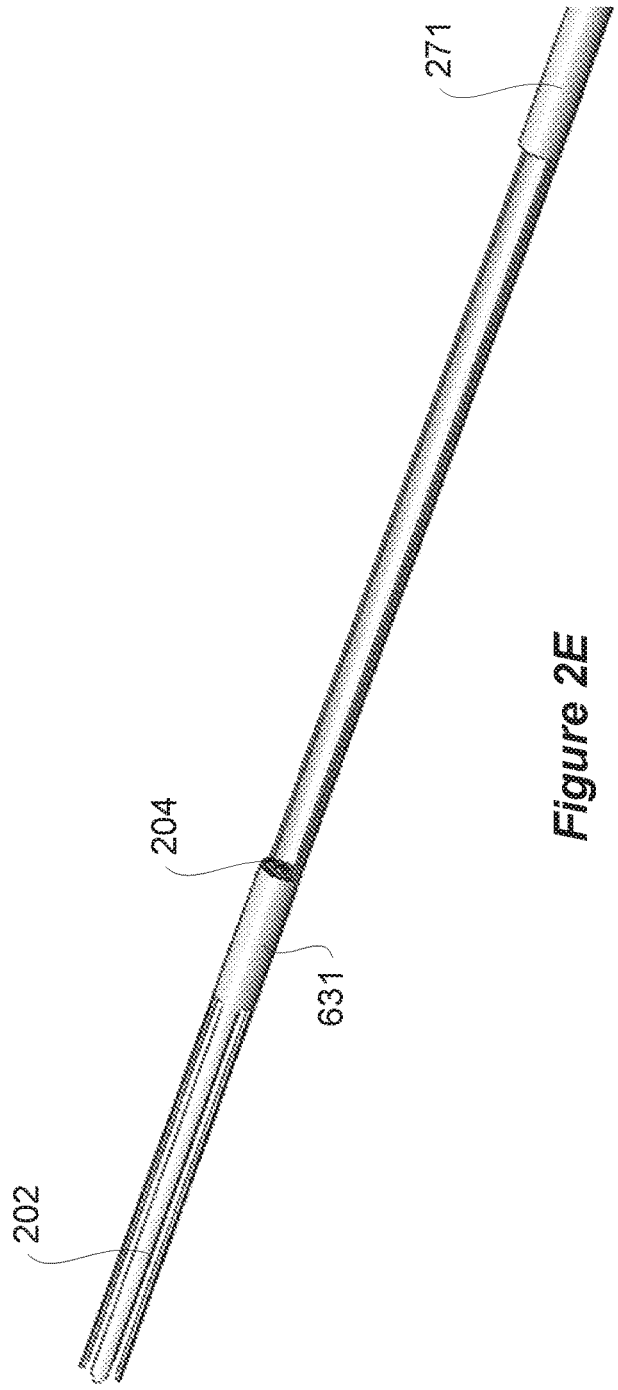

FIGS. 2D and 2E illustrate the subcomponents of the microelectrode probe assembly 600. In general the microelectrode probe assembly 600 includes the microelectromechanical systems (MEMS) components and the stent tube 271. FIG. 2D illustrates the MEMS components 620 and 630, and FIG. 2E illustrates the stent tube 271. The MEMS component 630 includes the electrodes for the flexible pins 202. The MEMS component 630 is divided into three regions: the connection array 500, the shoulder 631, and the MEMS legs 605. The MEMS component 620 includes a connection array 500 and a single MEMS leg 605, and is used to create the central pin 204. FIG. 2E illustrates the stent tube 271 before the MEMS components 630 and 620 are added. The connection array 500 includes a plurality of connection pads 510. The connection array 500 can provide a point of connection to each of the electrodes 610 in the microelectrode probe assembly 600.

Figure 2F:
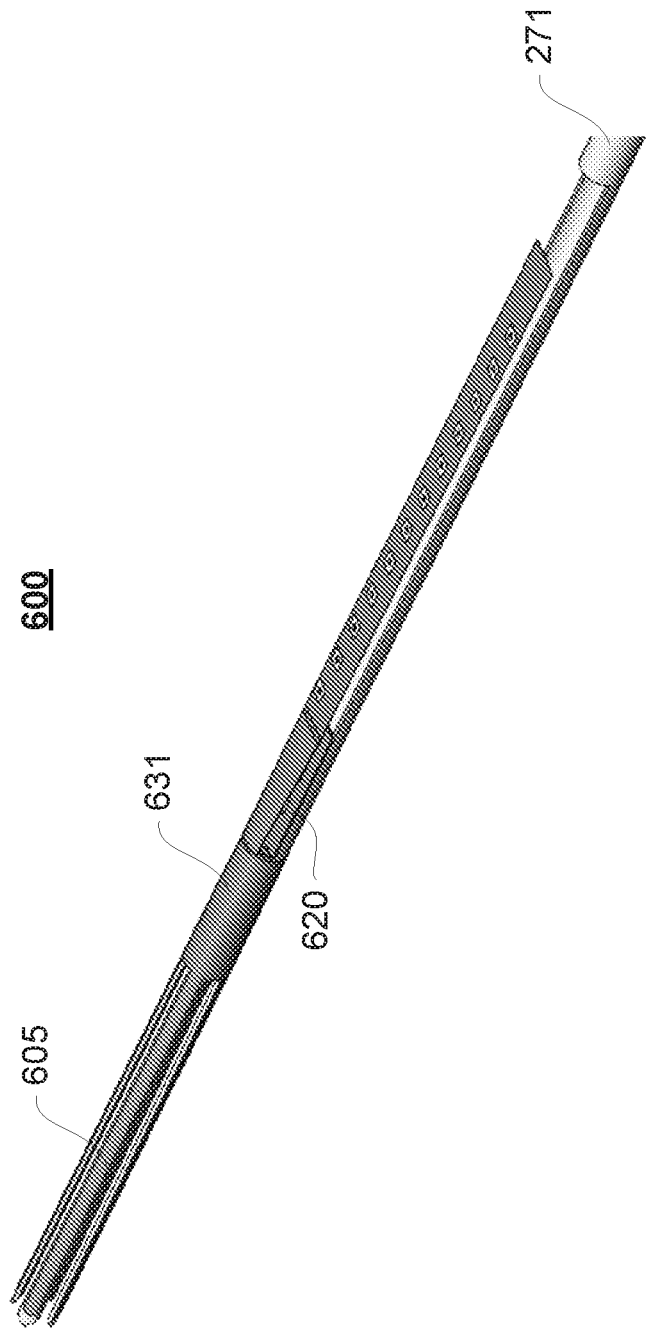

FIG. 2F illustrates a profile view of an assembled microelectrode probe assembly 600. As illustrated in FIG. 2F, each of the MEMS legs 605 are coupled to, and aligned with, a flexible pin 202. The central MEMS component 620 can be coupled with the central pin 204 and the MEMS main component 630 is wrapped around the distal end of the stent tube 271, such that each MEMS leg 605 aligns with a flexible pins 202 of the stent tube 271. In some implementations, the MEMS components are coupled with the stent tube 271 with a biocompatible adhesive.

Figure 2G:
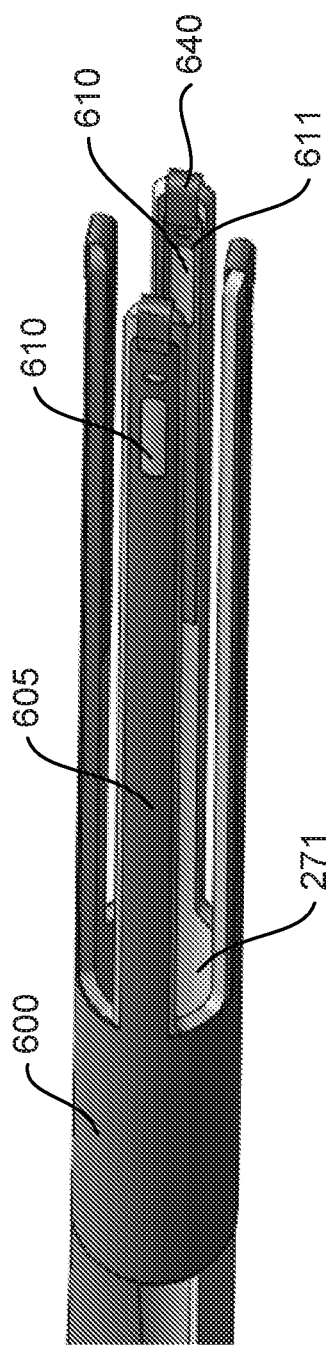
FIGS. 2G-2J illustrate various views of foldable extension legs, suitable for use in the microelectrode device of FIG. 1.
Figure 2I:
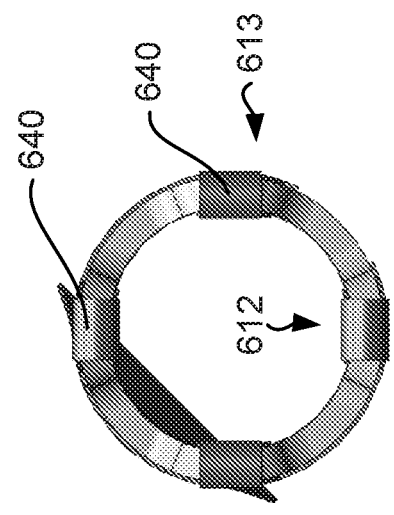
Figure 2H:
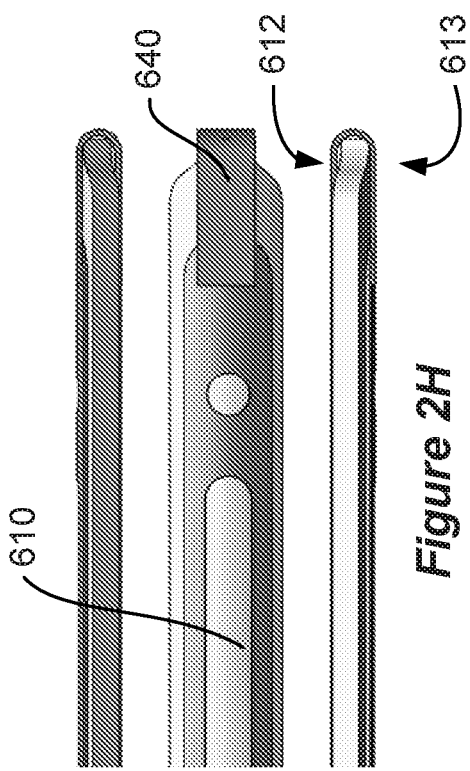

FIGS. 2G, 2H, and 2I illustrate a profile, side, and end views, respectively, of a microelectrode probe assembly 600 with foldable extension legs 611. The foldable extension legs 611 (also referred to as MEMS legs 611) extend past the MEMS legs 605 and are then folded along the inner face of each of the flexible pins 202. The each of the foldable extension legs 611 are aligned and coupled with an inner face 612 of one of the flexible pins 202. In this configuration, the microelectrode probe assembly 600 includes electrodes 610 on bath the inner face 612 and outer face 613 of the flexible pins 202. The foldable extension legs 611 are coupled with the MEMS legs 605 by a foldable strip 640 that folds over the distal tip of each of the flexible pins 202.

Figure 2J:
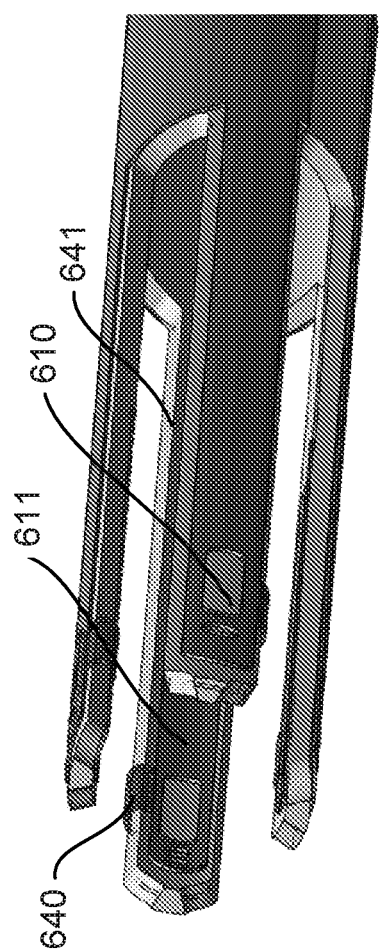

FIG. 2J illustrate a profile and end view, respectively, of a microelectrode probe assembly 600 with foldable extension legs 611. In the example microelectrode probe assembly 600 of FIGS. 2J and 2H, the foldable strips 640 fold over a side face 641 of each of the flexible pins 202.

Referring to FIG. 2F, among others, each of the MEMS components 620 and 630 include a connection array 500. The connection array 500 can include a plurality of connection pads for establishing an electrical connection with the electrodes disposed on the MEMS components 620 and 630.

FIG. 3A illustrates an enlarged, top-view of an example connection pad 510. FIG. 3B illustrates a side-view of the connection pad 510. Each of the connection pads 510 are electrically coupled with an electrode 610 through an electrical conductor embedded within the polymeric insulation layer 512 MEMS component. A conductive pad 511 is positioned on top of the polymeric insulation layer 512 and over the conductive electrical line embedded within the polymeric insulation layer 512. A through hole 514 is made in the conductive pad 511. Within the through hole 514, a cross-shaped cut 513 is etched through polymeric insulation layer 512. In one embodiment conductive pad 511 is includes gold. The conductive pad 511 can be deposited on the polymeric insulation layer 512 by galvanic deposition onto a platinum layer.

Figure 3C:
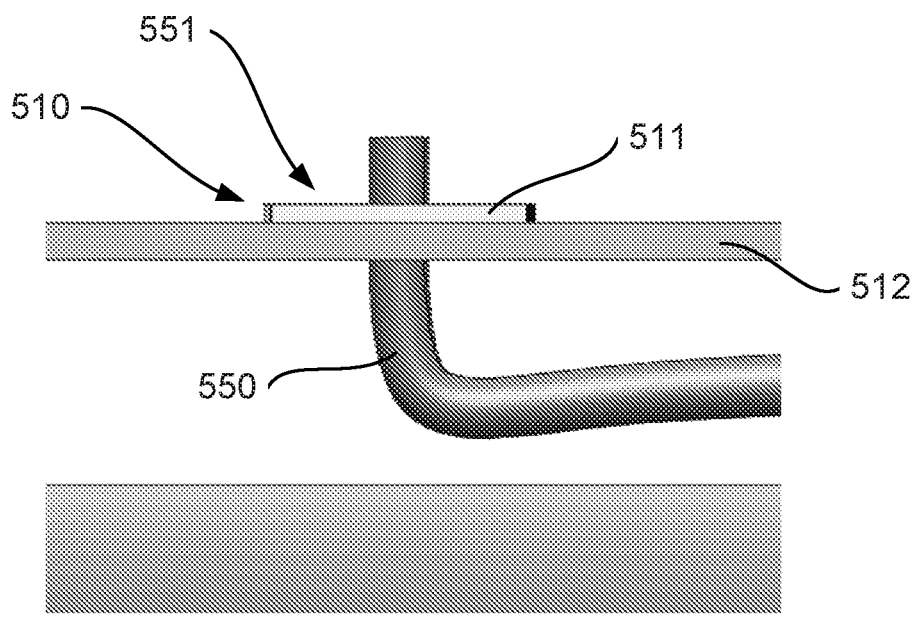
Figure 3D:
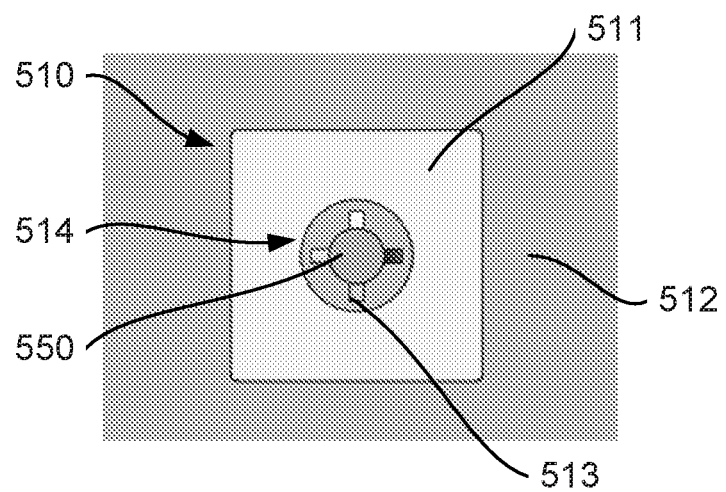
Figure 3H:
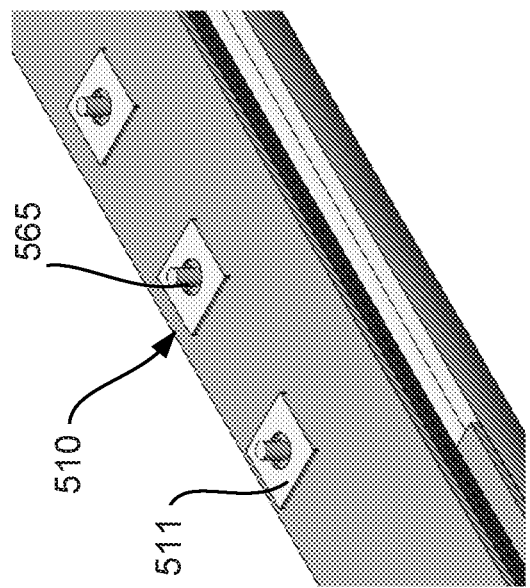
Figure 3G:
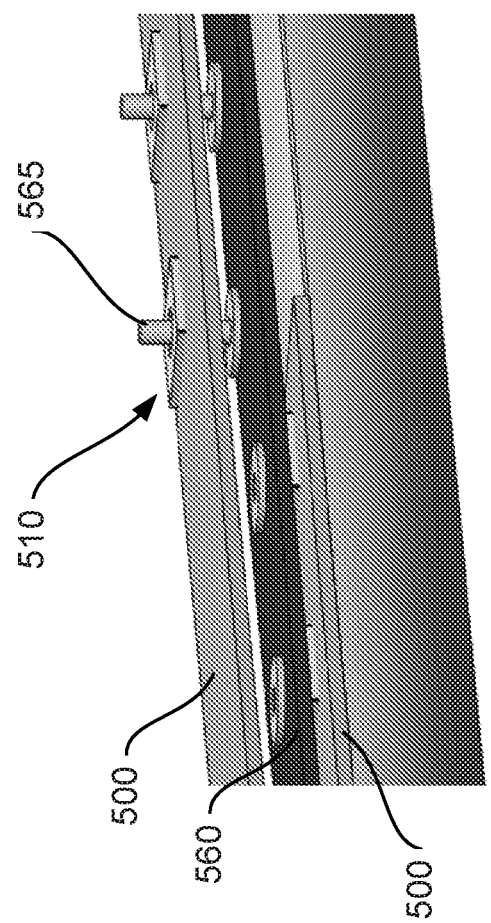

FIGS. 3C and 3D illustrate a side view and top view, respectively, of connection pad 510 with a conductive wire 550 passing through the hole 514 in conductive pad 511. The other end of this electrical conductive wire 550 is connected to an external electronic device or controller. The cross-shaped cut 513 enables that region of polymeric layer 512 to be flexible and temporarily hold the electrical conductive wire 550 in place once it is inserted. In one embodiment the wire can be secured underneath with a non-conductive adhesive. On the surface 551 of the conductive pad 511 a conductive adhesive is used to secure the wire and establish an electrical contact between the wire 550 and conductive pad 511. In some implementations, a PCB cable with via pins is used rather than (or in addition to inserting) conductive wire 550 through the conductive pad 511.

FIGS. 3E, 3F, 3G, and 3H illustrate various views of an example connection array 500 coupled to a flexible PCB cable 560. The flexible PCB cable 560 can include a plurality of via pins 565, which are aligned with the connection pads 510 in the connection array 500. The flexible PCB cable 560 can provide electrical to a plurality of connection arrays 500. The via pins 565 can be inserted through the cross-shaped cut 513 and the through hole 514 in conductive pad 511—similar to how wire 550 was inserted through the through hole 514. An electrical bond between the conductive pad 511 and via pin 565 can be formed through a conductive adhesive. In some implementations, mechanical strength is provided by encapsulating the above described components within a non-conductive adhesive.

Figure 3I:
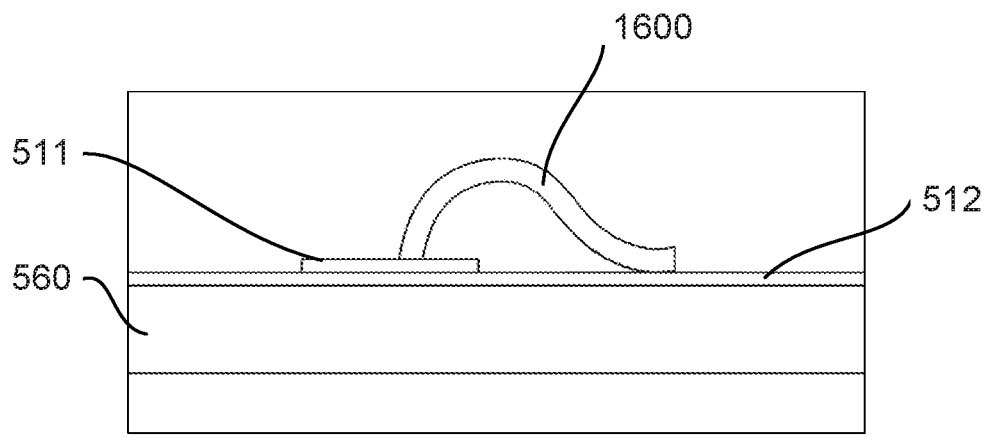
FIGS. 3I, 3J, and 3K illustrate various views of coupling a polymeric insulation layer to a flexible cable, suitable for use in the microelectrode device of FIG. 1.
Figure 3J:
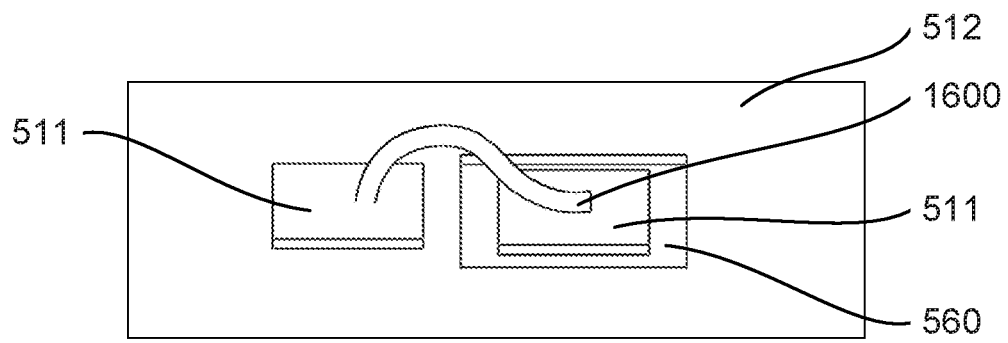
Figure 3K:
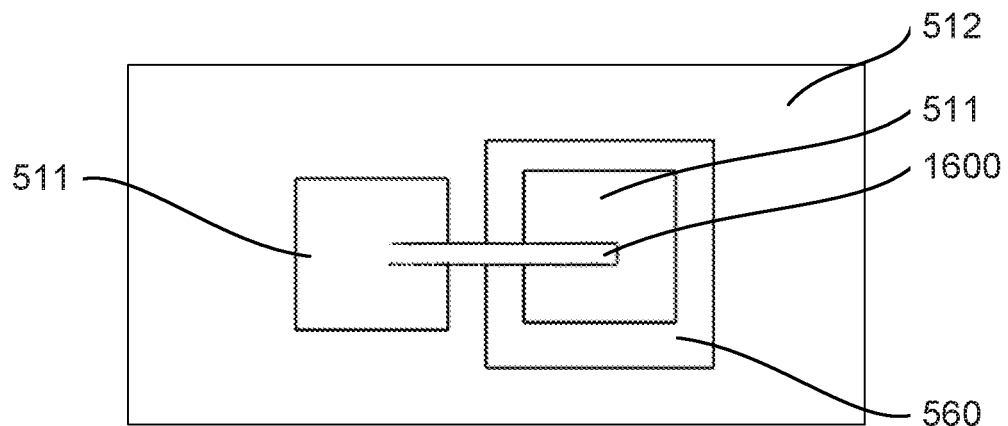

FIGS. 3I, 3J, and 3K illustrate various views of coupling the polymeric insulation layer 512 to a flexible cable 560. In FIGS. 3I, 3J, and 3K, the flexible pcb cable 560 is coupled with the polymeric insulation layer 512 using wire-bonding. An electrical connection can be established between two conductive pads 511 (e.g. gold pads) by using a bond wire 1600 (e.g., gold wire about 25 μm in diameter) that is coupled with each of the conductive pads 511. In some implementations, the bond wire 1600 is coupled with the conductive pads 511 using ultrasound vibrations and vertical pressure. The conductive pad 511 of the flexible pcb cable 560 can be accessed through window 1700, which passes through the layers of the polymeric insulation layer 512. The window can be 300 μm×300 μm. In some implementations, the window 1700 is at least 50% larger than the conductive pad 511.

Figure 4A:
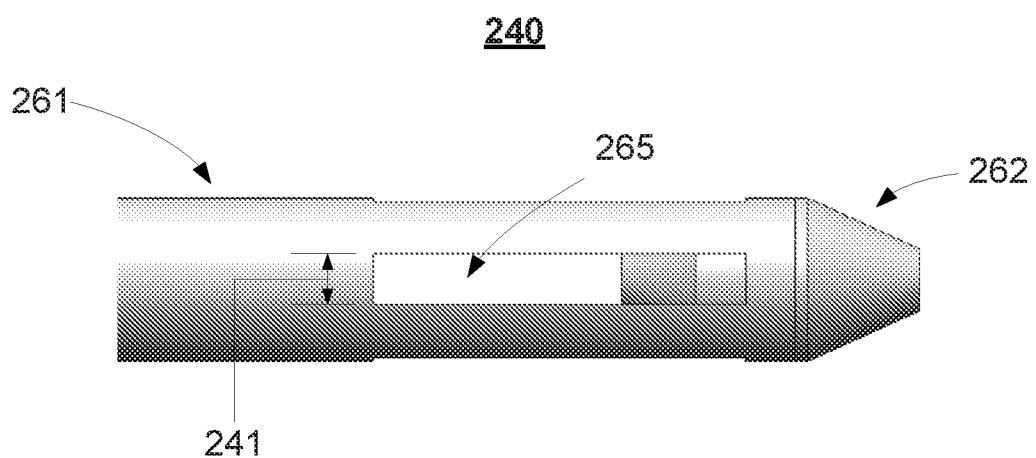
FIG. 4A is a planar view of an exemplary outer stent sub-assembly, suitable for use in the microelectrode device of FIG. 1.
Figure 4B:
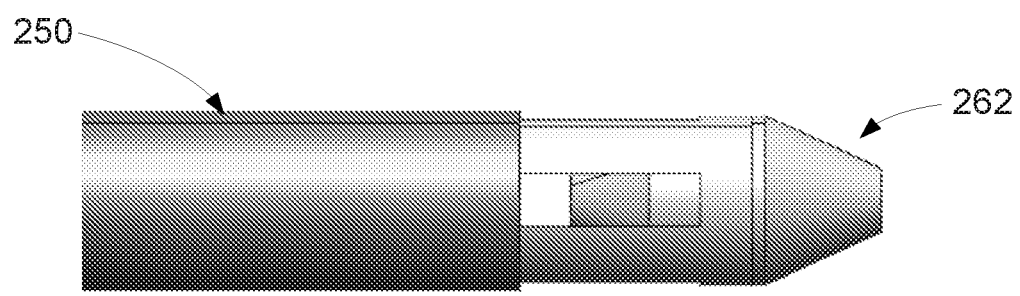
FIG. 4B is a planar view of the outer stent sub-assembly of FIG. 4A with a protective tube.

FIGS. 4A and 4B illustrate example views of the tip of an exemplary outer stent sub-assembly 240. The outer stent tube 261 can run the length of the outer stent sub-assembly 240. The outer stent tube 261 can form an elongated shaft. The walls of the outer stent tube 261, as an elongated shaft, can define an internal lumen through which the inner stent sub-assembly 270 can freely slide. The outer stent tube 261 can vary in length and diameter but, for example, can be at least about 28 cm long, (e.g., at least 20 cm long, at least 25 cm long, at least 28 cm long, at least 30 cm long, etc.) and around 1.27 mm in diameter (e.g., in the range of 1.0-2.0 mm in diameter). The internal diameter of the outer stent tube 261 can be slightly larger than the outer diameter of the inner stent sub-assembly 270, such that the inner stent sub-assembly 270 can freely slide within the outer stent tube 261.

An end cap 262 can be coupled to the distal end of the outer stent tube 261. In some implementations, the end cap 262 is coupled to the outer stent tube 261 by gluing or laser welding. At its distal end, the outer wall of the outer stent tube 261 can define four windows 265. The windows 265 can be defined towards the distal end of the outer stent sub-assembly 240. When assembled, one window 265 can align with each of the flexible pins 202. Embodiments with more or fewer flexible pins 202 also include more or fewer, respectively, windows 265 such that each flexible pins 202 is associated with one window 265. The width 241 of each window 265 can be slightly wider (e.g., within 20%) than the width of the flexible pins 202 associated with the window 265.

FIG. 4B illustrates the tip of the outer stent sub-assembly 240 with a protective tube 250 coupled to the outer surface of the outer stent tube 261. A distal end of the protective tube 250 covers a portion of each window 265 and guides each of the flexible pins 202 out of the window 265. In some implementations, the protective tube 250 runs along a substantial portion of the outer stent tube 261. In some embodiments, the protective tube 250 only covers a portion of the outer stent tube 261 near the windows 265.

Figure 4C:
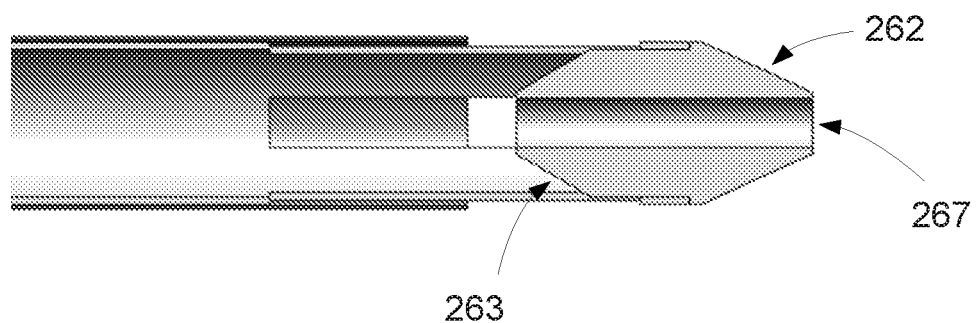
FIG. 4C is a cross-sectional view of the outer stent sub-assembly of FIG. 4B.
Figure 6A:
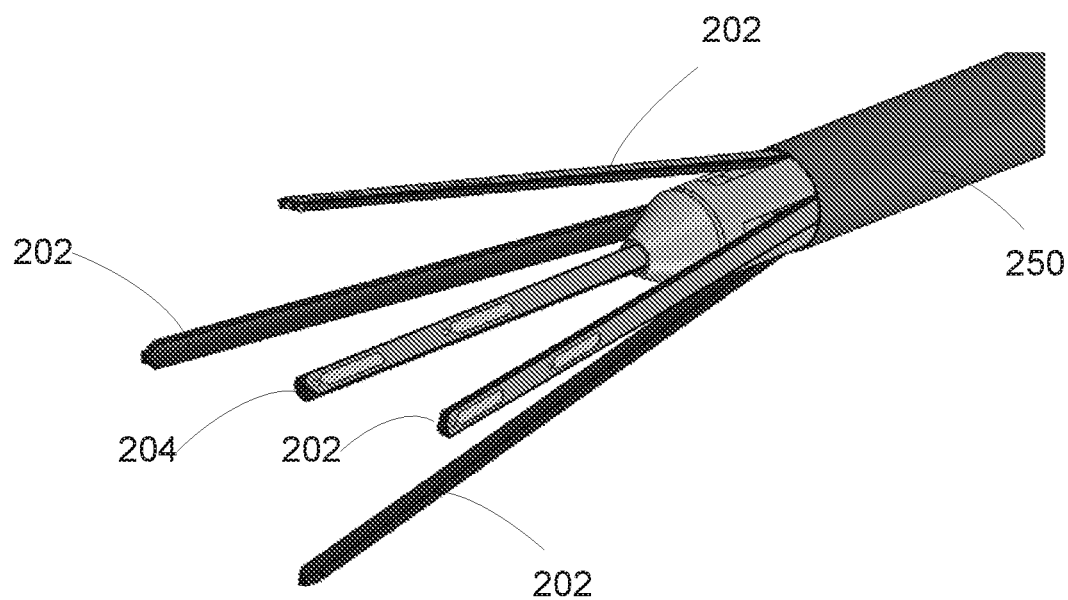
FIG. 6A is a perspective view of the tip of the microelectrode device of FIG. 1 in a deployed state.
Figure 6B:
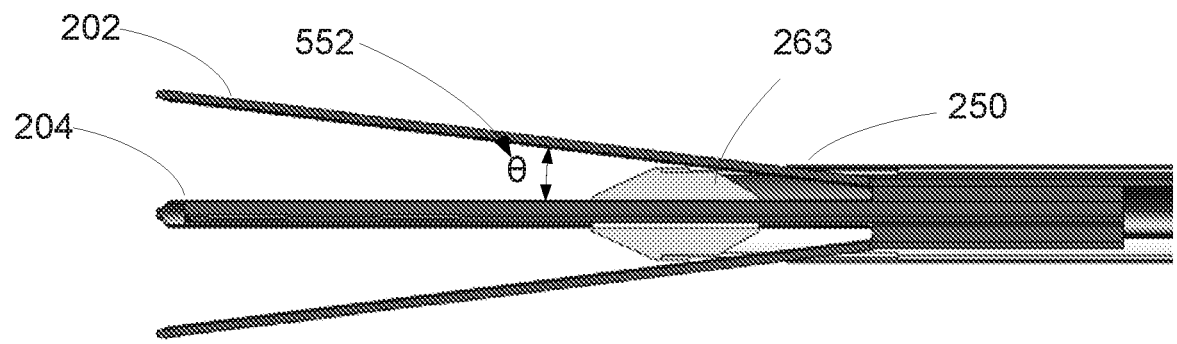
FIG. 6B is a cross-sectional view of the tip of the microelectrode device of FIG. 1 in a deployed state.

FIG. 4C illustrates a cross-sectional view of the tip of the outer stent sub-assembly 240. The end cap 262 includes a proximal frustum (or frustoconical shaped end 263, which is coupled within the outer stent sub-assembly 240. The end cap 262 can couple to the outer stent sub-assembly 240 so that the frustum end 263 projects into the internal lumen defined by the walls of the outer stent tube 261. Referring to FIGS. 6A and 6B, among others, the frustum end 263 of the end cap 262 or the protective tube 250, can enable the flexible pins 202 to exit the outer stent sub-assembly 240 at a predetermined trajectory (or angle). The trajectory of the central pin 204 can be controlled by the central channel 267.

Figure 5A:
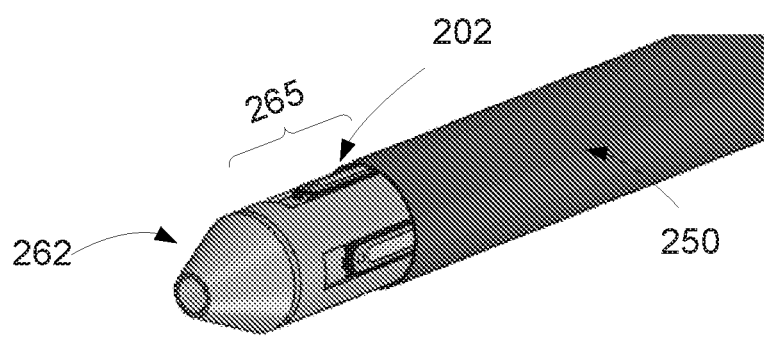
FIG. 5A is a perspective view of the tip of the microelectrode device of FIG. 1 in an undeployed state.
Figure 5B:
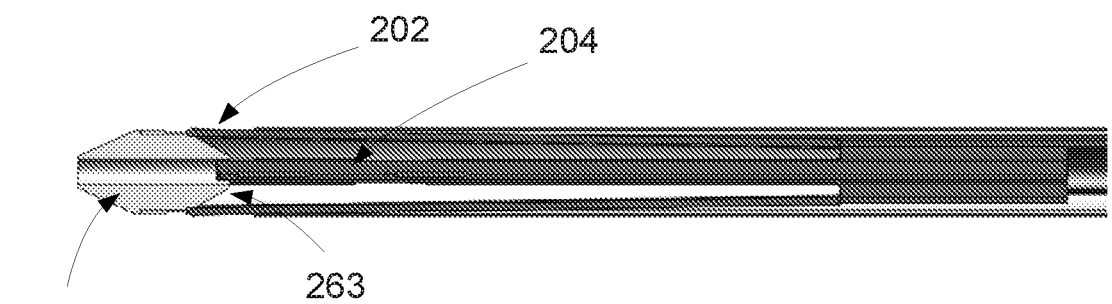
FIG. 5B is a cross-sectional view of the tip of the microelectrode device of FIG. 1 in an undeployed state.

FIG. 5A illustrates a perspective view of the tip of the microelectrode device 100 in its undeployed (or default) state. FIG. 5B illustrates a cross-sectional view of the tip of the microelectrode device 100 in its undeployed state. In the undeployed state, each of the flexible pins 202 can be positioned on the frustum end 263 of the end cap 262 and aligned with one of the windows 265. The central pin 204 is aligned with the central channel 267. In the undeployed state, each of the flexible pins 202 can be contained within the outer stent sub-assembly 240 to enable the device to be implanted. Implanting the microelectrode device 100 in the undeployed state provides a smooth exterior profile that can reduce the trauma caused by the microelectrode device 100 as it passes through surrounding tissue en route to the target tissue.

FIGS. 6A and 6B illustrate the tip of the microelectrode device 100 when the microelectrode probe assembly 600 is in its deployed state. The angle 552 of deployment (or exit angle) is defined in part by at least the outer diameter of the microelectrode device 100, the size and shape frustum feature 263 of the end cap 262, and the placement of the protective tube 250. For example, as the inner stent sub-assembly 270 is driven through the outer stent sub-assembly 240, the inward facing side of the flexible pins 202 comes into contact with the frustum feature 263 of the end cap 262. This drives the flexible pins 202 out of the outer stent sub-assembly 240. On their outward facing edge, the flexible pins 202 are guided by the protective tube 250. In some implementations, the frustum feature 263 determines the exit angle 552 of the flexible pins 202 and the protective tube 250 to ensure that the flexible pins 202 do not over extend past the desired exit angle 552. The protective tube 250 can provide the upper limit to the exit angle the flexible pins 202 as the flexible pins exit the windows 265 and the frustum feature 263 of the end cap 262 can provide the minimum exit angle. For example, if the protective tube 250 extends over a larger portion of the windows 265 toward the most distal end of the end cap 262, the exit angle of the flexible pins 202 would be shallower when compared to implementations where the protective tube 250 extends of a smaller portion of the windows 265.

FIGS. 6C-6H illustrate the tip of the microelectrode drive 100 with an independently controllable central pin 204. FIGS. 6C-6H illustrate the deployment of the central pin 204 through the central channel 267 prior to the deployment of the flexible pins 202. In some implementations, the central pin 204 is deployed after the flexible pins 202. In other implementations, only one of the central pin 204 or the flexible pins 202 is deployed.

As illustrated in FIG. 6A, among others, the windows 265 can be slightly wider than the flexible pins 202 (e.g., within 20%). In some implementations, the width 241 of the window 265 is substantially similar to the width of the flexible pins 202 such that the flexible pins 202 can freely exit the outer stent sub-assembly 240, but the windows 265 can control the lateral position of the flexible pins 202 during deployment. For example, the windows 265 reduce unwanted rotation of the flexible pins 202 as they exit the outer stent sub-assembly 240.

In some implementations, the flexible pins 202 and protective tube 250 are configured to reduce delamination of the flexible pins 202 during deployment. Delamination can be caused by friction between the flexible pins 202 and the outer walls of the windows 265. In some implementations, the possibility of delaminating the flexible pins 202 or microelectrode probe assembly 600 is reduced by sliding the flexible pins 202 along the frustum feature 263 and protective tube 250 rather than the walls of the windows 265. The protective tube 250 can be made out of a polymeric material that is the same or similar to the material used to manufacture the microelectrode probe assembly 600 or the flexible pins 202. The material can be selected to reduce the friction between the protective tube 250 and the frustum feature 263. The protective tube 250 and the frustum feature 263 can be manufactured to reduce abrasion during the deployment of the flexible pins 202 when compared to a device without a protective tube 250. In some implementations, the coefficient of friction of the flexible pins 202 against the protective tube 250 or the frustum feature 263 is between about 0.5 and about 0.01, between about 0.3 and about 0.01, or less than about 0.1. The coefficient of friction of the flexible pins 202 rubbing against the protective tube 250 constructed from a polyimide material may be about half as much when compared to a device where the flexible pins 250 rub against a stainless steel shaft. In some implementations, the coefficient of friction between the flexible pins 202 and the protective tube 250 is achieved because the outer faces of the flexible pins 202 and the protective tube 250 include the same substrate material, such as a polymeric material.

In some implementations, the protective tube 250 and the frustum feature 263 are manufactured from the same material as the flexible pins 202 to limit delamination. For example, the protective tube 250, the flexible pins 202, or the frustum feature 263 can be manufactured from polyimide. In some implementations, the selected material has a low coefficient of friction (COF). For example, the selected material can have a COF less than 0.5, less than 0.2, or less than 0.1. The relatively low COF enables the flexible pins 202 to smoothly slide out of the outer stent sub-assembly 240 during deployment. A low COF reduces the risk of delamination by reducing the force applied to the flexible pins 202 as they exit the outer stent sub-assembly 240.

Figure 6J:
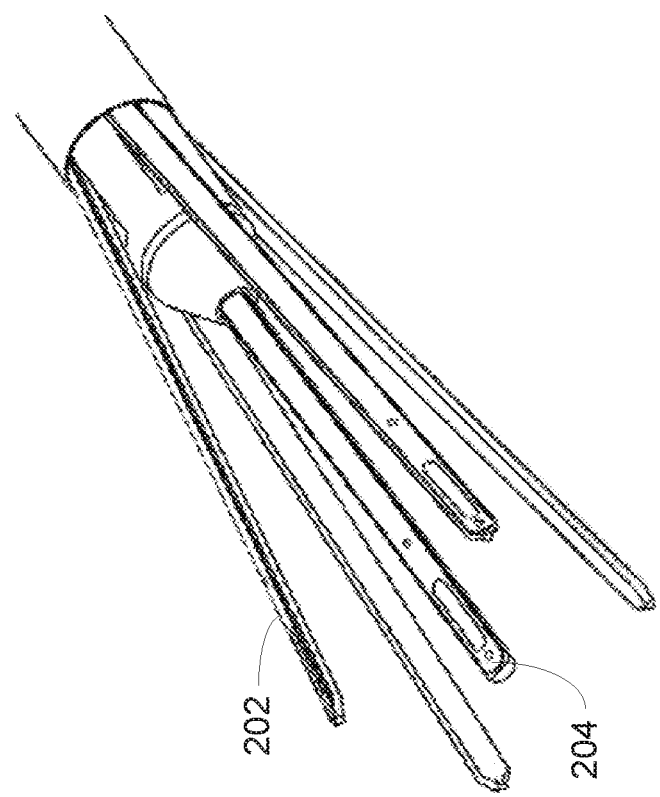
FIGS. 6I and 6J illustrate the tip of the microelectrode drive with a fixed central pin.
Figure 6I:
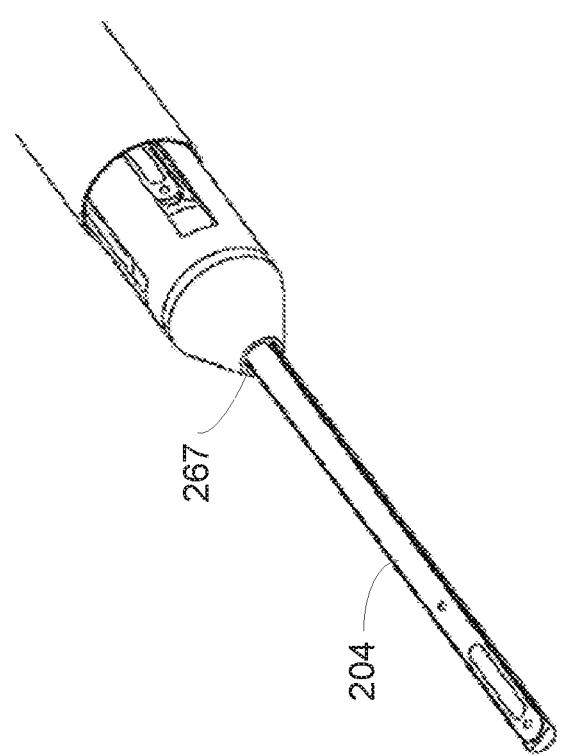

FIGS. 6A and 6B, FIGS. 6I and 6J, among others, illustrate the deployment of the microelectrode probe assembly 600. In some implementations, as illustrated in FIG. 6I, the central pin 204 is fixed in the deployed state. The deployed central pin 204 can reduce tissue coring, a process by which the central channel 267 (without the central pin 204 deployed) can cut through tissue. To reduce the likelihood of coring, the central pin 204 can be fixed in the deployed state and any gap between the central channel 267 and the central pin 204 can be filled. In some implementations, the filling forms a cone-like transition between the base of the central pin 204 and the central channel 267. In some implementations, recording can be made with the central pin 204 during the implantation process to, for example, determine the position of the microelectrode probe assembly 600. FIG. 6J illustrates the deployment of the flexible pins 202, which does not change the position of the central pin 204.

Figure 7A:
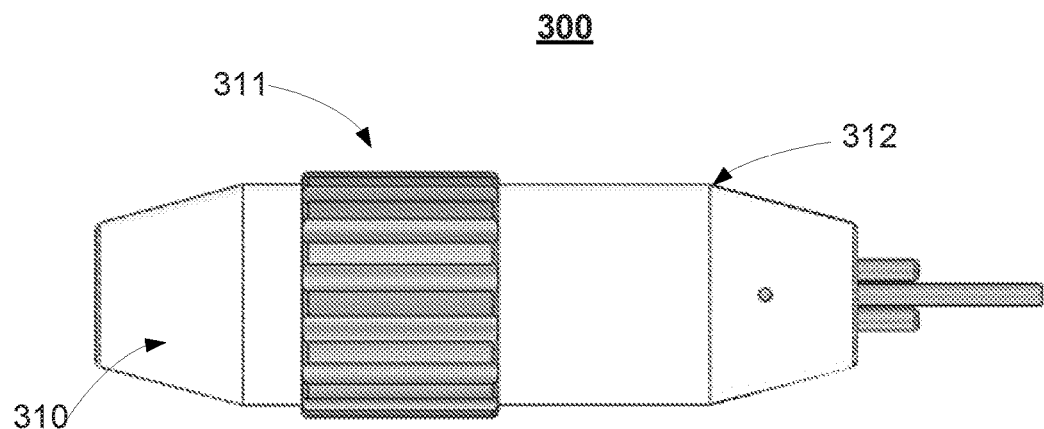
FIG. 7A is a planar view of an exemplary translation system, suitable for use in the microelectrode device of FIG. 1.
Figure 7B:
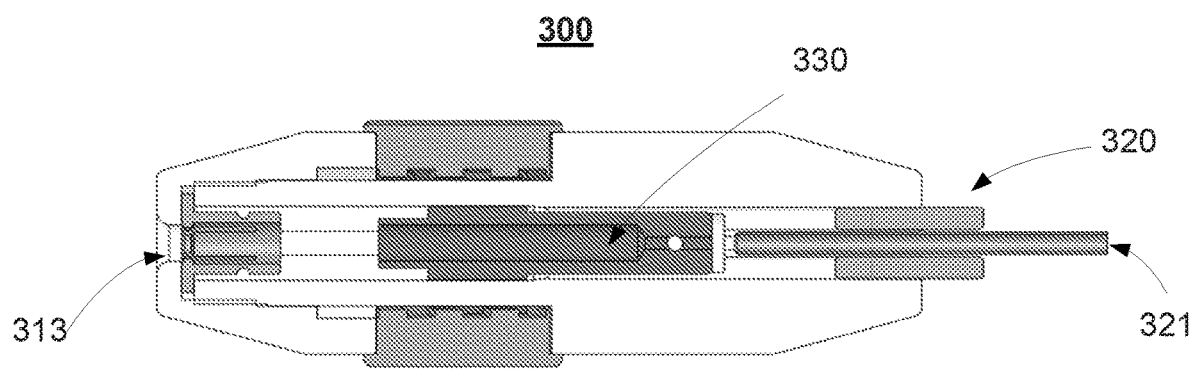
FIG. 7B is a cross-sectional view of the translation system of FIG. 7A.

FIG. 7A illustrates a side view of an exemplary translation system 300, and FIG. 7B illustrates a cross-sectional view of the translation system 300. The translation system 300 can drive the inner stent sub-assembly 270 through the outer stent sub-assembly 240 to deploy and retract the flexible pins 202. As described in relation to FIG. 1, the translation system 300 is coupled to the proximal end of the lead assembly 105. As illustrated in FIG. 7A, the housing of the controller 300 includes a translator ring 311, a removable end cap 310, and a main body housing 312.

Referring to FIG. 7B, the internal components of the translation system 300 include a locking pin 313, a translator rod 330, and guide pins 320. In some implementations, the translation system 300 drives the inner stent sub-assembly 270 by converting a rotational movement of the translator ring 311 into an axial movement of the translator rod 330 along the length of the microelectrode device. The translator ring 311 and the translator rod 330 can act as a lead screw to axially drive the translator rod 330 and the inner stent sub-assembly 270. The internal bore of the translator ring 311 can include a thread that mates with threads on the translator rod 330. As an operator rotates the translator ring 311, the threads of the translator ring 311 impart a force on the threads of the translator rod 330 and an axial movement is induced on the translator rod 330. The translator rod 330 can be coupled with the inner stent sub-assembly 270 of the probe assembly 600 by laser welding or gluing. In some implementations, the translator rod 330 is coupled within the translation system 300 such that it only has one degree of movement along the central axis of the translation system 300.

In some implementations, the controller does not have a translator ring 311, but rather the flexible pins 202 are deployed using a push-pull rod. For example, the push-pull rod can be coupled to the inner stent sub-assembly 270 along its linear axis. As an operator pushes or pulls the push-pull rod, the motion is directly translated to the inner stent sub-assembly 270 and the flexible pins 202.

The translation system 300 includes a removable back cap 310. Removing the back cap 310 provides access to the inner stent sub-assembly 270. The back cap 310 can be unscrewed by hand or with a tool. In some implementations, the translator ring 311 can also be removed from the translation system 300 after removal of the back cap 310. After removal of the back cap 310 and the translator ring 311, an operator is provided adequate access to remove the translator rod 330 and the inner stent sub-assembly 270. In some implementations, the removal of the back cap 310 is a safety mechanism that enables an operator to expose the internal components of the microelectrode device 100 and retract the inner stent sub-assembly 270 and flexible pins 202 in the event of a mechanical failure within the translation system 300. The method of dismantling the translation system 300 is described further in relation to FIGS. 9A-9E.

The translation system 300 can include a centering pin 321 and one or more guide pins 320. In some implementations, the centering pin 321 is used to index the microelectrode device 100 in a stereotactic apparatus (e.g., a stereotactic apparatus used in deep brain stimulation surgery). For example, the centering pin 321 and the guide pins 320 may be placed in a vertical arrangement within the stereotactic apparatus to indicate the initial position of the microelectrode device 100 relative to the stereotactic apparatus. In some implementations, the guide pins 320 form a key that can mate with a lock on a stereotactic apparatus. The guide pins 320 prevent any rotational movement that may be induced when using translator ring 311 and also assist with the initial indexing of the microelectrode device 100 to the stereotactic apparatus.

In some implementations, the centering pin 321 also reinforces the portion of the outer stent sub-assembly 240 where the microelectrode device 100 is typically clamped to the stereotactic apparatus. In some implementations, guide pins 320 are separated from one another (as measured by the distance between their longitudinal axes) by about 4 mm. In some implementations, each guide pin 320 is spaced (as measured by the distance between their longitudinal axes) about 2 mm from the centering pin 321. The interaction of the translation system 300 with the stereotactic apparatus is discussed further in relation to FIGS. 9A-9E.

Figure 7C:
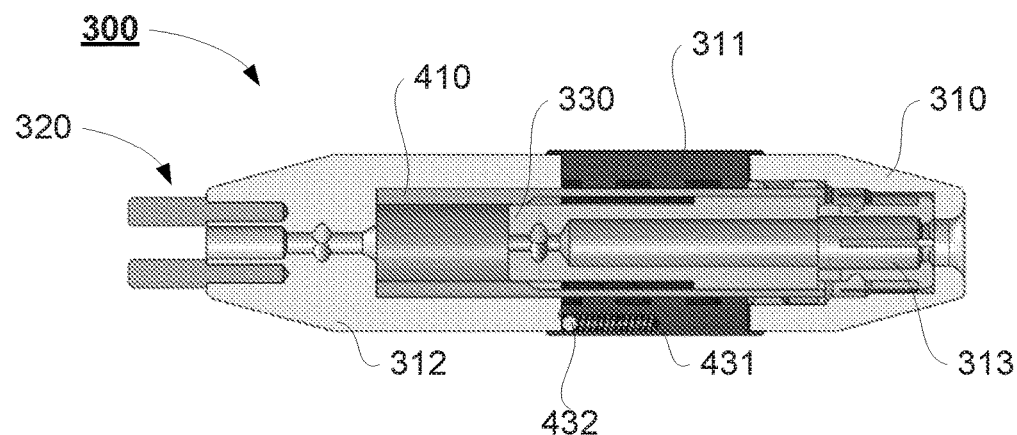
FIG. 7C is a cross-sectional view of an exemplary translation system, suitable for use in the microelectrode device of FIG. 1.
Figure 7D:
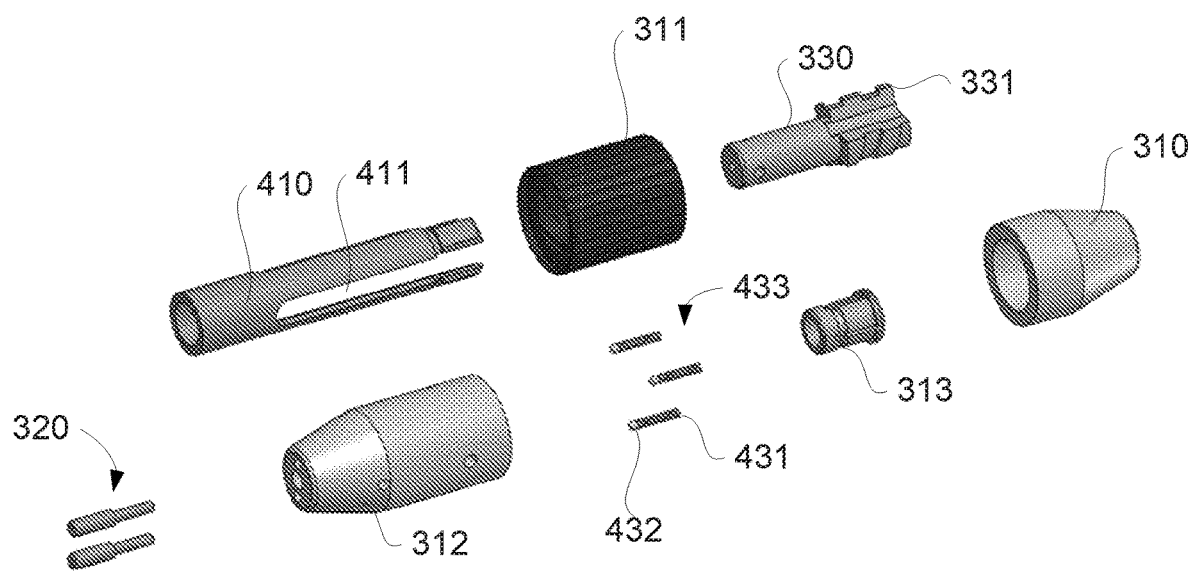
FIG. 7D is an exploded view of the exemplary translation system of FIG. 7C.

FIG. 7C illustrates a cross-sectional view of the example translation system 300, and FIG. 7D illustrates an exploded view of the translation system 300. The translation system 300 includes guiding and indexing features for the deployment of the flexible pins 202. The translation system 300 includes a translator rod 330, which translates the rotation of the translator ring 311 into a linear movement along the central axis of the translation system 300. The translation system 300 also includes a plurality of ball (or other type of) bearings 432 that are held against the translator main body 312 by springs 431. The ball bearings 432 and springs 431 can be part of the indexing system. The translator rod 330 can include guiding structures 331 that fit into guiding slits 411 of the guiding tube 410. The guiding tube 410 can be inserted and fixed into the translator main body 312.

Figure 7E:
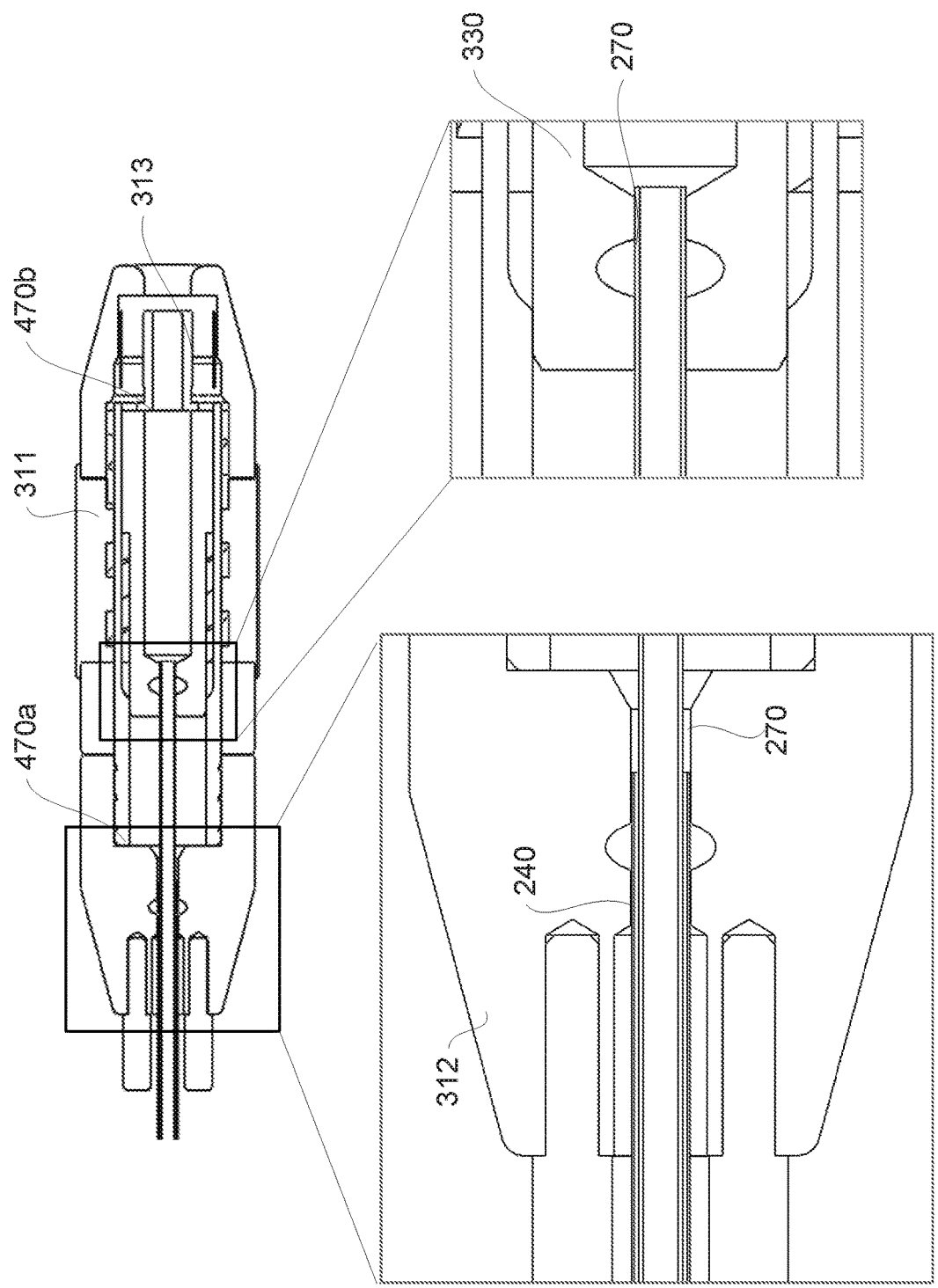
FIG. 7E illustrates a cross-sectional view of the translation system of FIG. 7A.

FIG. 7E illustrates additional detail about the translation system 300. The outer stent sub-assembly 240 can be coupled with the main body housing 312. The above described outer stent sub-assembly 240 can be coupled with the translation system 300, for example by inserting the outer stent sub-assembly 240 into the centering pin 321. In some implementations, the outer stent sub-assembly 240 is coupled to the centering pin 321 by laser welding or gluing. The controller 300 can include at least two mechanical stops 407. The first can be the default, undeployed position as illustrated in FIGS. 5A and 5B, and the second can be the fully deployed position as illustrated in FIGS. 6A and 6B. Mechanical stop 470a can be encountered when the translator rod 330 is in contact with main body 312. Mechanical stop 470b can be encountered when the translator rod 330 is fully in contact with locking pin 313. In some implementations, the first mechanical stop can ensure the flexible pins 202 are not over-retracted within the outer stent sub-assembly 240. The second mechanical stop can ensure the flexible pins 202 are not over deployed. In some implementations, the second mechanical stop enables the flexible pins 202 to be deployed to a length of about 10 mm-8 mm, about 8 mm-6 mm, about 6 mm-4 mm, or about 4 mm-2 mm. The translation system 300 can include a plurality of intermediate steps, which allow the flexible pins 202 to be deployed a predetermined distance less than their fully deployed length.

Figure 7F:
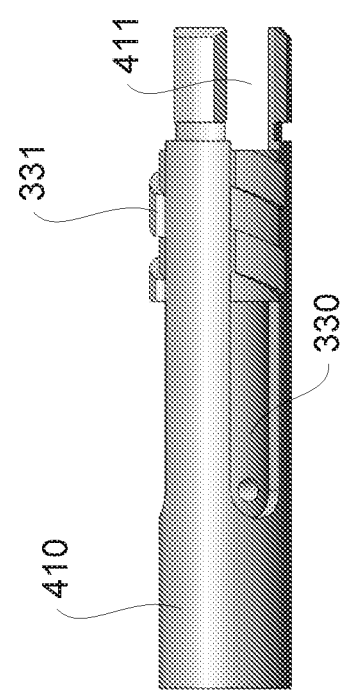
FIG. 7F is a side view of the translator rod and guiding tube of the exemplary translation system of FIG. 7C.

FIG. 7F is a side view of the translator rod 330 and guiding tube 410, when the translator rod 330 is inserted into the guiding tube 410 and illustrated without the other components of the translation system 300. The guiding slits 411 of the guiding tube 410 can provide the translator rod 330 one degree of freedom, e.g., along the central axis of the translation system 300. In the example translation system 300, the guiding tube 410 can include three guiding slits 411, and the translator rod 330 includes three guiding structure 331. The guiding structures 331 slide into the guiding slits 411. Insertion of the guiding structures 331 into the guiding slits 411 can prevent the translator rod 330 from substantially rotating, and can limit the translator rod's movement to a single degree of freedom.

Figure 7I:
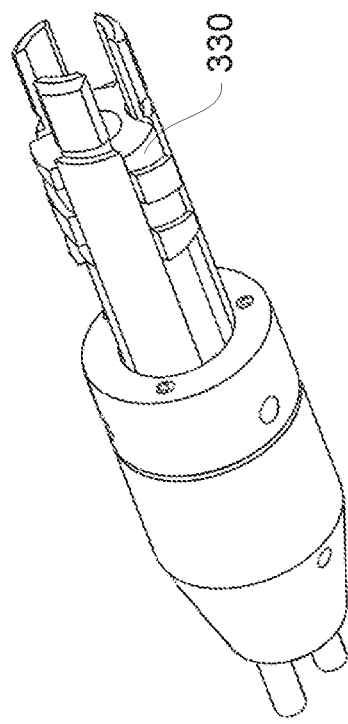
FIGS. 7G-7J illustrate the guiding structures moving along the guiding tube of the translation system of FIG. 7C.
Figure 7J:
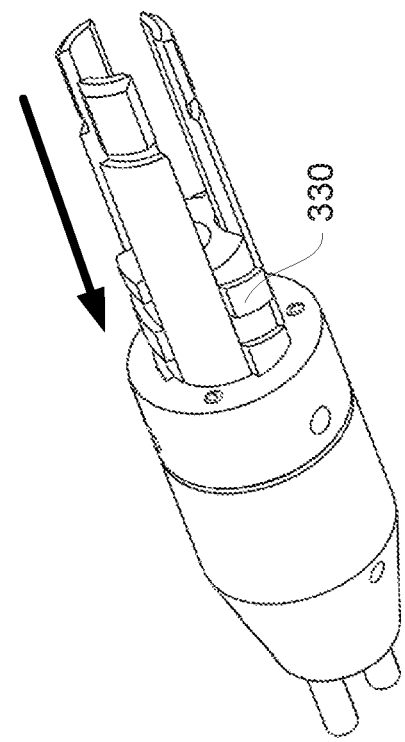
Figure 7G:
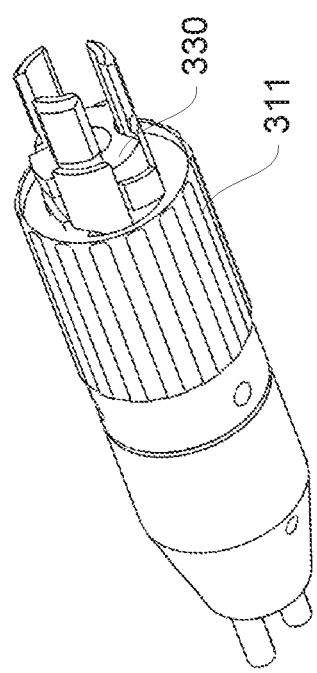
Figure 7H:
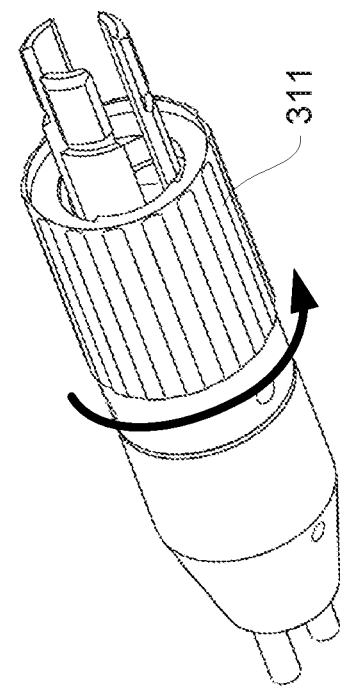

FIGS. 7G, 7H, 7I, and 7J provide additional images of how the guiding structures 331 move along the guiding tube 410 as the user rotates the translator ring 311. FIG. 7G represents the default state of the translation system 300. In FIG. 7I the translator ring 311 is hidden to illustrate that in the default state of the translation system 300, the translator rod 330 is toward the proximal end of the translation system 300. As the user rotates the translator ring 311 (as illustrated in FIG. 7H), the translator rod 330 is advanced, deploying the flexible pins 202. FIG. 7J illustrates the translation system 300 without the translator ring 311 to show that in the deployed state the translator rod 330 is in a position toward the distal end of the translation system 300.

Figure 8A:
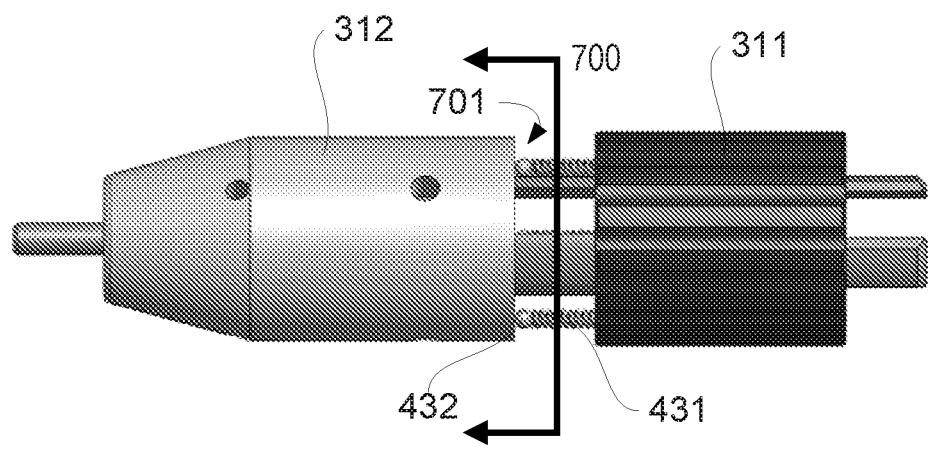
FIGS. 8A and 8B are side and cross-sectional views, respectively, illustrating an exemplary indexing system suitable for use in the microelectrode device of FIG. 1.
Figure 8B:
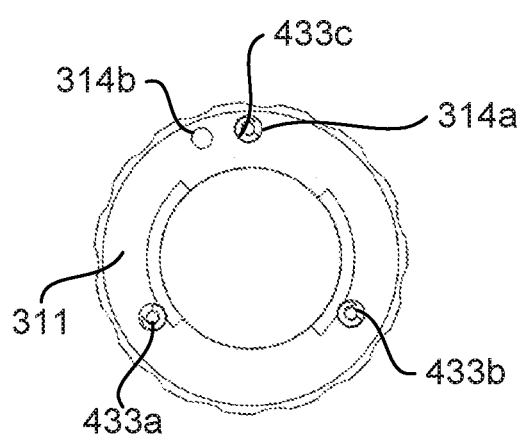
Figure 8D:
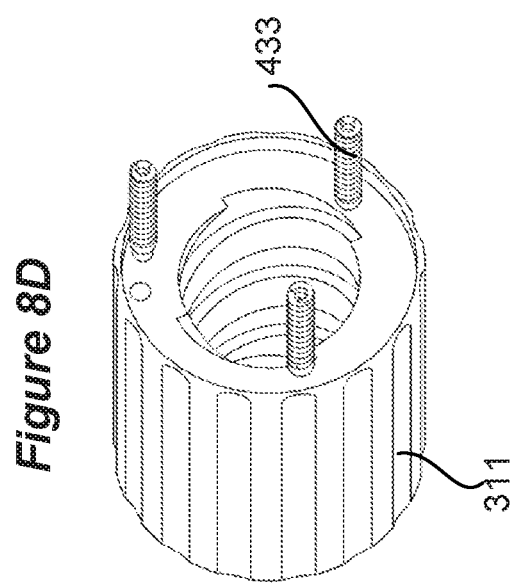
FIGS. 8C-8G illustrate how the various components of the indexing system fit together.
Figure 8C:
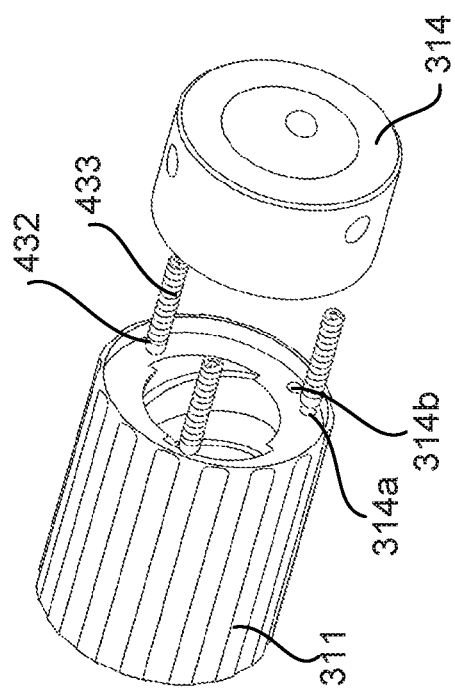
Figure 8G:
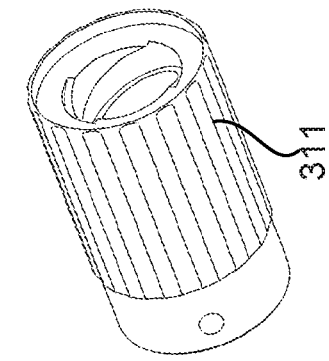
Figure 8F:
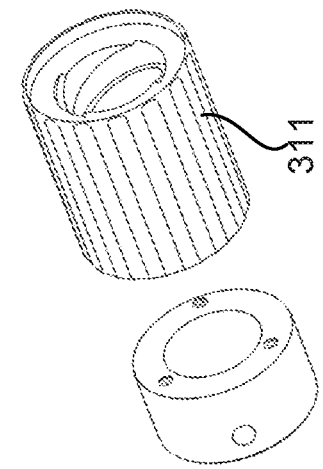
Figure 8E:
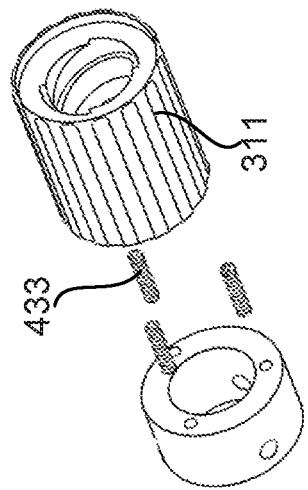

The translation system 300 includes an indexing system to enable an operator to deploy the flexible pins 202 to predetermined lengths. FIG. 8A illustrates a side view of a partially constructed translation system 300, and FIG. 8B illustrates a cut away along plain 700 of the partially constructed translation system 300. In FIG. 8A, the translator ring 311 is pulled away from the translator main body 312 to expose the ball bearings 432 and springs 431 of the indexing system (collectively referred to as ball bearing-springs 433). The indexing system allows for control of the translator rod 330 between the undeployed and deployed state of the flexible pins 202. The indexing system enables a user to determine if the flexible pins are deployed, retracted, or at predetermined positioned therebetween.

FIG. 8B illustrates the back face 701 of the translator main body 312. The indexing system includes the ball bearing-springs 433 and indexing holes 314a and 314b. The ball bearing-spring system 433 is composed of ball bearings 432 of a diameter of 1 mm and a spring 431. The spring 431 holds the ball bearings 432 against the back face 701 of the translator main body 312. These springs 431 can be received by holes drilled into the translator ring 311. The indexing holes 314 can be semi-hemispherical holes milled into the back face 701 of the translator main body 312. The diameter of the indexing holes 314 can be approximately (e.g., +/−10%) the same diameter of the ball bearings 432, such that the indexing holes 314 can receive the ball bearings 432. As the translator ring 311 is rotated the ball bearings 432 fall into the indexing holes 314 to indicate predetermined amounts of deployment of the flexible pins 202. In some implementations, the ball bearing-spring system 433 reduces mechanical play that may be present in mechanical translation system 300. For example, the ball bearing-spring system 433 can provide a mechanical stability feature (e.g., a three contact point system) that can reduce the friction between the translator ring 311 and the translator main body 312.

The distance from the central axis of the translation system 300 can be different for one or more of the ball bearing-spring system 433. For example, FIG. 8B depicts ball bearing-spring systems 433a and 433b that can be radially offset to a slightly different difference than ball bearing-spring 433c. In this example, ball bearing-spring 433c is used in the indexing system while the ball bearing-springs 433a and 433b are used for mechanical stability. The indexing holes 314 can be offset the same distance from the central axis of the translation system 300 as the ball bearing-spring 433c. For example, when indexing hole 314a receives the ball bearings 432 of ball bearing-spring 433c the flexible pins 202 are fully retracted and when the translator ring 311 is rotated such that the indexing hole 314b receives the ball bearings 432 of ball bearing-spring 433c the flexible pins 202 are fully deployed. In some implementations, a plurality of indexing holes are placed along the radial path between indexing hole 314a and indexing hole 314b such that the flexible pins 202 may be deployed to specific lengths. The length of the track virtually drawn along that particular radius defines the maximum linear travel distance induced on translator rod 330. FIGS. 8C, 8D, 8E, 8F, and 8G illustrate how the translator ring 311, ball bearing-springs 433, and the other components of the indexing system fit together.

FIGS. 9A-9E illustrate an example of the systematic disassembling of the translation system 300. The translation system 300 can be disassembled as a safety mechanism to retract the flexible pins 202 if the translation system 300 becomes stuck. In some implementations, first, the removable end cap 310 is removed to reveal the locking pin 313 and the guiding tube 410. Next, the locking pin 313 is removed and then the guiding tube 410. Then, the translator rod 330 is removed to reveal the inner stent sub-assembly 270, which an operator may remove by hand to retract the flexible pins 202.

Figure 10B:
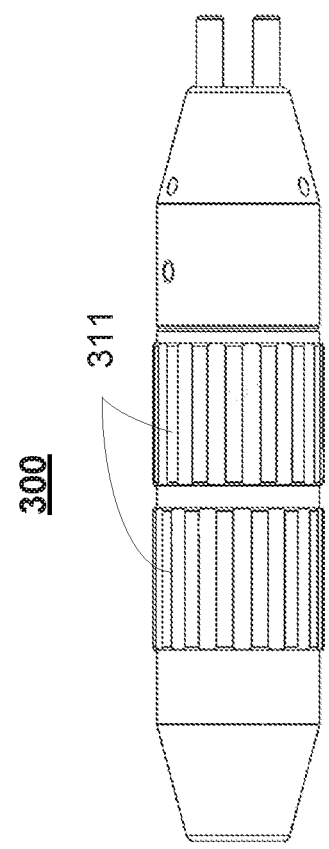
FIGS. 10A-10D illustrate views of an example translation system with multiple translator rings.

In some implementations, one or more of the flexible pins 202 are independently controllable. The translation system 300 can include different translator rings 311 to control the deployment of each of the independently controllable flexible pins 202. FIG. 10A illustrates a perspective view of a translation system 300 with two translator rings 311. FIG. 10B illustrates a side view of the translation system 300 with two translator rings 311. The translation system 300 with two translator rings 311 could be used, for example, to control a microelectrode device with an independently controlled central pin. For example, the first translator ring 311 could be used to control the deployment of the central pin and the second translator ring 311 could be used to control the deployment of the remaining flexible pins.

Figure 10D:
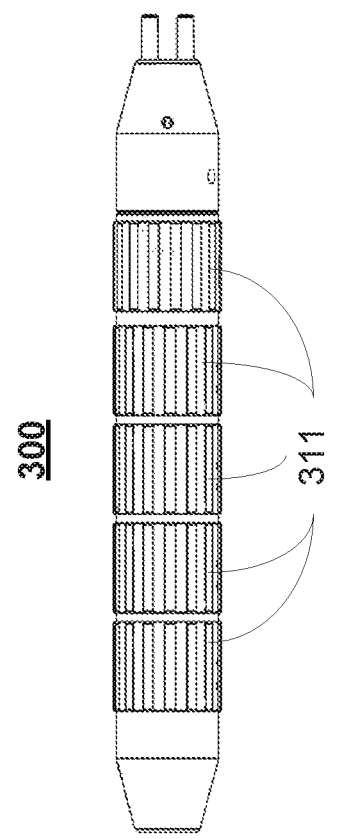
Figure 10A:
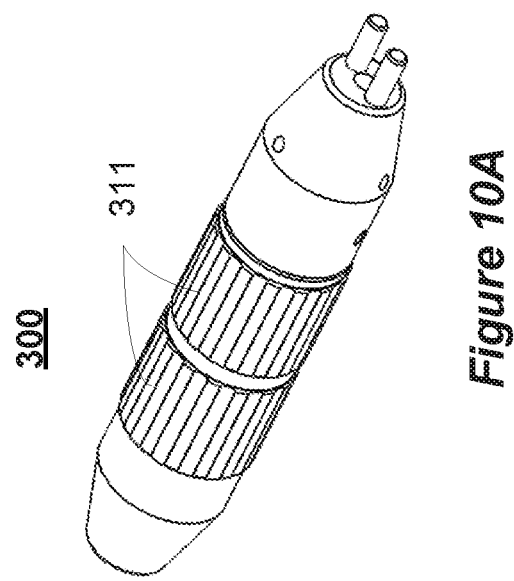
Figure 10C:
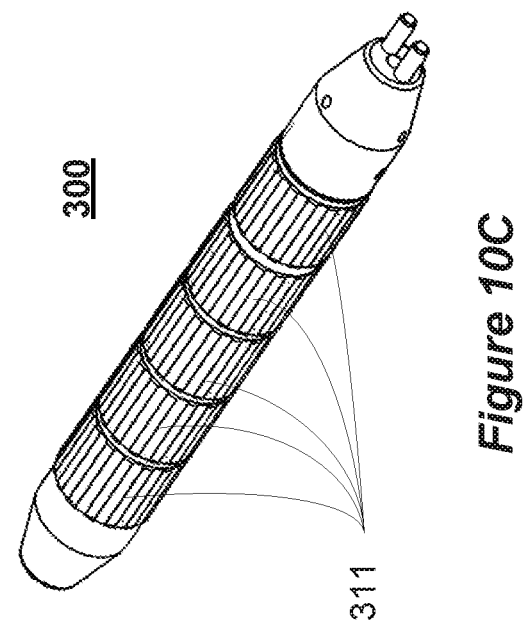

FIGS. 10C and 10D illustrate perspective and side views, respectively, or a translation system 300 with five translator rings 311. In some implementations, each of the flexible pins of the microelectrode device can be independently controlled. Accordingly, each of the flexible pins of the microelectrode device can be coupled to one of the five translator rings 311 to enable independent deployment and retraction of the flexible pins. In some implementations with independently deployable flexible pins, the surgeon could deploy only the flexible pins that are of diagnostic interest during a surgical procedure, and avoid deploying the flexible pins that may cause patient harm.

Figure 11A:
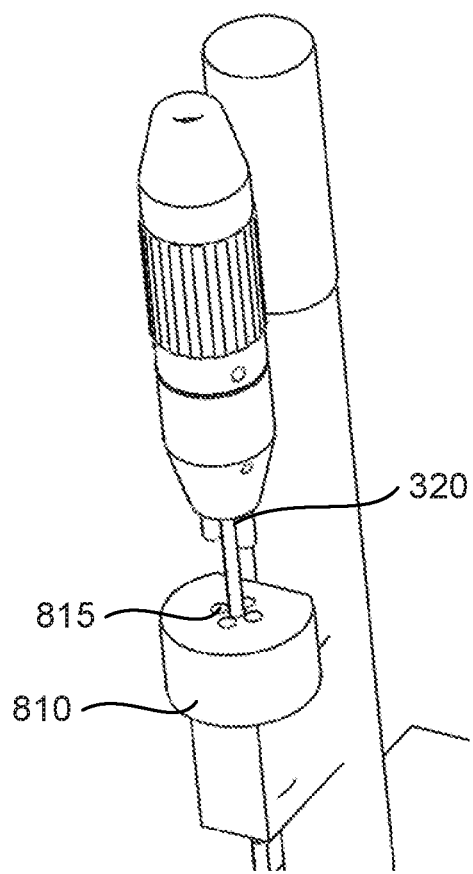
FIGS. 11A, 11B, and 11C illustrate how the translation system interacts with an example stereotactic apparatus.
Figure 11B:
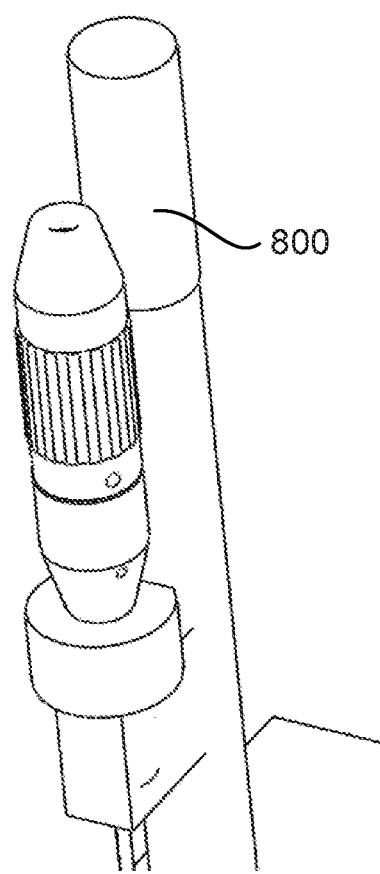

FIGS. 11A and 11B illustrate how the translation system 300 interacts with an example stereotactic apparatus 800. The holding piece 810 of the apparatus 800 includes a plurality of mating holes 815. The holes 815 are configured to mate with the guide pins 320 of the translation system 300. Once the guide pins 320 are mated with the holes 815, as illustrated in FIG. 11B, among other, the translation system 300 cannot rotate around its central axis.

Figure 11C:
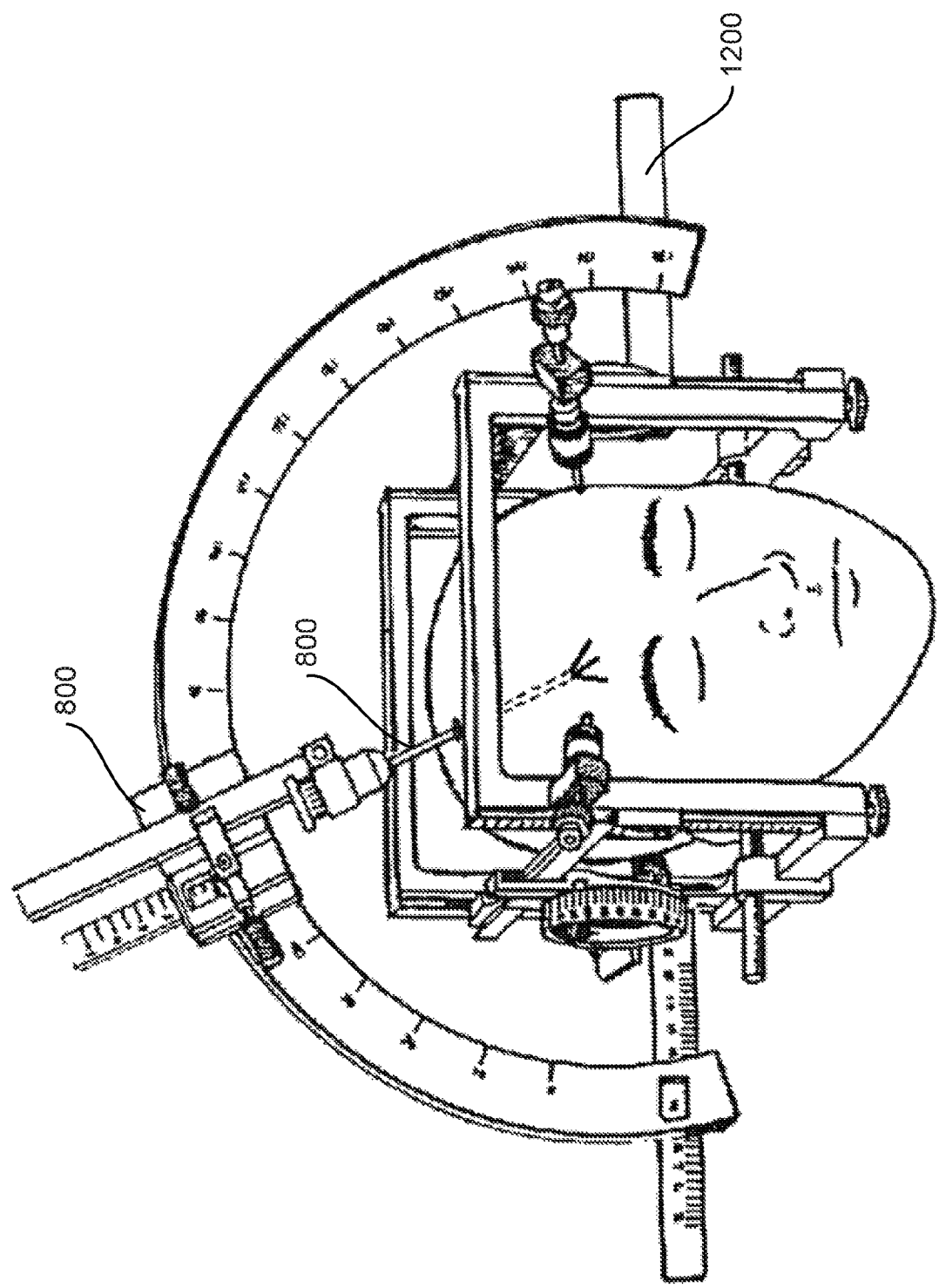

FIG. 11C illustrates microelectrode device 100 in use with a stereotactic frame 1200. The stereotactic frame 1200 can be placed and fixed to the patient's head prior surgery. The caliper device 800 can be part of the stereotactic frame 1200 and can be used to interface with the microelectrode device 100 and can determine the microelectrode device's location relative to the patient's head. The insertion trajectory of the device 100 can be guided using a guiding tube 1210 which can interface with stereotactic apparatus 800 through the holding piece 810. With the microelectrode device 100 at a desired location, the pins can be deployed as illustrated in FIG. 11C.

In some implementations, the microelectrode device is configured to prevent extraction of the electrode device while the flexible pins are deployed into a patients tissue. In some implementations, the translation system 300 of the microelectrode device includes alarms to alert the surgeon when the flexible pins are deployed or a mechanism that prevents removal of the microelectrode device when the flexible pins are deployed.

The translation system 300 can include a visual or an audible alarm system such as LEDs or buzzers. When the flexible pins are in their retracted state, the alarm can be off. When one of the flexible pins is deployed, the alarm can activate. For example, when the flexible pins are retracted a red LED on the translation system 300 may be off. However, when one of the flexible pins are deployed power may be provided to the red LED to alert the surgeon that he should not remove the microelectrode device from the patient. The translation system 300 can include a second LED, such as a green LED, that indicates to the surgeon that the flexible pins are retracted and it is safe to remove the microelectrode device from the patient. The alarm can be powered by battery resident within the translation system 300.

The visual alarm of the translation system 300 can include a mechanical indicator which exposes a colored ring, or other static visible indicator, when one or more flexible pins are deployed. This visible indicator can remain visible until each of the flexible pins are retracted. The mechanical indicator may not require a power source to generate the alert to the surgeon.

Figure 12:
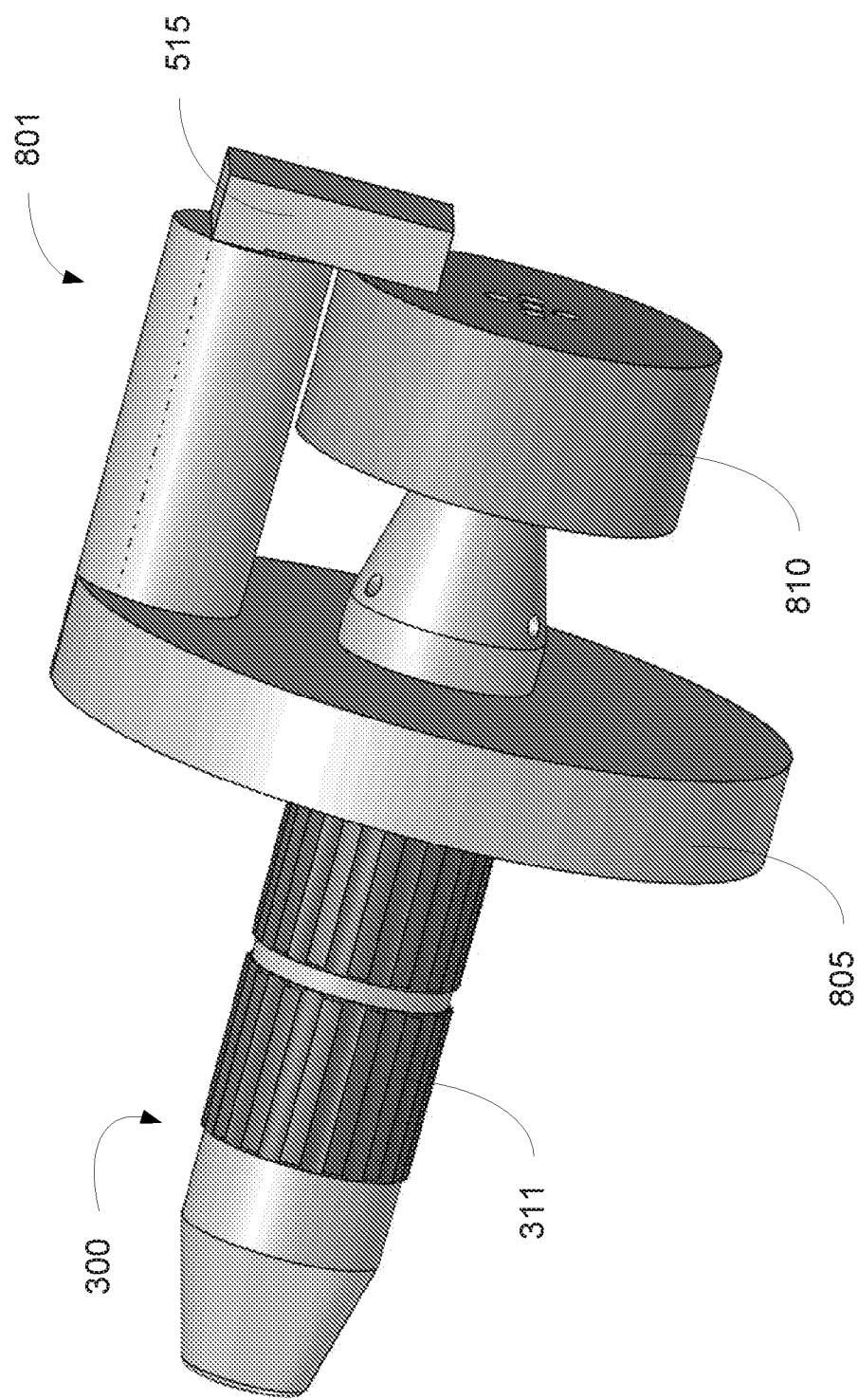
FIG. 12 illustrates the interaction of the translation system and a portion of a stereotactic frame to prevent removal of the microelectrode device.

The translation system 300 can physically prevent the removal of the microelectrode device form the patient when one or more flexible pins are deployed. FIG. 12 illustrates the interaction of the translation system 300 and a portion of a stereotactic frame 800 to prevent removal of the microelectrode device.

In some implementations, a portion of the stereotactic frame 800 can be electrically or mechanically connected to the translation system 300 to prevent the displacement of the microelectrode device in certain conditions, such as when the flexible pins are deployed. The stereotactic frame 800 could electrically, or mechanically, block the movement of the microelectrode device with respect to the patient's brain, if the flexible pins are not in a safe position.

FIG. 12 illustrates an example mechanical system for preventing the retraction of the microelectrode device when one or more flexible pins are deployed. A blocking mechanism 801 can be coupled to the translation system 300. The blocking mechanism includes a rotary extension 805. As one of the translation rings 311 are rotated to deploy one or more of the flexible pins, gears within the rotary extension 805 can rotate a blocking extension 515 over a lip of a holding piece 810. For example, if the surgeon attempted to retract the microelectrode device by pulling the translation system 300, the blocking extension 515 would hold the microelectrode device in place. With the flexible pins retracted, the blocking extension 515 would not catch the holding piece 810 and the microelectrode device could be withdrawn from the patient.

Various implementations of the microelectrode device have been described herein. These embodiments are giving by way of example and not to limit the scope of the present disclosure. The various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the disclosure.

Devices described herein as either acute or chronic may be used acutely or chronically. They may be implanted for such periods, such as during a surgery, and then removed. They may be implanted for extended periods, or indefinitely. Any devices described herein as being chronic may also be used acutely.

The present disclosure is not to be limited in terms of the particular embodiments described in this application, which are intended as illustrations of various aspects. Modifications and variations can be made without departing from its spirit and scope of this disclosure. Functionally equivalent methods and apparatuses may exist within the scope of this disclosure. Such modifications and variations are intended to fall within the scope of the appended claims. The subject matter of the present disclosure includes the full scope of equivalents to which it is entitled. This disclosure is not limited to particular methods, reagents, compounds compositions or biological systems, which can vary. The terminology used herein is for the purpose of describing particular embodiments, and is not intended to be limiting.

With respect to the use of substantially any plural or singular terms herein, the plural can include the singular or the singular can include the plural as is appropriate to the context or application.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Claims directed toward the described subject matter may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, such recitation can mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction would include but not be limited to systems that have A alone, B alone, C alone, A and B together, A and C together, B and C together, and/or A, B, and C together, etc.). Any disjunctive word or phrase presenting two or more alternative terms, whether in the description, claims, or drawings, can contemplate the possibilities of including one of the terms, either of the terms, or both terms. For example, the phrase "A or B" includes the possibilities of "A" or "B" or "A and B."

In addition, where features or aspects of the disclosure are described in terms of Markush groups, the disclosure is also described in terms of any individual member or subgroup of members of the Markush group.

Any ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. Language such as "up to," "at least," "greater than," "less than," and the like include the number recited and refer to ranges which can be subsequently broken down into subranges as discussed above. Finally, a range includes each individual member.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program can be stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis, preprocessing, and other methods described herein can also be implemented as a computer-readable storage medium, configured with a computer program, where the storage medium on configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

In some embodiments, a program product may include a signal bearing medium. The signal bearing medium may include one or more instructions that, when executed by, for example, a processor, may provide the functionality described above. In some implementations, signal bearing medium may encompass a computer-readable medium, such as, but not limited to, a hard disk drive, a Compact Disc (CD), a Digital Video Disk (DVD), a digital tape, memory, etc. In some implementations, the signal bearing medium may encompass a recordable medium, such as, but not limited to, memory, read/write (R/W) CDs, R/W DVDs, etc. In some implementations, signal bearing medium may encompass a communications medium such as, but not limited to, a digital or an analog communication medium (e.g., a fiber optic cable, a waveguide, a wired communications link, a wireless communication link, etc.). Thus, for example, the program product may be conveyed by an RF signal bearing medium, where the signal bearing medium is conveyed by a wireless communications medium (e.g., a wireless communications medium conforming with the IEEE 802.11 standard).

Any of the signals and signal processing techniques may be digital or analog in nature, or combinations thereof.

While certain embodiments of this disclosure have been particularly shown and described with references to preferred embodiments thereof, various changes in form and details may be made therein without departing from the scope of the disclosure.

What is claimed:
1. An implantable microelectrode device, comprising:
an elongated shaft having an outer wall and a distal end, the outer wall of the elongated shaft defining an internal lumen, the outer wall of the elongated shaft defining a plurality of windows toward the distal end;
an end cap coupled with the distal end of the elongated shaft, the end cap defining a central channel, the end cap having a frustum end, the frustum end defining a projection into the internal lumen of the elongated shaft;
a protective tube coupled with an outer surface of the elongated shaft and covering a portion of each of the plurality of windows; and
a probe assembly to slide through the internal lumen of the elongated shaft, the probe assembly comprising:
a central pin configured for deployment via the central channel;
a plurality of flexible pins, each of the plurality of flexible pins configured for deployment through a corresponding window of the plurality of windows via sliding through the internal lumen, the deployment of each of the plurality of flexible pins through the corresponding window at an exit angle defined at least in part by the projection of the frustum end of the end cap into the internal lumen and a placement of a distal end of the protective tube over the corresponding window, the deployment of each of the plurality of flexible pins through the corresponding window independent of the deployment of the central pin via the central channel; and
microelectromechanical system (MEMS) components having a first MEMS component disposed on the central pin and a second MEMS component disposed on one or more of the plurality of flexible pins.

2. The device of claim 1, comprising:
the plurality of flexible pins configured to slide through the corresponding window.

3. The device of claim 1, comprising:
the second MEMS component comprises a first plurality of MEMS legs, each of the first plurality of MEMS legs aligned and coupled with an outer face of one of the plurality of flexible pins.

4. The device of claim 3, comprising:
a second plurality of MEMS legs coupled to the first plurality of MEMS legs by a foldable strip, each of the second plurality of MEMS legs aligned and coupled with an inner face of one of the plurality of flexible pins.

5. The device of claim 3, each of the first plurality of MEMS legs comprising at least one electrode.

6. The device of claim 1, comprising:
the protective tube including a polymeric material.

7. The device of claim 1, comprising:
a material of the protective tube having a coefficient of friction between about 0.5 and about 0.01 with respect to the plurality of flexible pins.

8. The device of claim 1, comprising:
a material of the protective tube having a coefficient of friction between about 0.2 and about 0.01 with respect to the plurality of flexible pins.

9. The device of claim 1, comprising:
the protective tube and the plurality of flexible pins made of a same substrate material.

10. The device of claim 1, wherein a minimum of the exit angle is defined by the frustum of the end cap and a maximum of the exit angle is defined by the distal end of the protective tube.

11. The device of claim 1, wherein the plurality of windows in the outer wall of the elongated shaft include at least four windows.

12. The device of claim 1, comprising:
a translation system comprising a translation ring and a translator rod, the translation system configured to convert a rotational movement of the translation ring into an axial movement of the translator rod.

13. The device of claim 12, comprising:
the translator rod coupled with the probe assembly.

14. The device of claim 12, comprising:
a second translation ring configured to convert a rotational movement of the second translation ring into an axial movement to deploy the central pin through the central channel of the end cap.

15. The device of claim 1, comprising:
an alarm configured to indicate when at least one of the plurality of flexible pins is deployed.

16. A method of obtaining neurological activity information, comprising:
implanting microelectrode device within a vicinity of a neurological target, the microelectrode device comprising:
an elongated shaft having an outer wall and a distal end, the outer wall of the elongated shaft defining an internal lumen, the outer wall of the elongated shaft defining the outer wall defining a plurality of windows;
an end cap coupled with the distal end of the elongated shaft, the end cap defining a central channel, the end cap having a frustum end, the frustum end defining a projection into the internal lumen of the elongated shaft;
a protective tube coupled with an outer surface of the elongated shaft and covering a portion of each of the plurality of windows; and
a probe assembly to slide through the internal lumen of the elongated shaft, the probe assembly comprising microelectromechanical system (MEMS) components, a central pin, a plurality of flexible pin, the MEMS components having a first MEMS component disposed on the central pin and a second MEMS component disposed on one or more of the plurality of flexible pins each of the plurality of flexible pins comprising a plurality of electrode sites; and
deploying at least one of the central pin through the central channel or the plurality of flexible pins through a corresponding window of the plurality of windows via sliding through the internal lumen, the deployment of each of the plurality of flexible pins through the corresponding window at an exit angle defined at least in part by the projection of the frustum end of the end cap into the internal lumen and a placement of a distal end of the protective tube over the corresponding window, the deployment of each of the plurality of flexible pins through the corresponding window independent of the deployment of the central pin through the central channel.

17. The method of claim 16, comprising:
coupling the microelectrode device with a stereotactic apparatus.

18. The method of claim 16, further comprising:
rotating a first translator ring of the microelectrode device to deploy at least one of the plurality of flexible pins through a different one of the plurality of windows.

19. The method of claim 18, further comprising:
rotating a second translator ring of the microelectrode device to deploy the central pin through the central channel of the end cap.

20. The method of claim 16, further comprising:
retracting at least one of the plurality of flexible pins through the different one of the plurality of windows.

21. The method of claim 16, further comprising:
coupling the microelectrode device to a neural recording and neurostimulation device; and
recording neurological activity using the plurality of electrode sites.

22. The method of claim 16, comprising:
sliding the plurality of flexible pins along the frustum end of the end cap and the distal end of the protective tube.

23. The method of claim 16, wherein a minimum of the exit angle is defined by the frustum of the end cap and a maximum of the exit angle is defined by the distal end of the protective tube.

24. The method of claim 16, wherein the plurality of windows in the outer wall of the elongated shaft include at least four windows.

* * * * *